United States Patent
Jiang et al.

(10) Patent No.: US 12,234,232 B2
(45) Date of Patent: Feb. 25, 2025

(54) AROMATIC HETEROCYCLIC COMPOUND WITH KINASE INHIBITORY ACTIVITY

(71) Applicant: SHANGHAI ENNOVABIO PHARMACEUTICALS CO., LTD., Shanghai (CN)

(72) Inventors: Lei Jiang, Shanghai (CN); Jianwen Deng, Shanghai (CN); Zhiyong Feng, Shanghai (CN); Shengyang Liu, Shanghai (CN); Xudong Mao, Shanghai (CN); Ke Shang, Shanghai (CN); Jianyong Shou, Shanghai (CN); Danyi Wu, Shanghai (CN); Xiaoping Xie, Shanghai (CN); Yuan Xu, Shanghai (CN); Haixia Zhao, Shanghai (CN); Jianhua Zhang, Shanghai (CN); Mingwei Zheng, Shanghai (CN)

(73) Assignee: SHANGHAI ENNOVABIO PHARMACEUTICALS CO., LTD., Shanghai (CN)

( * ) Notice: Subject to any disclaimer, the term of this patent is extended or adjusted under 35 U.S.C. 154(b) by 964 days.

(21) Appl. No.: 17/278,405

(22) PCT Filed: Sep. 23, 2019

(86) PCT No.: PCT/CN2019/107381
§ 371 (c)(1),
(2) Date: Mar. 22, 2021

(87) PCT Pub. No.: WO2020/057669
PCT Pub. Date: Mar. 26, 2020

(65) Prior Publication Data
US 2021/0371415 A1 Dec. 2, 2021

(30) Foreign Application Priority Data

Sep. 21, 2018 (CN) .................. 201811109355.9
Sep. 21, 2018 (CN) .................. 201811110497.7

(51) Int. Cl.
| | | |
|---|---|---|
| *C07D 471/04* | (2006.01) | |
| *C07D 487/04* | (2006.01) | |
| *C07D 519/00* | (2006.01) | |

(52) U.S. Cl.
CPC ......... *C07D 471/04* (2013.01); *C07D 487/04* (2013.01); *C07D 519/00* (2013.01)

(58) Field of Classification Search
CPC ... C07D 471/04; C07D 487/04; C07D 519/04
See application file for complete search history.

(56) References Cited

FOREIGN PATENT DOCUMENTS

| WO | 2004089913 A1 | 10/2004 |
| WO | 2017050938 A1 | 3/2017 |
| WO | 2018134213 A1 | 7/2018 |

OTHER PUBLICATIONS

International Search Report mailed Jan. 8, 2020 corresponding to PCT/CN2019/107381 Filed Sep. 23, 2019; 2 pages.
Wang, Zhihui et al., "Synthesis of Azaindoles," *Progress in Chemistry* (Oct. 31, 2012) 24(10): 1974-1982. See, English language abstract.

*Primary Examiner* — Kamal A Saeed
(74) *Attorney, Agent, or Firm* — Mintz Levin Cohn Ferris Glovsky and Popeo, P.C.

(57) ABSTRACT

Provided are a JAK kinase inhibitor, preparation and use thereof. In particular, provided is a compound of Formula I, wherein each group is as described in the specification. The compound has an excellent JAK inhibitory activity, and therefore can be used to prepare pharmaceutical compositions for the treatment of cancer and other diseases related to JAK activity.

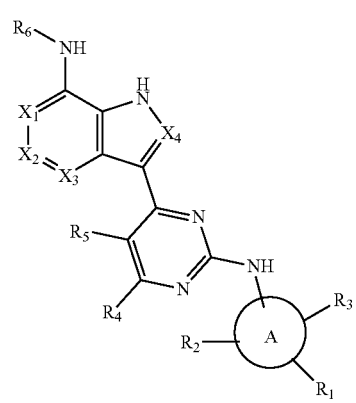

9 Claims, No Drawings

AROMATIC HETEROCYCLIC COMPOUND WITH KINASE INHIBITORY ACTIVITY

FIELD OF THE INVENTION

The present invention relates to the field of small molecule drugs. Specifically, the present invention relates to a kinase inhibitor and the preparation and use thereof.

BACKGROUND OF THE INVENTION

Janus kinase (JAK) is a cytoplasmic tyrosine protein kinase responsible for transducing many inflammation-related cytokine signals from cytokine membrane receptor to STAT transcription factor. It is generally believed that there are mainly four family members: JAK1, JAK2, JAK3, and TYK2. When a specific cytokine binds to its receptor, the JAK family members coupled to the receptor undergo autophosphorylation and/or transphosphorylation with each other, and then phosphorylate the substrate protein STATs. The phosphorylated STAT migrates into the nucleus to regulate the transcription, so as to transmit extracellular signals into the cells. JAK-STAT intracellular signal transduction pathway is the core signal transduction pathway in the body which is related to immune and inflammatory responses. JAK-STAT is an important signal transmission that mediates interferon IFN, most of the interleukins ILs, and a variety of cytokines and endocrine factors, such as EPO, TPO, GH and GM-CSF, etc.

JAK/STAT signal transduction abnormalities are related to many diseases, including organ transplant rejection, multiple sclerosis, rheumatoid arthritis, type I diabetes, lupus, psoriasis, asthma, food allergy, atopic dermatitis and rhinitis, skin rash, etc.; there are also reports on it closely related to the occurrence and development of solid and hematological tumor and myeloproliferative disorder (including lung cancer, breast cancer, chronic spontaneous myelofibrosis, polycythemia, idiopathic thrombocytosis, etc.).

JAK kinase inhibitors provide a new approach for the treatment of JAK-related diseases such as inflammatory diseases, autoimmune diseases, myeloproliferative diseases and cancers, by blocking JAK-related signal transduction. For example, there are JAK kinase inhibitors approved by the FDA for the treatment of rheumatoid arthritis and other diseases. However, several adverse effects were associated with these drugs, such as anemia, serious infection, and the risk of cardiovascular diseases. Therefore, it is highly desired to develop inhibitors with better JAK selectivity or pharmacokinetic properties that demonstrate better safety to treat JAK-STAT related diseases effectively.

In summary, there is an urgent need to develop next generation of novel selective JAK inhibitors in this field.

BRIEF SUMMARY OF THE INVENTION

The purpose of the present invention is to provide a JAK kinase inhibitor and the preparation and use thereof.

In the first aspect of the present invention, a compound according to Formula I is provided:

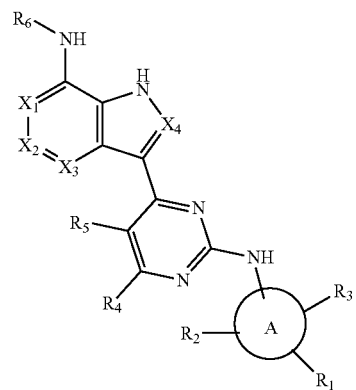

I wherein,
$X^1$, $X^2$, $X^3$, $X^4$ are each independently CH or N; and at least one of $X^1$, $X^2$, $X^3$, $X^4$ is N;

ring is selected from the group consisting of 6-10 membered aryl, or 5-10 membered heteroaryl;

$R^1$ is independently selected from the group consisting of H, substituted or unsubstituted C1-C6 alkyl, substituted or unsubstituted 3-6 membered heterocyclyl (including 1-3 heteroatoms selected from N, S and O), —S(═O)$_2$R$_7$;

$R^2$, $R^3$ are independently selected from the group consisting of H, halogen, CN, substituted or unsubstituted C1-C6 alkyl, substituted or unsubstituted C1-C6 alkoxyl, substituted or unsubstituted 3-6 membered heterocyclyl (including 1-3 heteroatoms selected from N, O and S), —S(═O)$_2$R$_7$, —NHS(═O)$_2$R$_7$;

$R^4$, $R^5$ are independently selected from the group consisting of H, halogen, CN, substituted or unsubstituted C1-C6 alkyl;

$R^6$ is selected from the group consisting of H, substituted or unsubstituted C1-C6 alkyl, R$^7$—C(═O)—, R$^8$—S(═O)$_2$—, R$^9$R$^{10}$N—C(═O)—, R$^{11}$R$^{12}$N—S(═O)$_2$—, substituted or unsubstituted 5-12 membered heterocyclyl with 1-3 heteroatoms selected from N, S and O (including single ring, spiro ring, bridged ring or fused ring), substituted or unsubstituted C6-C10 aryl, substituted or unsubstituted 5-10 membered heteroaryl with 1-3 heteroatoms selected from the group consisting of N, S and O;

$R^7$, $R^8$, $R^9$, $R^{10}$, $R^{11}$, $R^{12}$ are each independently selected from the group consisting of H, substituted or unsubstituted C1-C6 alkyl, substituted or unsubstituted C1-C6 alkoxyl, substituted or unsubstituted C3-C8 cycloalkyl, substituted or unsubstituted 5-12 membered heterocyclyl with 1-3 heteroatoms selected from the group consisting of N, S and O;

unless otherwise specified, "substituted" refers to being substituted by one or more (for example, 2, 3, 4, etc.) substituents selected from the group consisting of halogen, C1-C6 alkoxyl, halogenated C1-C6 alkoxyl, C3-C8 cycloalkyl, halogenated C3-C8 cycloalkyl, methyl sulfone, oxo (═O), —CN, hydroxy, —NH$_2$, C1-C6 amine, carboxy, C1-C6 amide (—C(═O)—N(Rc)$_2$ or —NH—C(═O)(Rc), Rc is H or C1-C5 alkyl), or substituted or unsubstituted groups selected from the group consisting of C1-C6 alkyl, C6-C10 aryl, 5-10 membered heteroaryl with 1-3 heteroatoms selected from N, S, O, —(CH$_2$)—C6-C10 aryl, —(CH$_2$)-(5-10 membered heteroaryl with 1-3 heteroatoms selected from N, S and O), -(5-10 membered heteroarylene with 1-3 heteroatoms selected from N, S and O)—(C1-C6 alkyl), 5-12 membered heterocyclyl with 1-3 heteroatoms selected from N, S and O (including single ring, spiro ring, bridged ring or fused ring), and the substituents thereof are selected from the group consisting of halogen, C1-C6 alkyl, C1-C6 alkylene-OH, C1-C6 alkoxyl, oxo, —S(O)$_2$CH$_3$, —CN, —OH, C6-C10 aryl, 3-10 membered heteroaryl with 1-3 heteroatoms selected from N, S and O, —C(O)CHNH$_2$, —C(O)CHOH;

and in the compound of Formula I, each chiral center is in R configuration or S configuration.

In another preferred example, the 5-12 member heteroaromatic ring is selected from the group consisting of pyridine ring, pyrimidine ring, pyridazine ring, tetrazine ring, triazine ring, pyrrole ring, thiophene ring, furan ring, tetrazole ring, triazole ring, imidazole ring, thiazole ring, oxazole ring, pyrazole ring, isothiazole ring, isoxazole ring, oxadiazole ring, thiadiazole ring.

In another preferred example, the compound of Formula I has a structure according to Formula Ia or Ib:

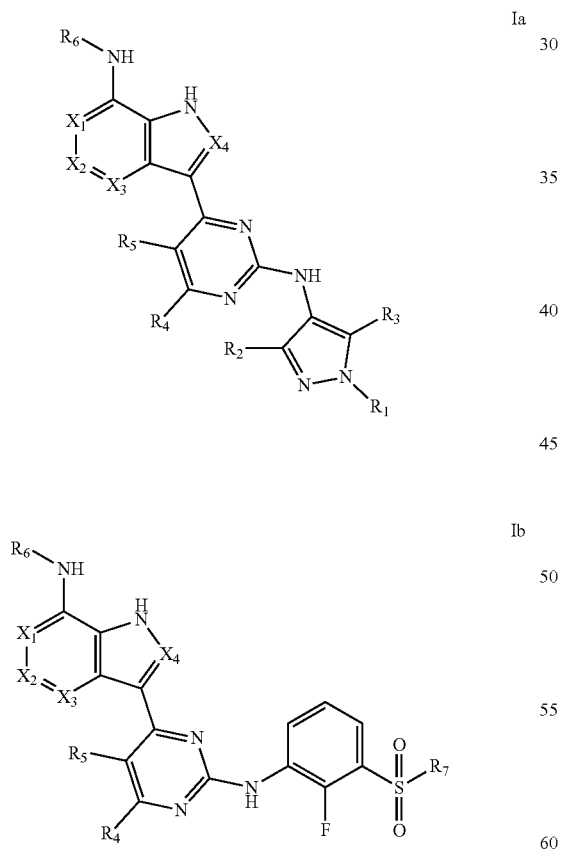

wherein, R$_7$ is selected from the groups consisting of H, substituted or unsubstituted C1-C6 alkyl, substituted or unsubstituted C3-C8 cycloalkyl.

In another preferred example, the compound of Formula I has a structure selected from the following group:

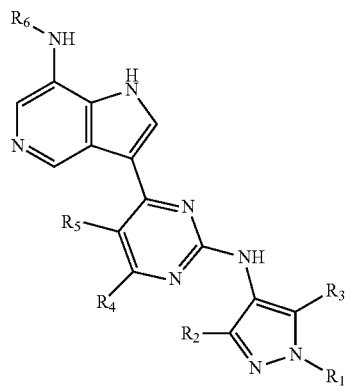

I-1

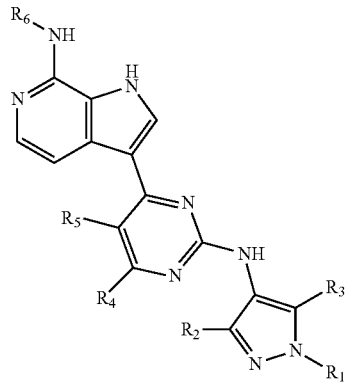

I-2

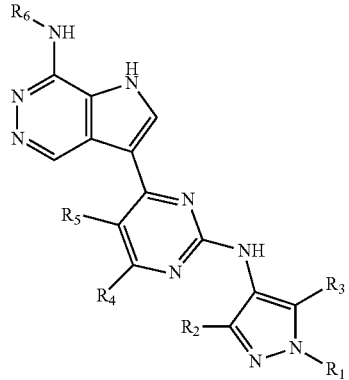

I-3

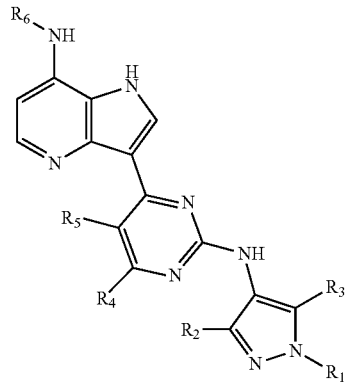

I-4

-continued
I-5
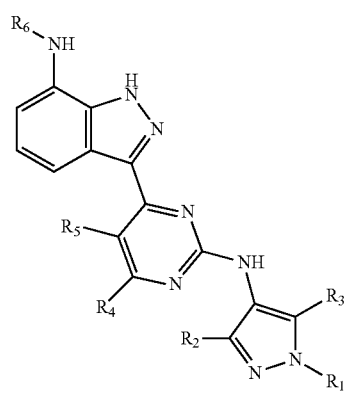
I-6
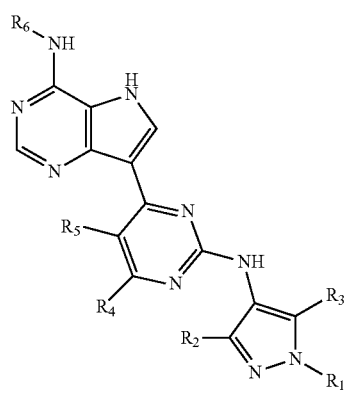
I-7
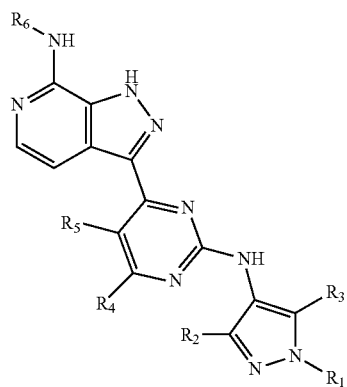
I-8
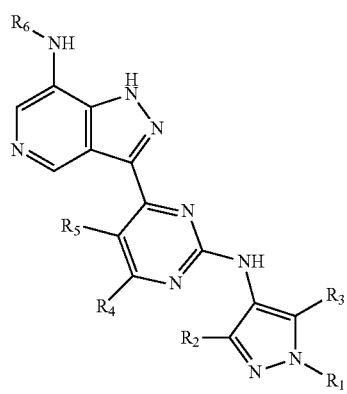
-continued
I-9
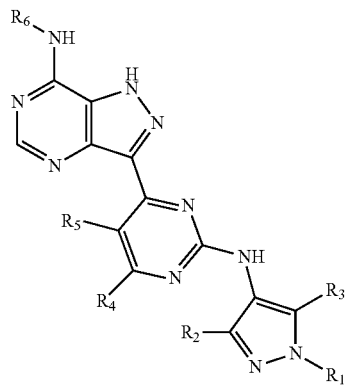
I-10
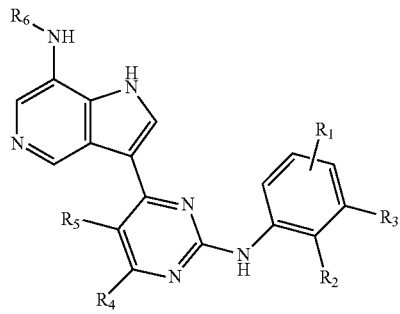
I-11
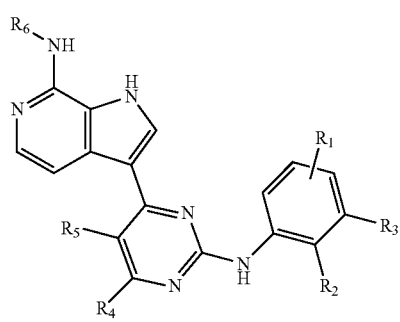
I-12
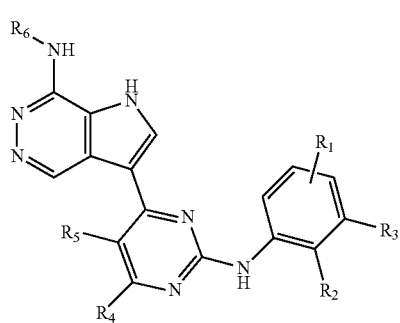
I-13
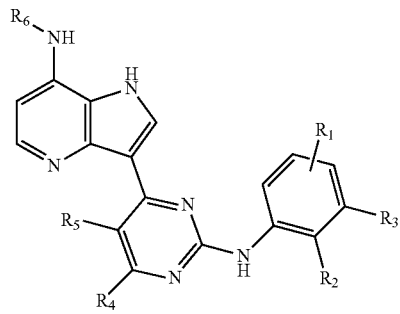

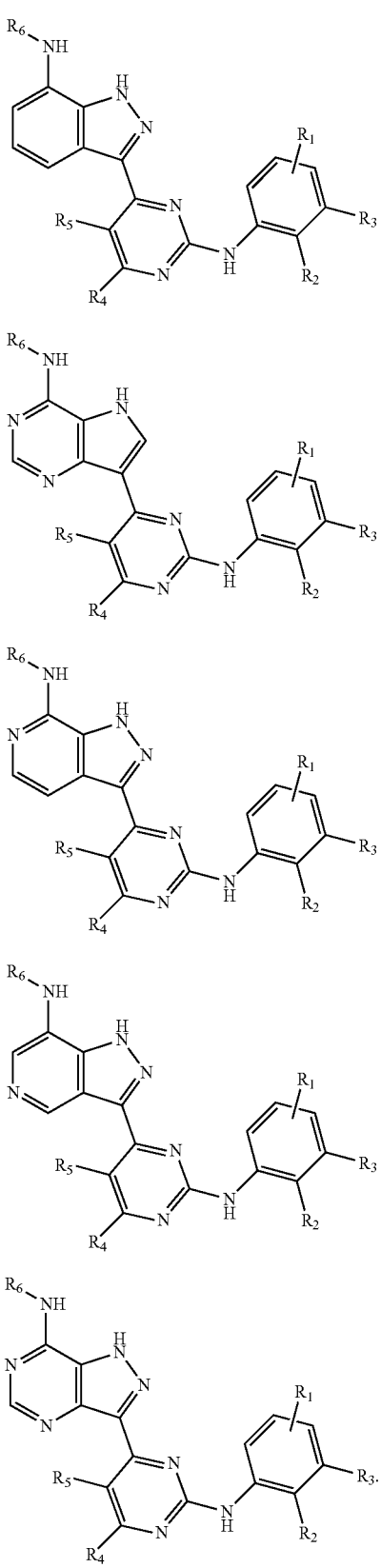

In another preferred example, the compound has a structure according to Formula II:

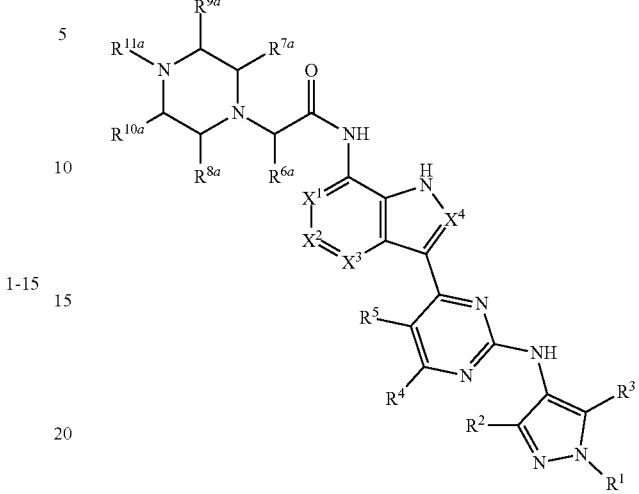

wherein, $R^{6a}$ is selected from the group consisting of H, substituted or unsubstituted C1-C6 alkyl, substituted or unsubstituted C1-C6 alkoxyl;

$R^{7a}$, $R^{8a}$, $R^{9a}$, $R^{10a}$ are selected from the group consisting of hydrogen, halogen, substituted or unsubstituted C1-C6 alkyl;

$R^{11a}$ is selected from the group consisting of hydrogen, substituted or unsubstituted C1-C6 alkyl, substituted or unsubstituted C1-C6 alkoxyl, substituted or unsubstituted C1-C6 amine;

or any two groups of $R^{7a}$, $R^{8a}$, $R^{9a}$, $R^{10a}$ and $R^{11a}$ are connected to form $-(CH_2)_n-$:

wherein, the substitution refers to one or more hydrogen atoms on the group being replaced by the substituents selected from the group consisting of halogen, hydroxyl, substituted or unsubstituted C1-C6 alkoxyl.

In another preferred example, $R^{7a}$, $R^{8a}$, $R^{9a}$, $R^{10a}$ are selected from the group consisting of hydrogen, methyl;

$R^{11a}$ is selected from the group consisting of methyl, ethyl, hydroxy ethyl, methoxy ethyl, halogenated C1-C6 alkyl.

In another preferred example, $R^4$ is H, and $R^5$ is methyl.

In another preferred example, $R^1$ is selected from the group consisting of methyl, ethyl.

In another preferred example, $R^2$ is selected from the group consisting of methyl, ethyl, methoxy, ethoxy.

In another preferred example, $R^3$, $R^4$ are each independently hydrogen.

In another preferred example, $R^5$ is selected from the group consisting of hydrogen, methyl, chlorine, fluorine, bromine, trifluoromethyl.

In another preferred example, $R^6$ is selected from the group consisting of 3,3,3-trifluoro-2-hydroxypropyl, 2-(4-methylpiperazin-1-yl)butyryl.

In another preferred example, the compound of Formula I is selected from the following group:

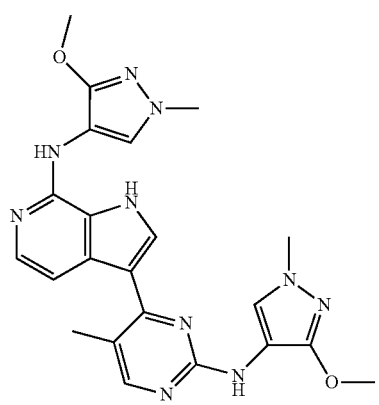
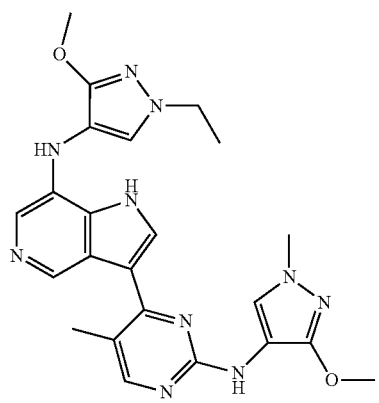
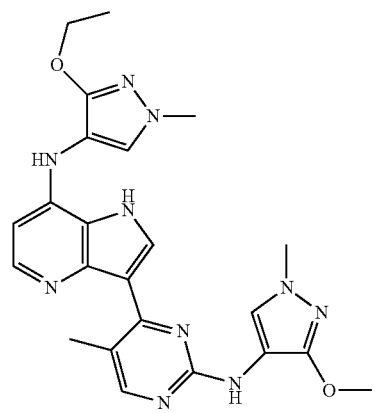
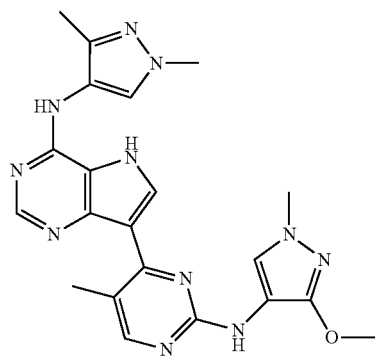
-continued
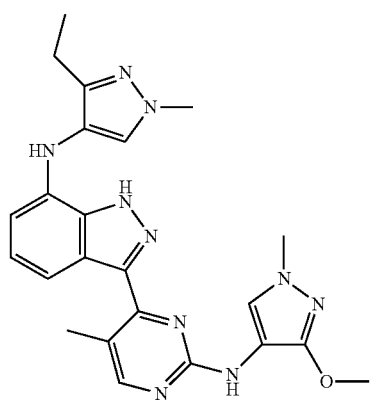
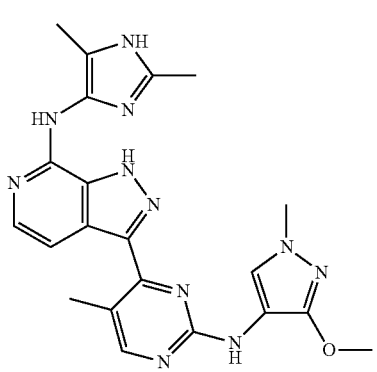
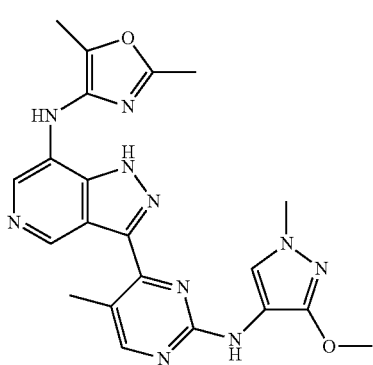
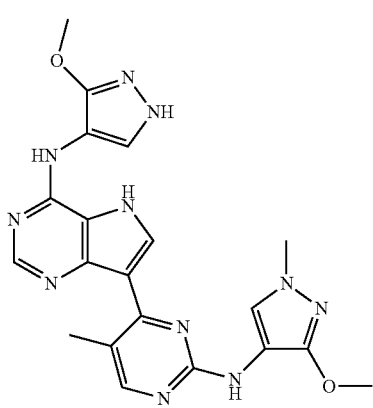

-continued
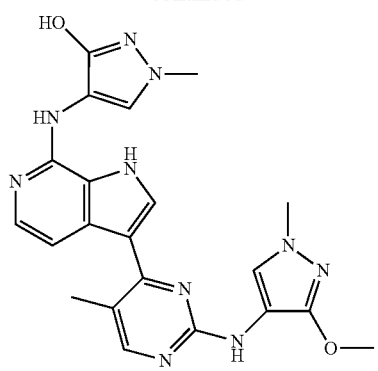
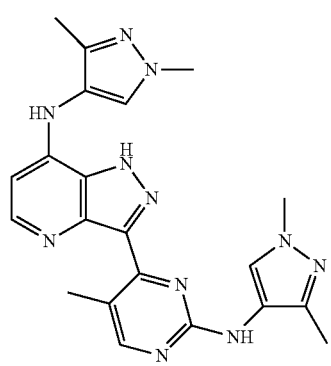
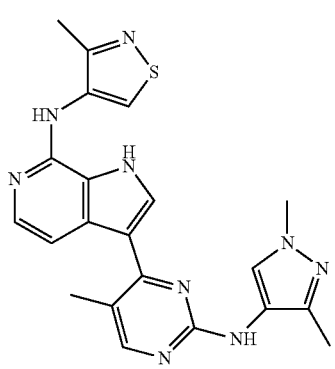
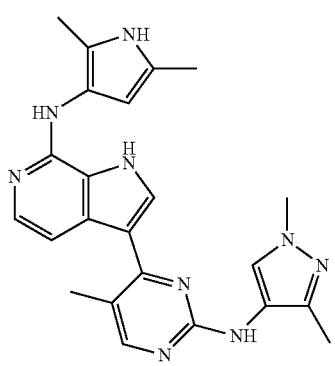
-continued
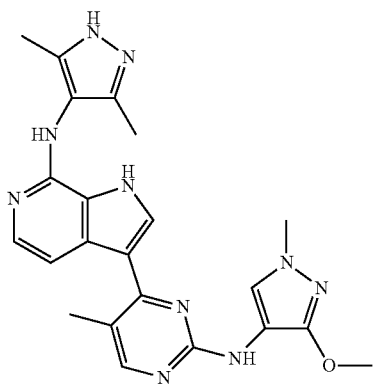
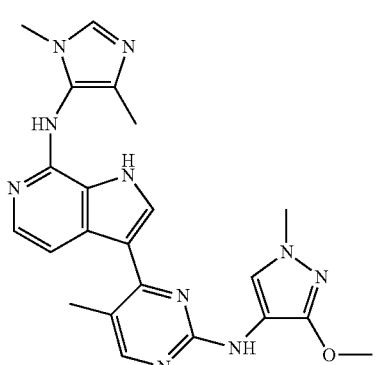
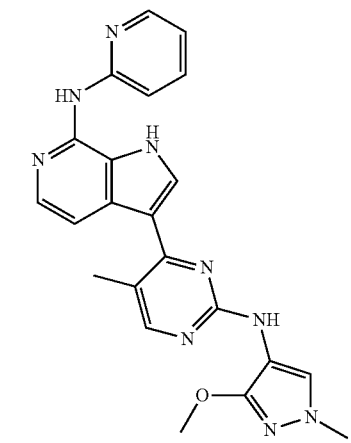
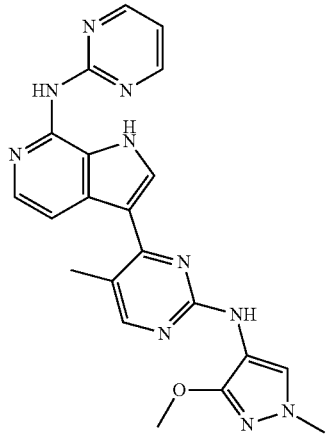

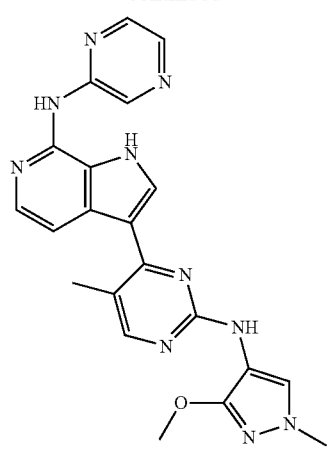
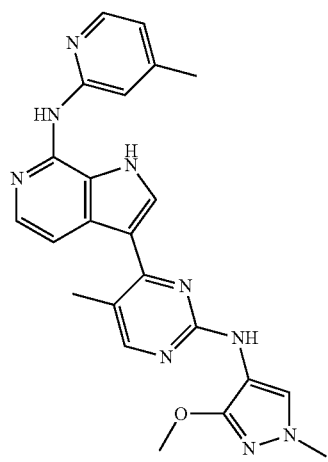
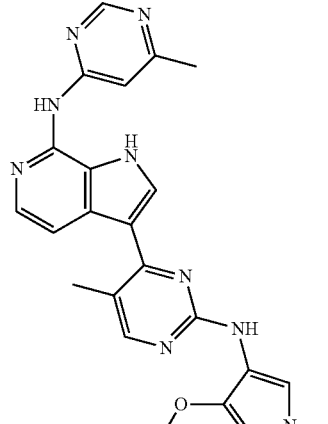
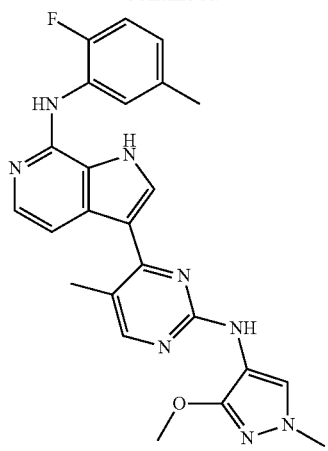
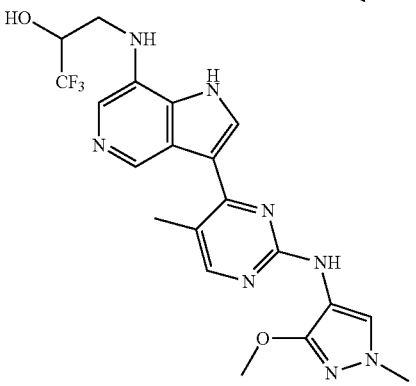
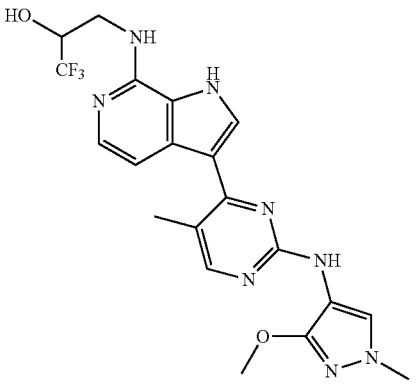
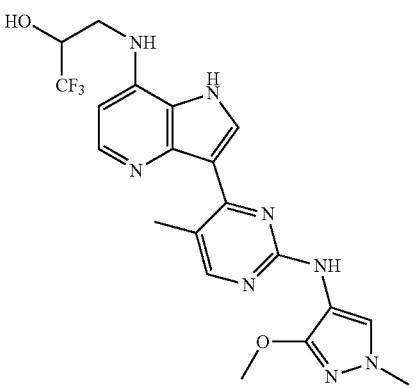

-continued
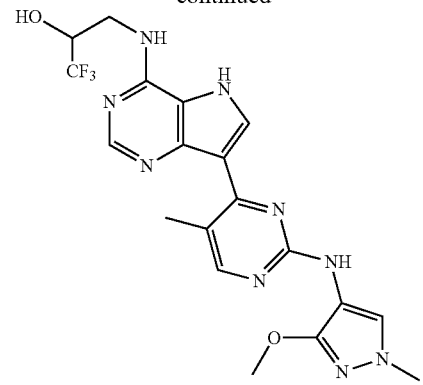
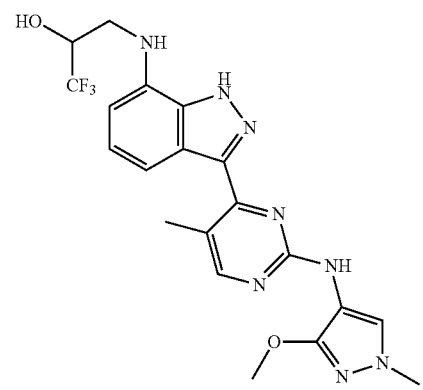
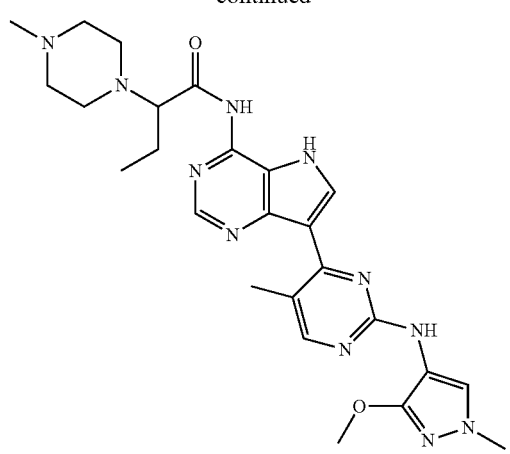
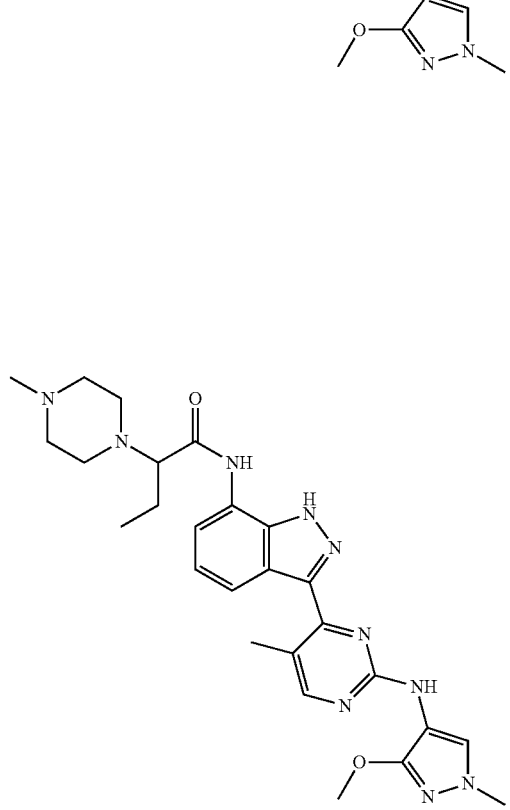

17
-continued
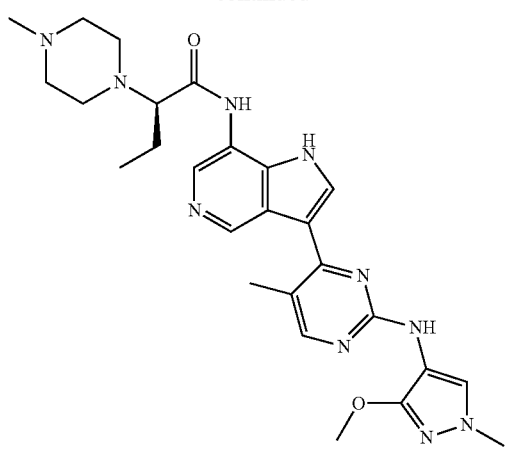
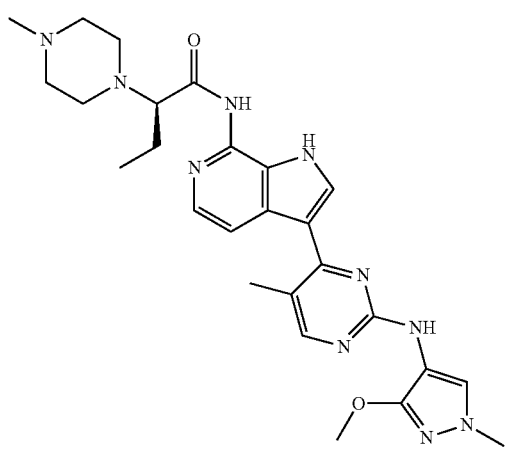
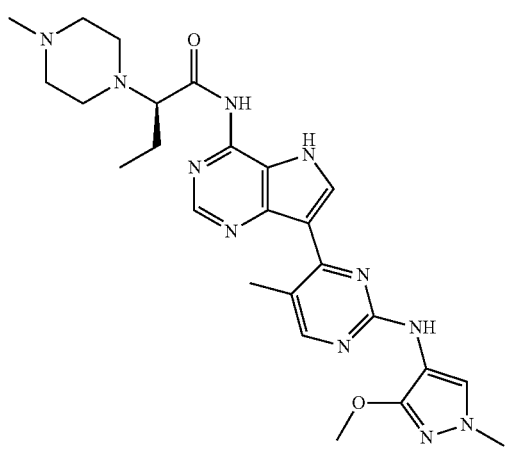
18
-continued
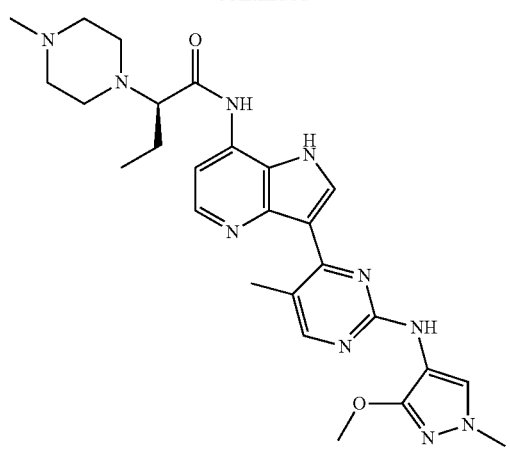
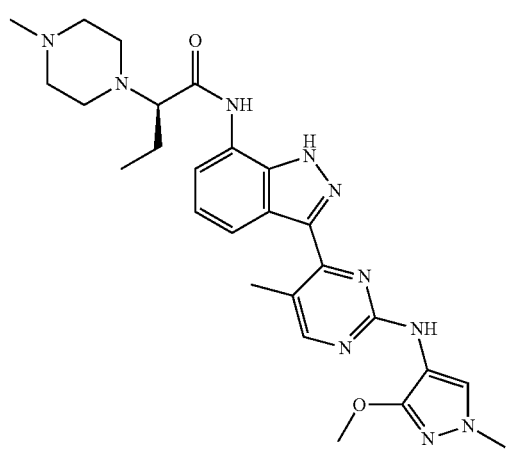
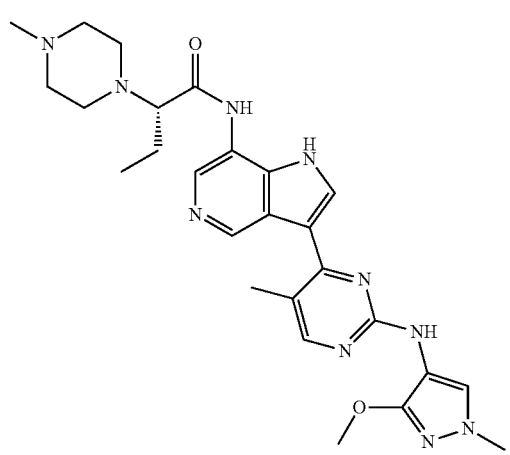

-continued
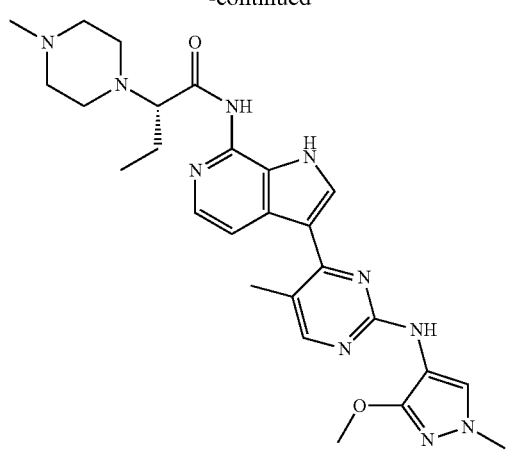
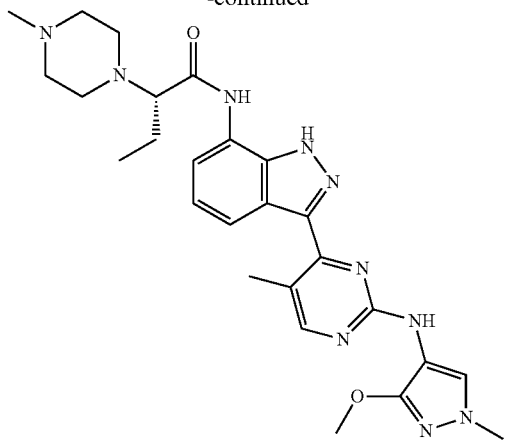
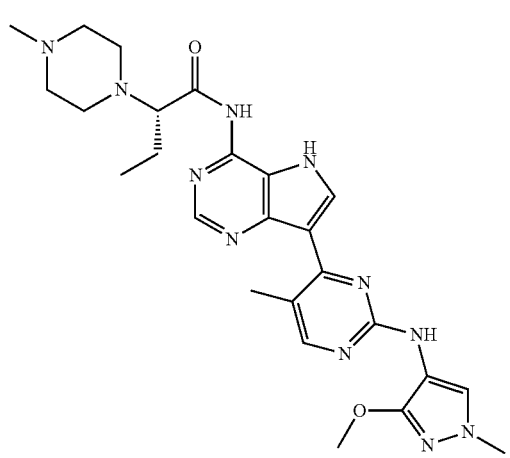
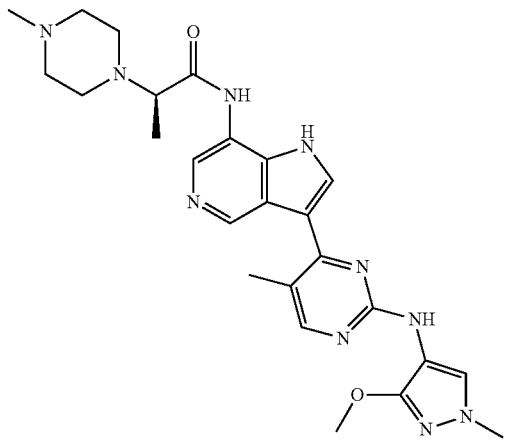
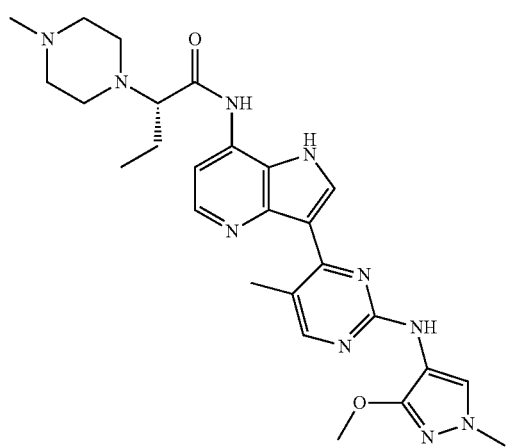
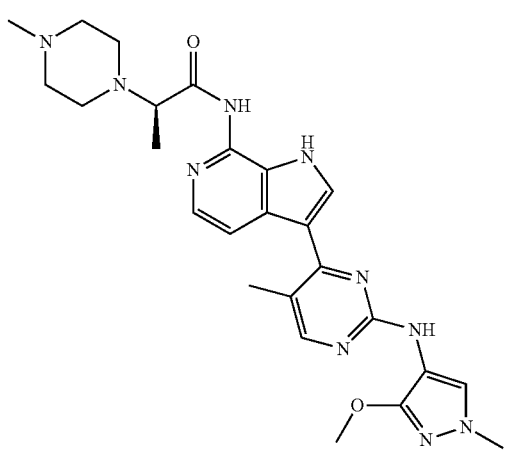

21
-continued
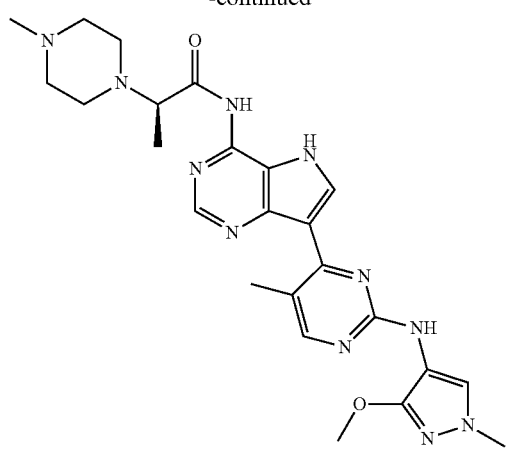
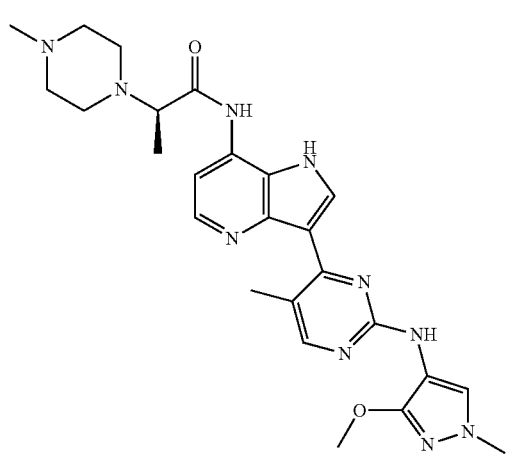
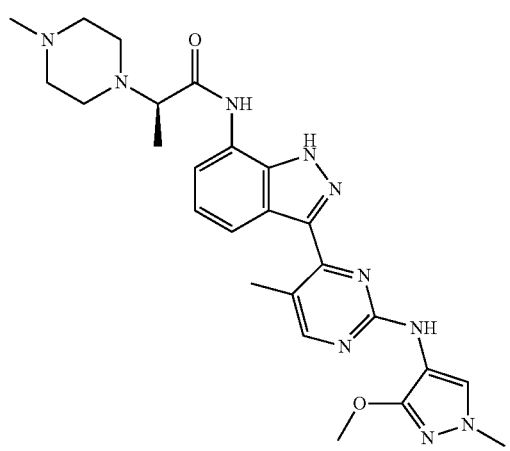
22
-continued
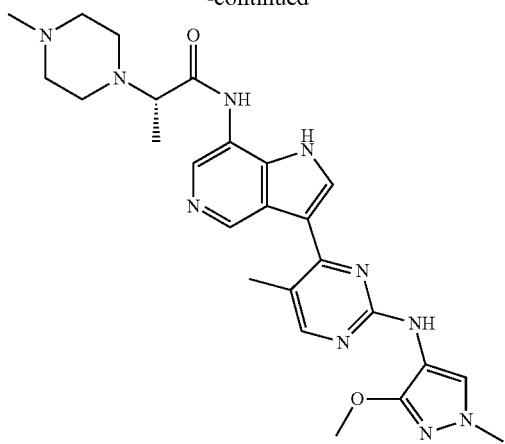
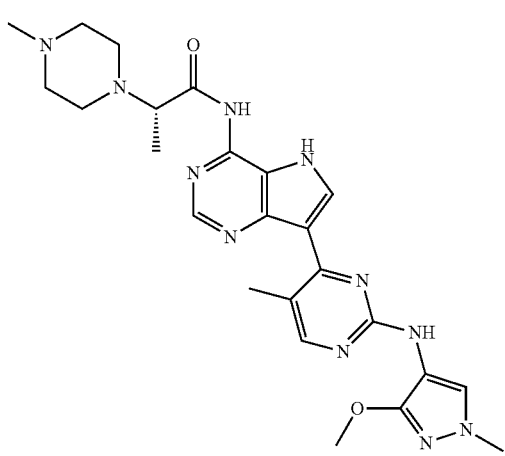

-continued
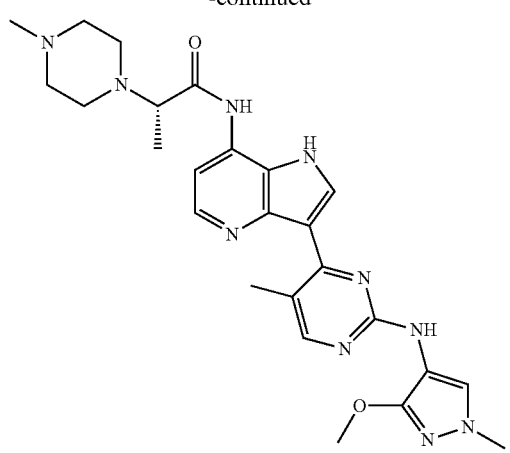
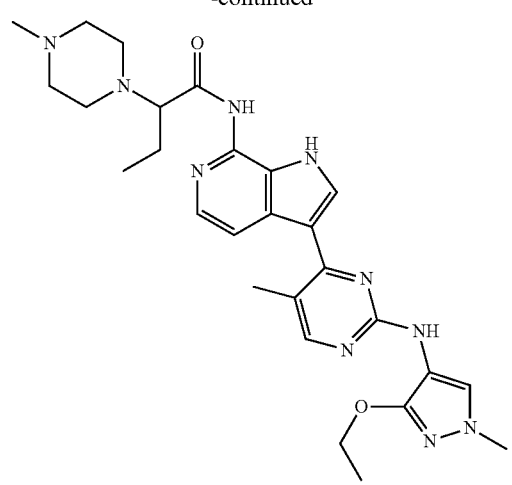
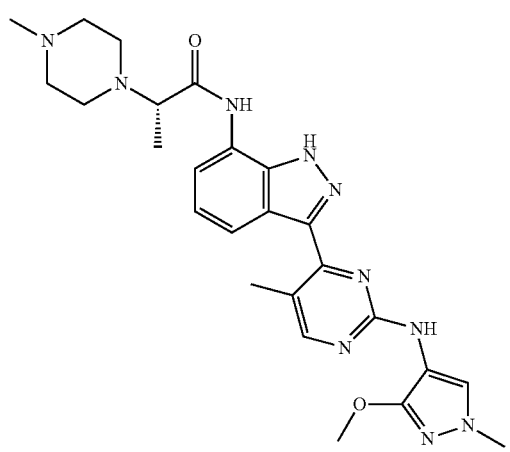
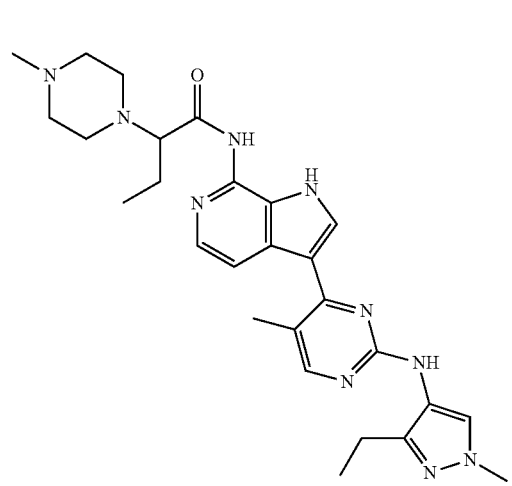
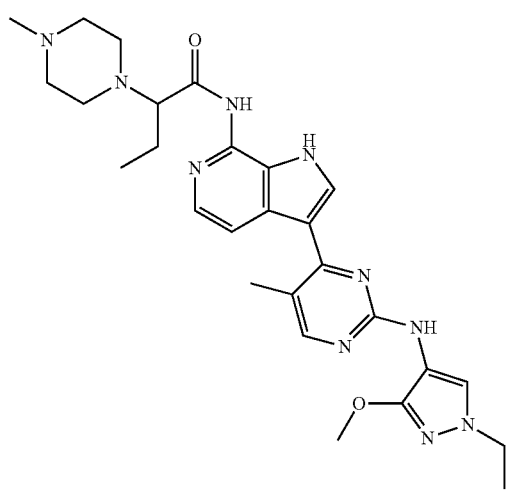
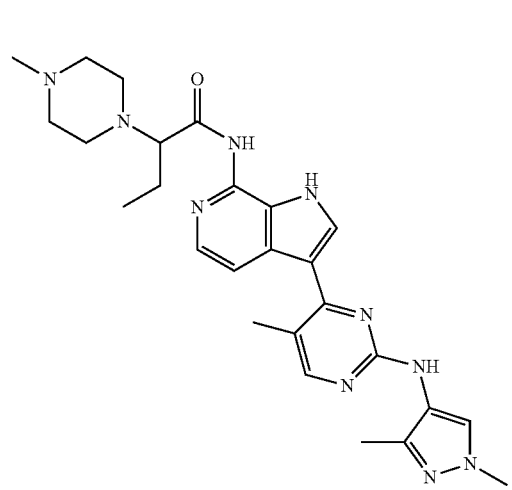

25
-continued
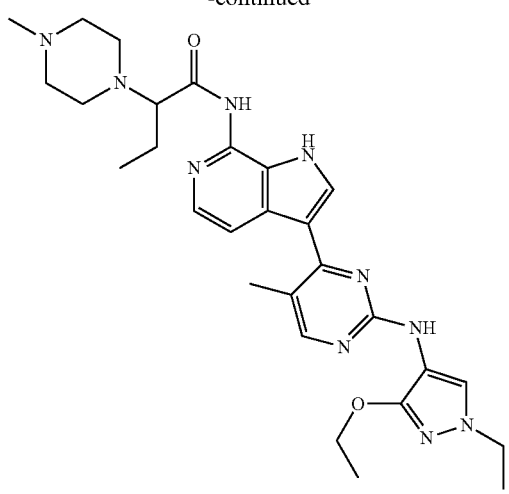
26
-continued
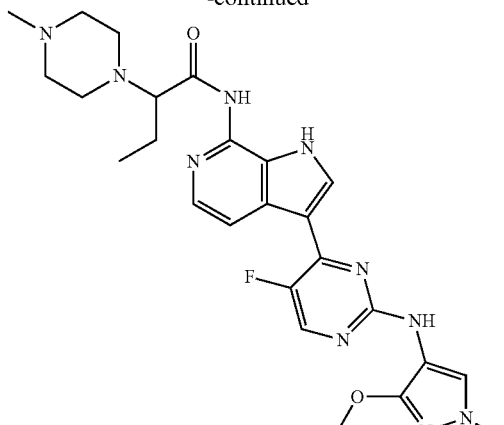
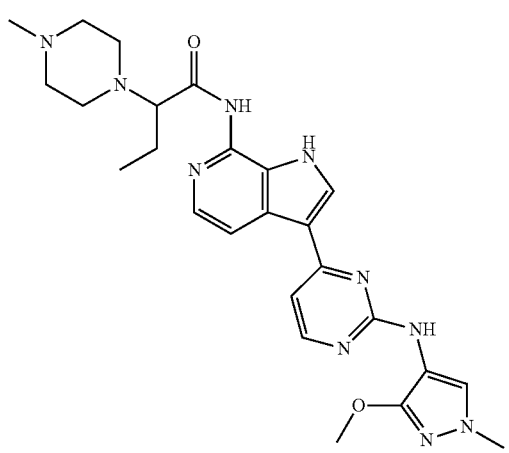
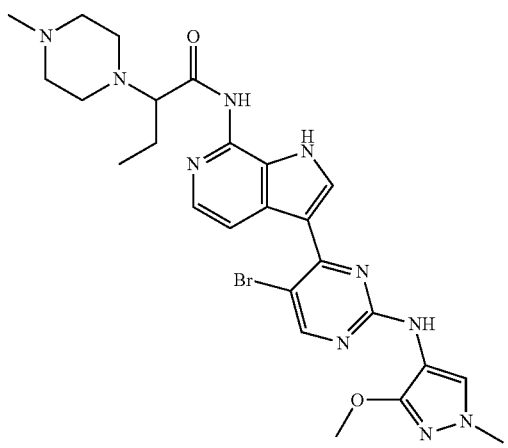
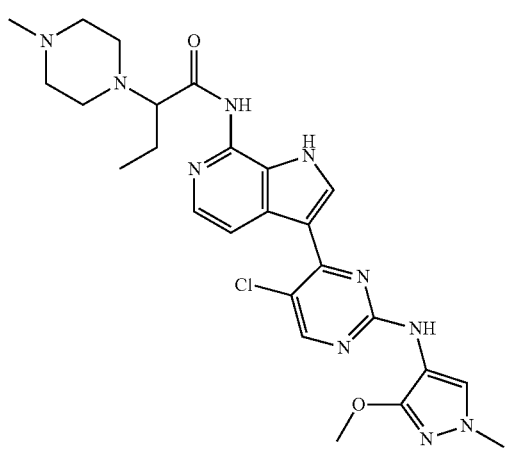
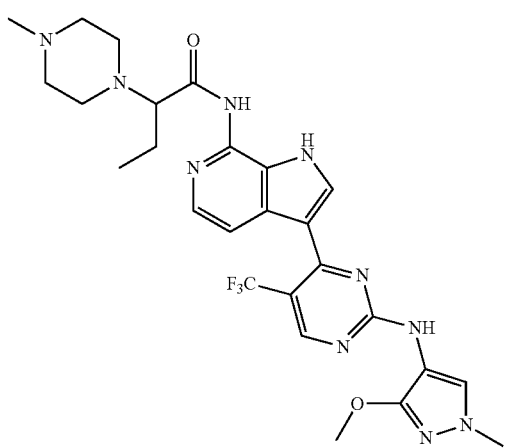

27
-continued
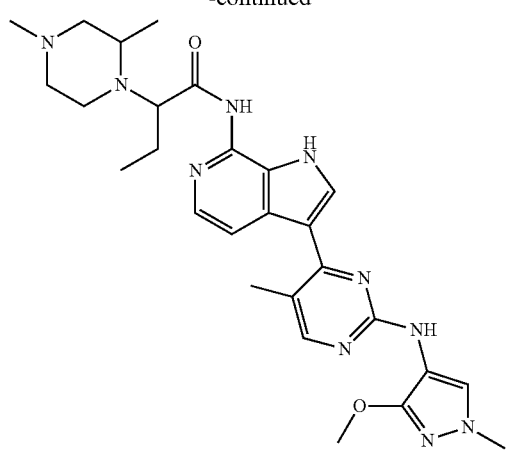
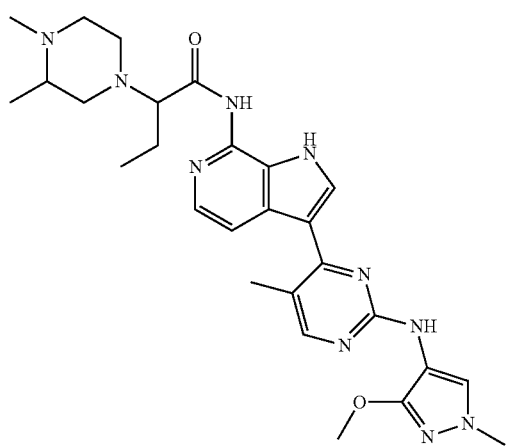
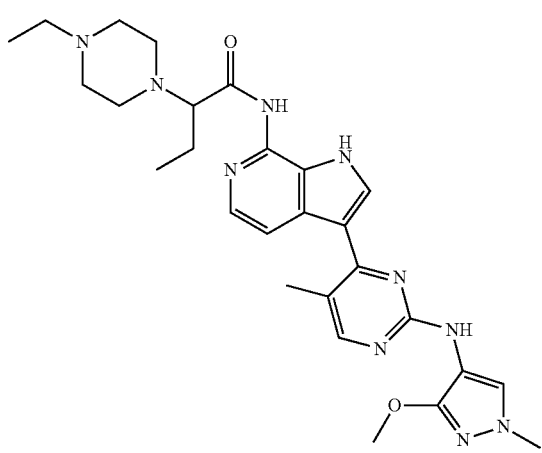
28
-continued
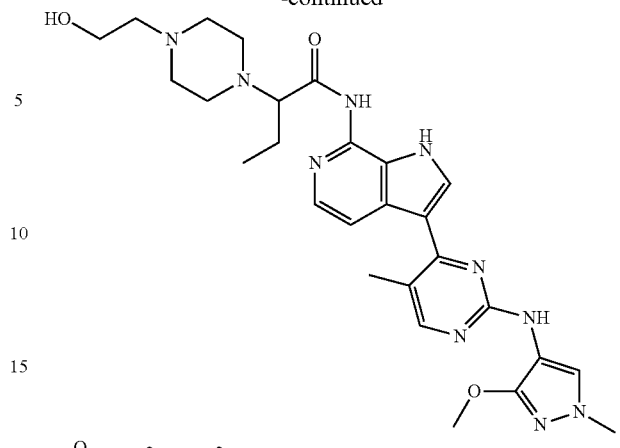
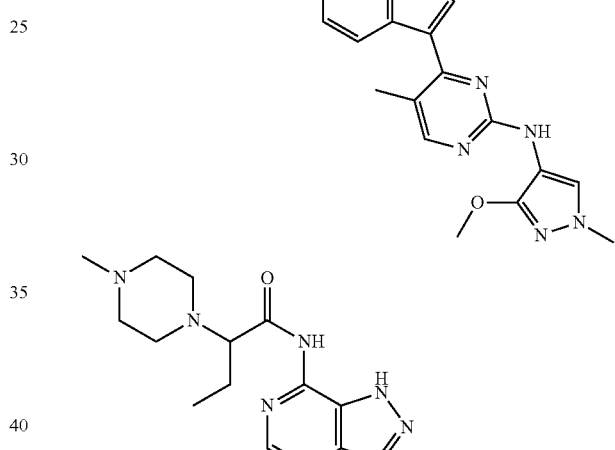
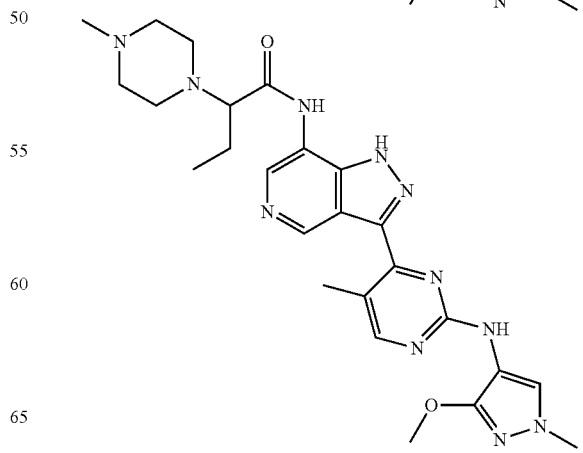

-continued
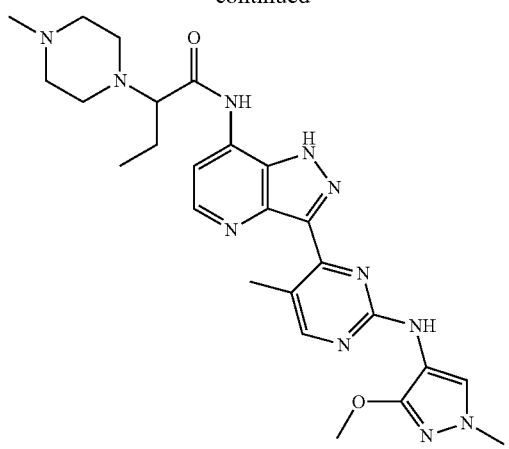
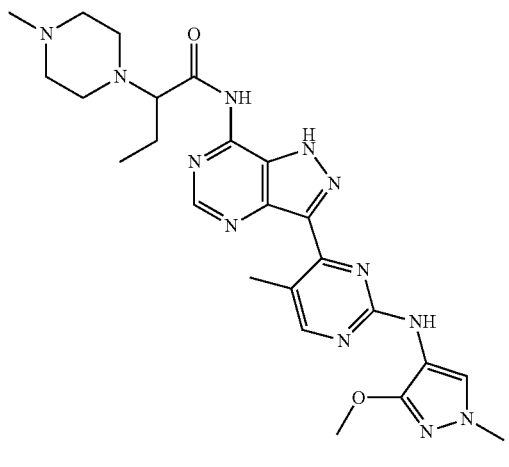
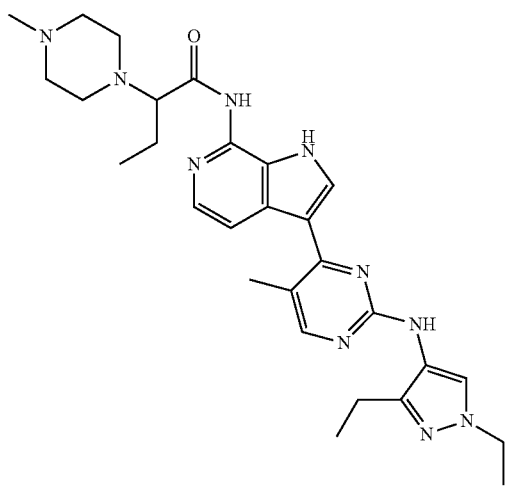
-continued
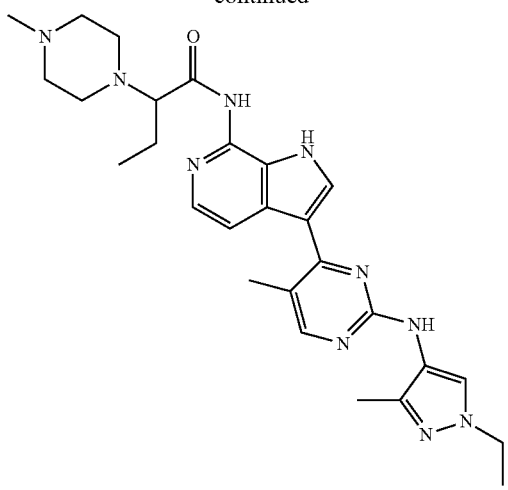
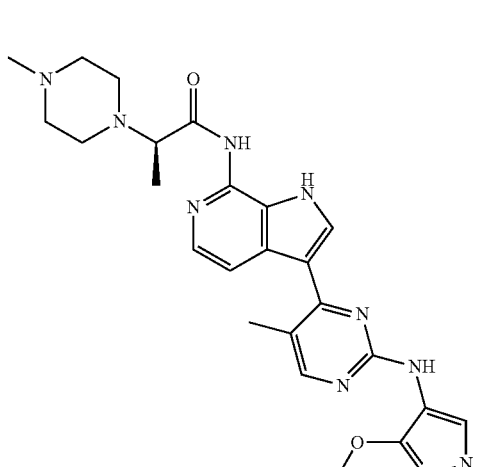
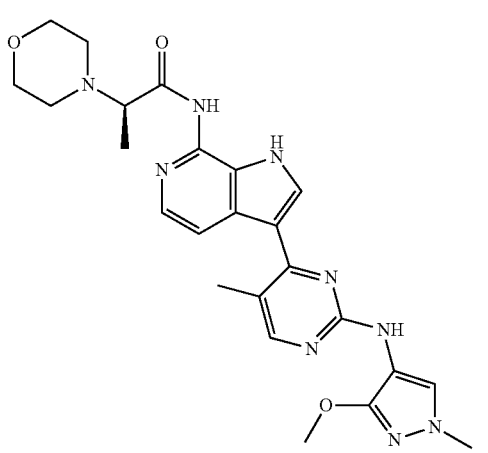

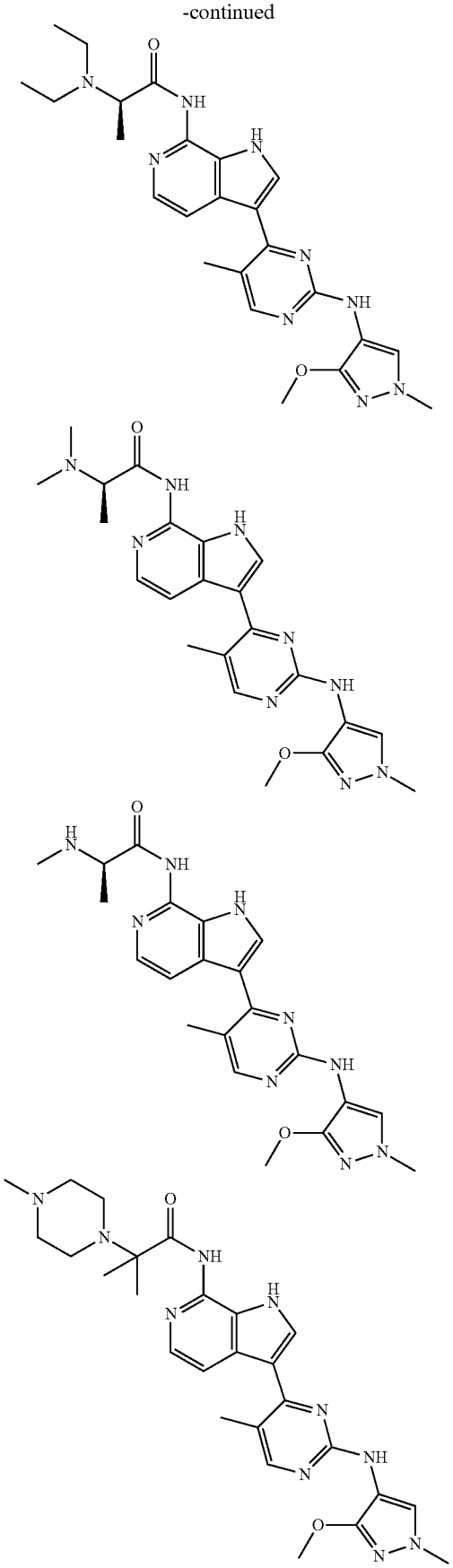
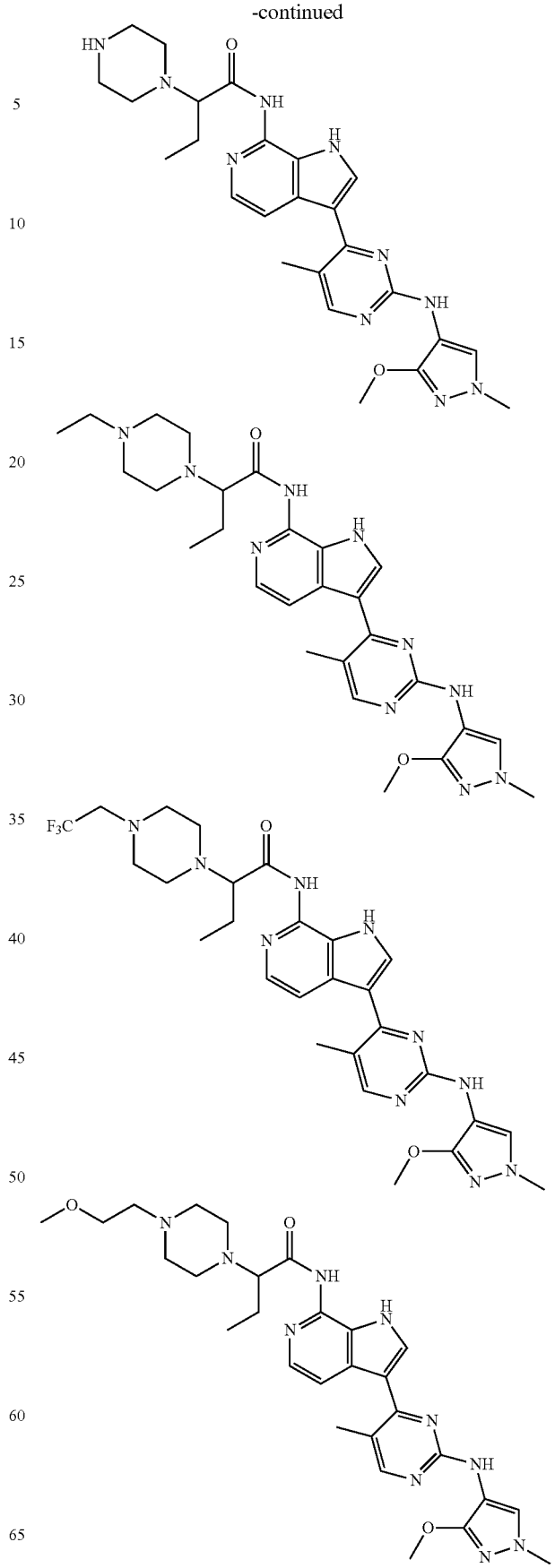

33
-continued
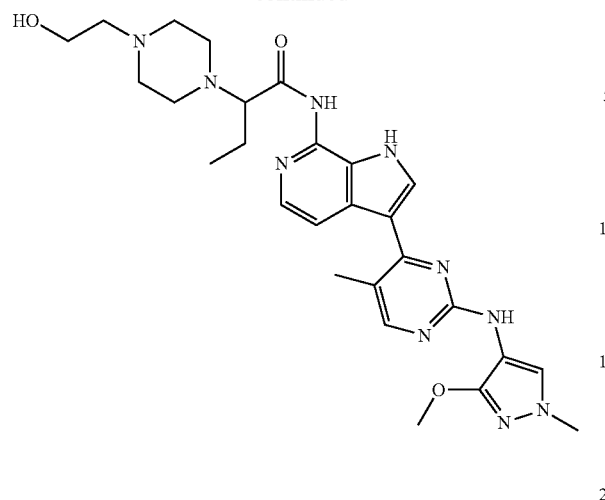
34
-continued
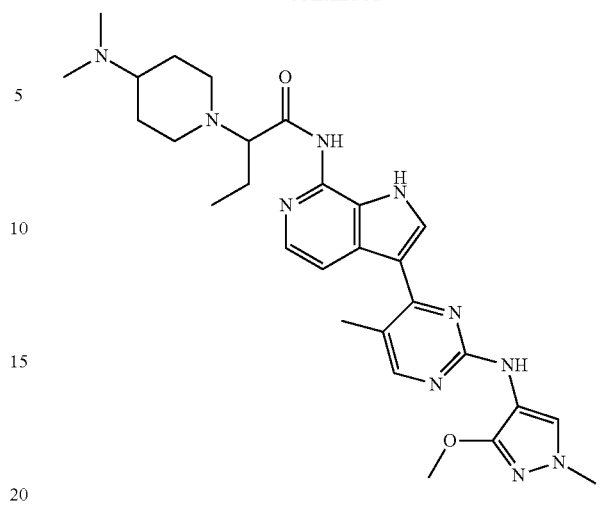
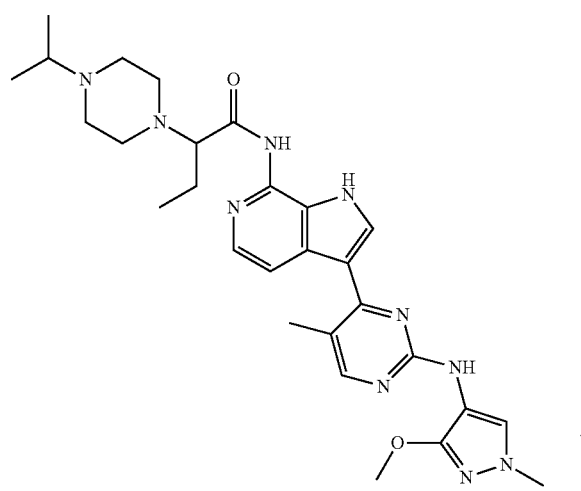
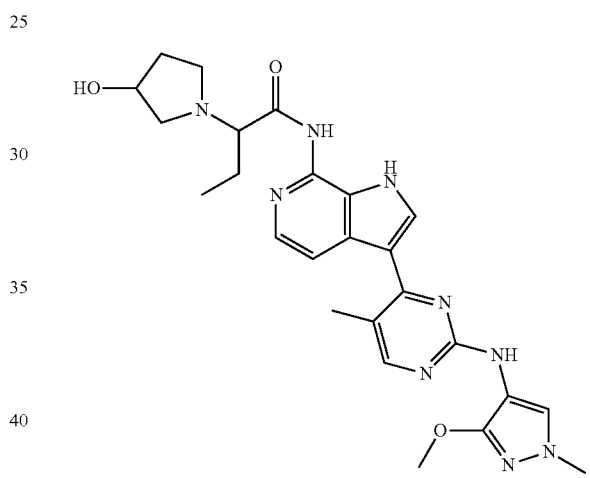
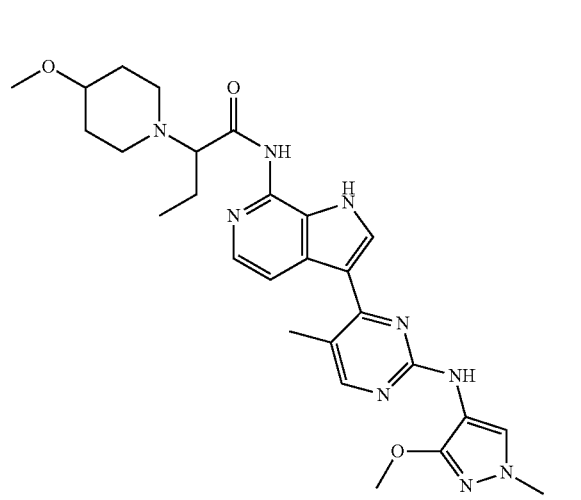
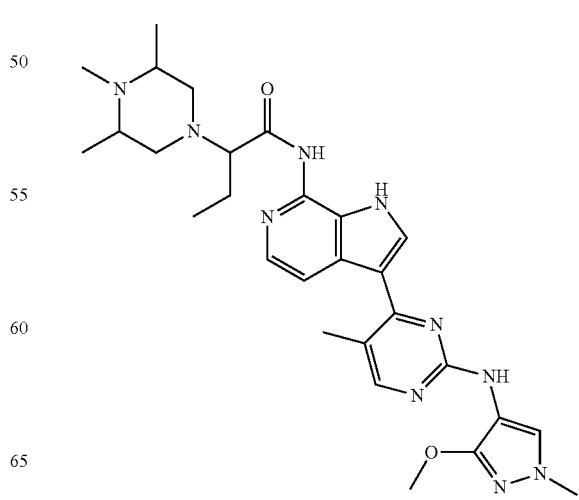

-continued
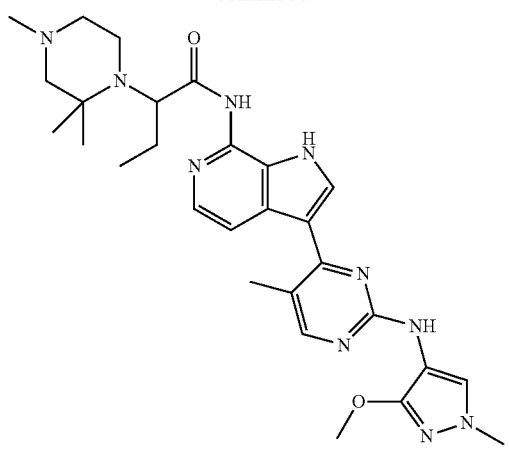
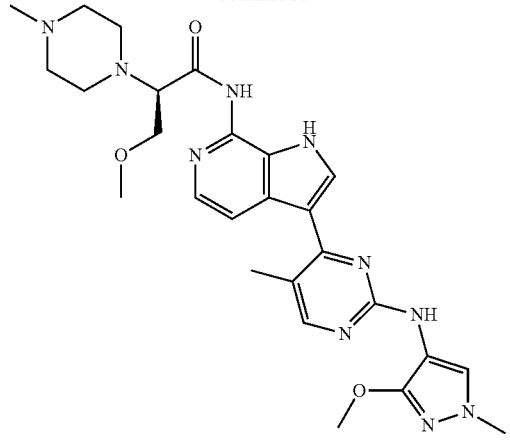
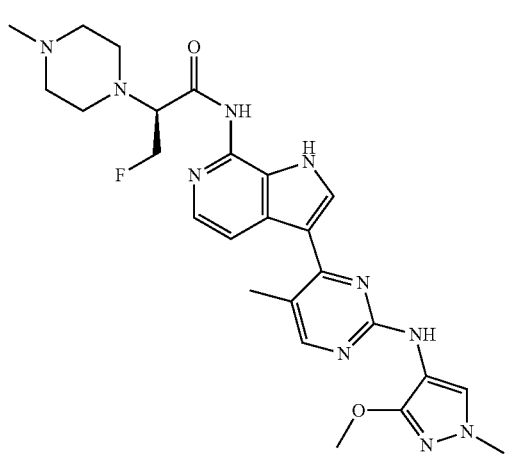
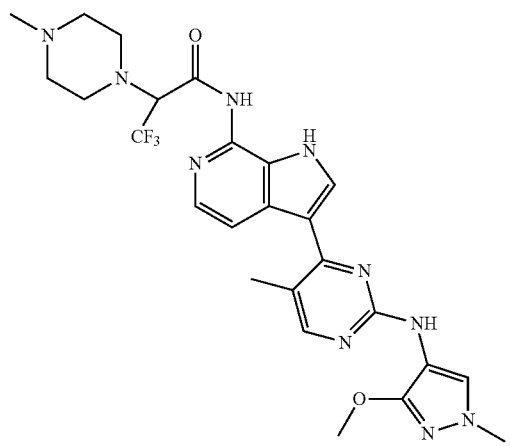
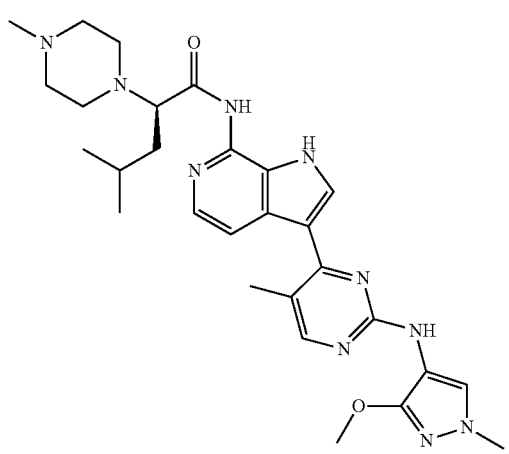
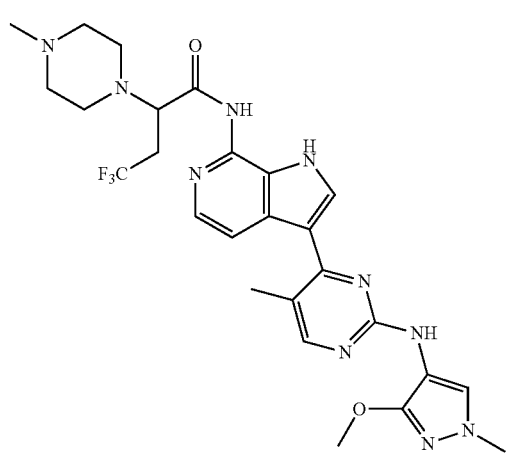

37
-continued
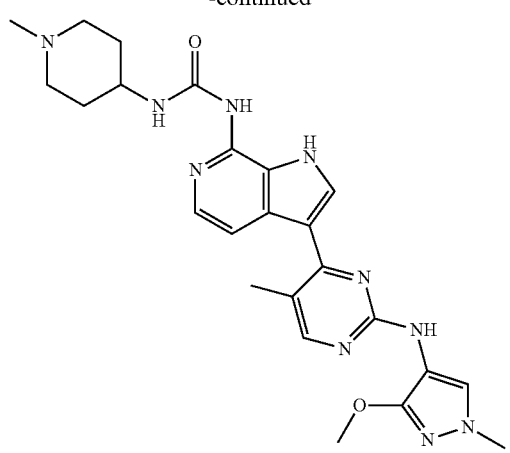
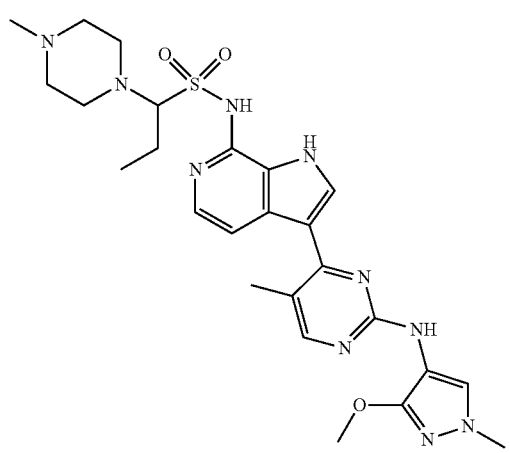
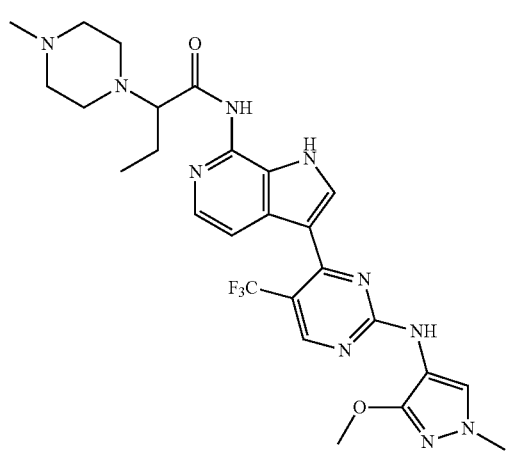
38
-continued
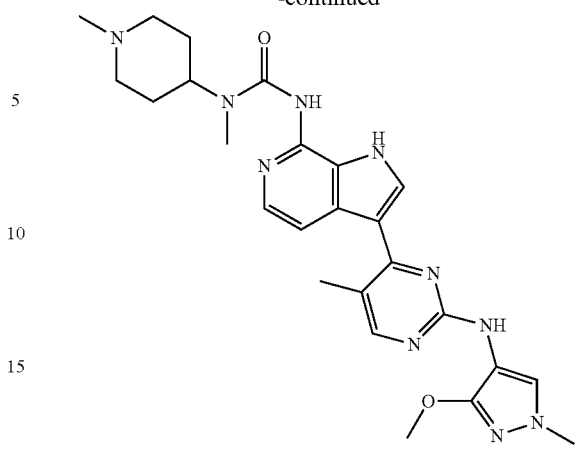
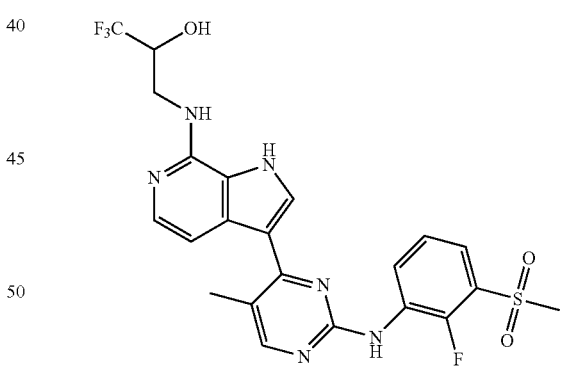
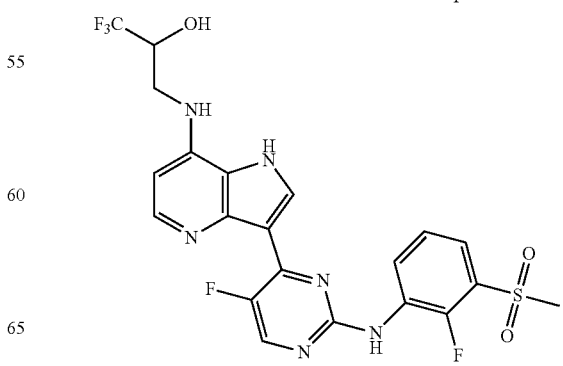

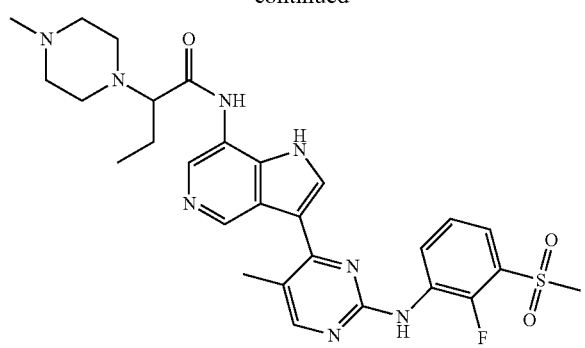
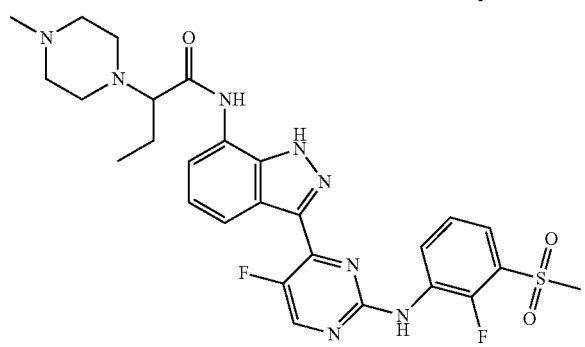
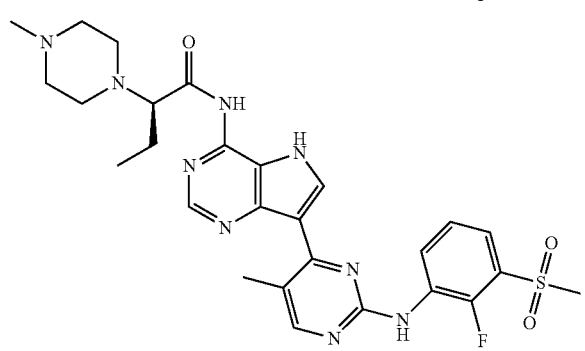
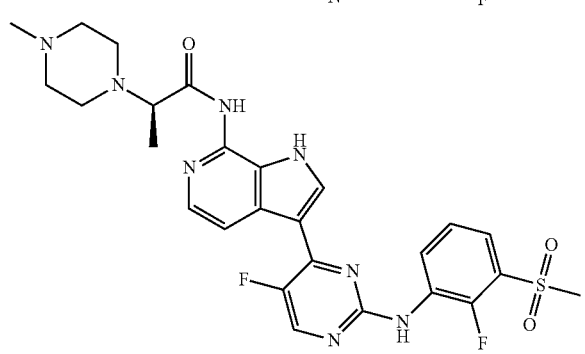
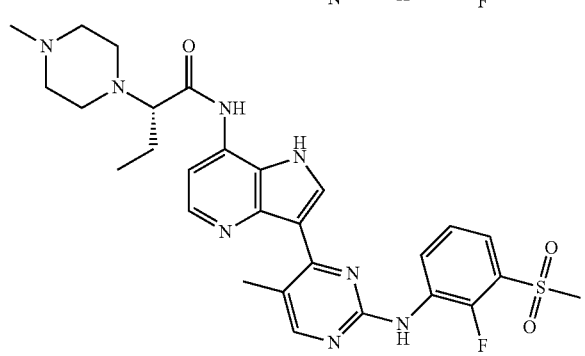
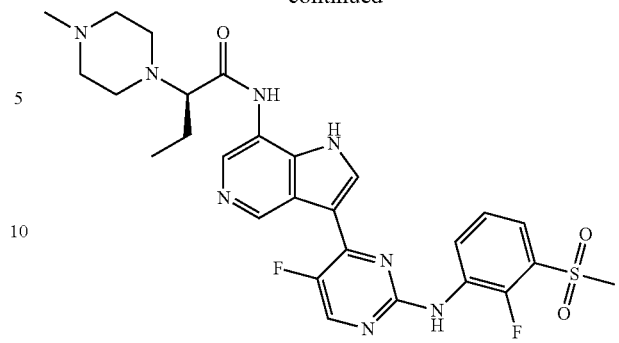
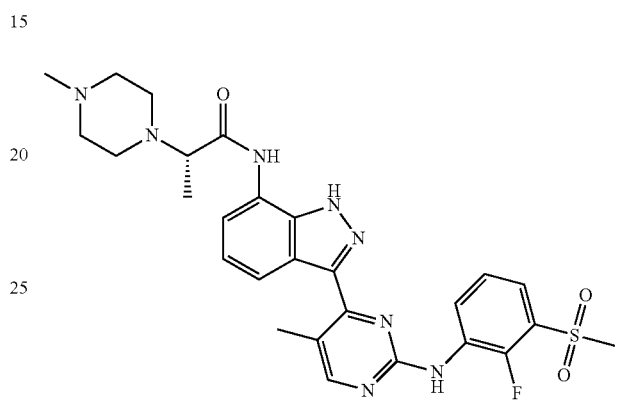
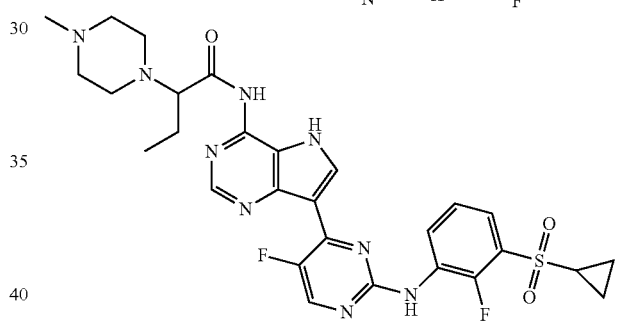
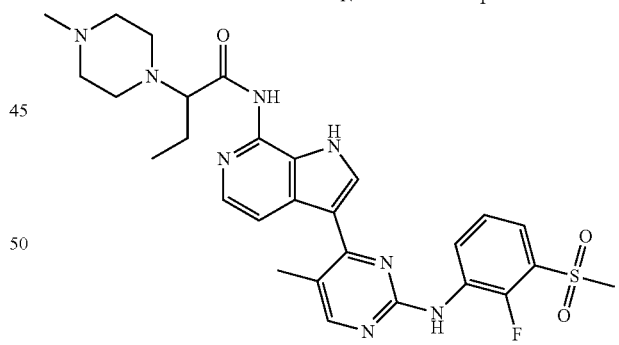
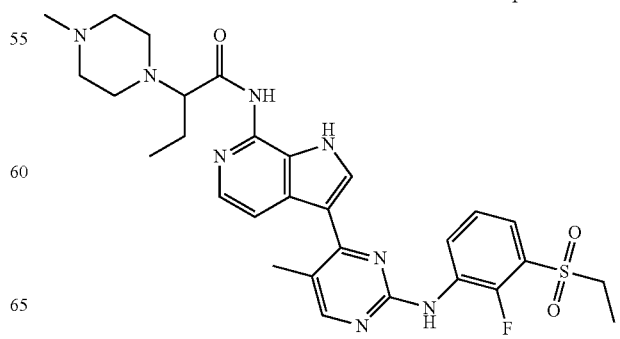

-continued
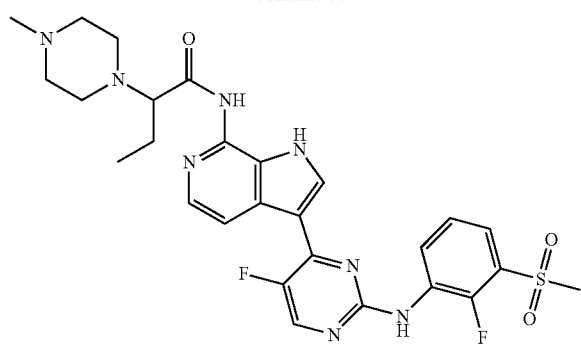
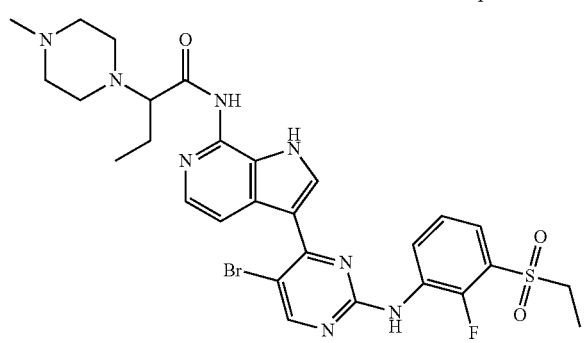
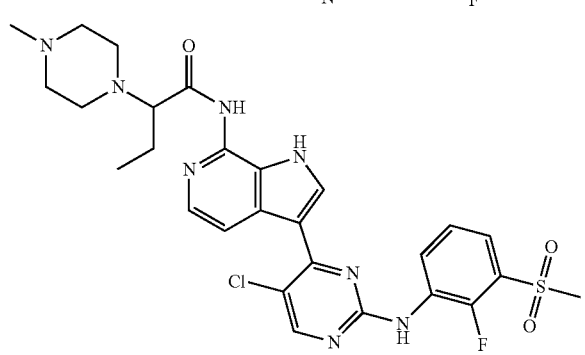
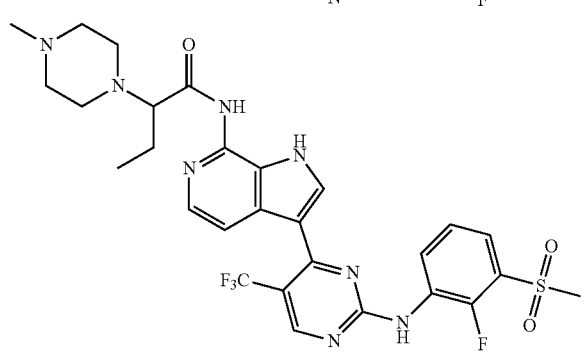
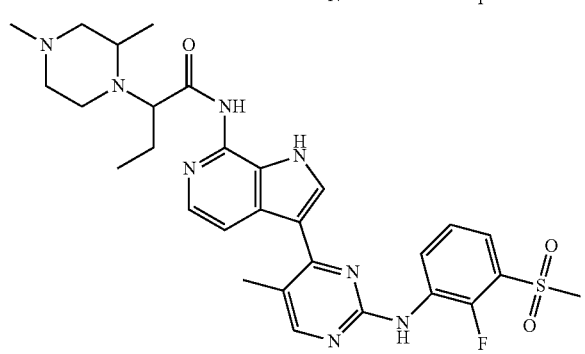
-continued
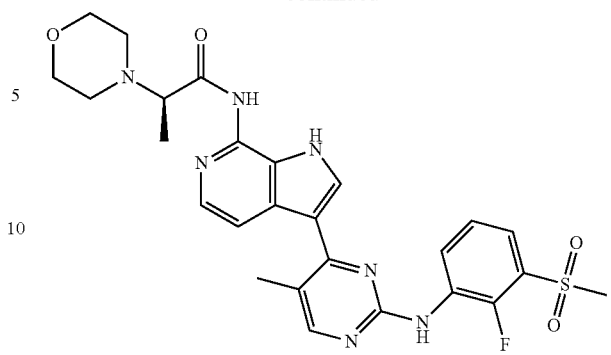
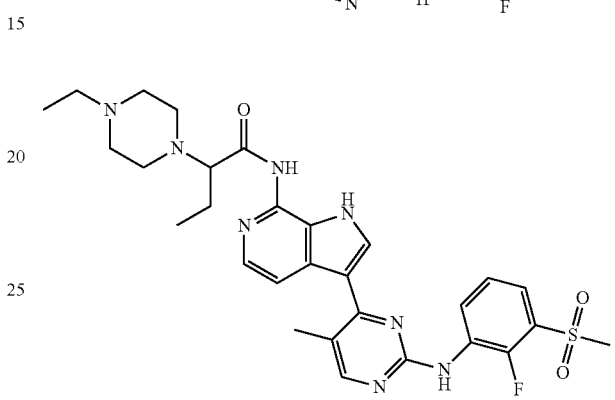
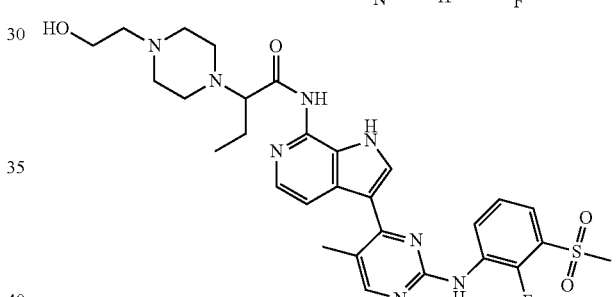
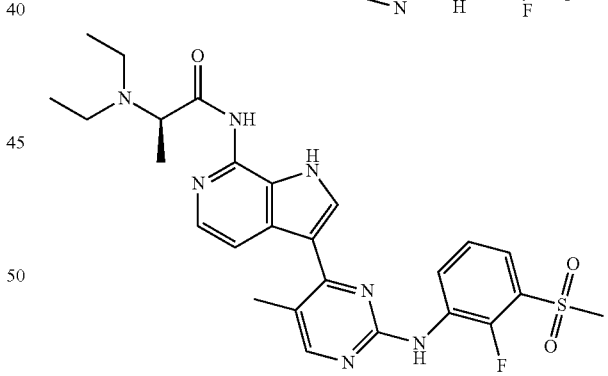
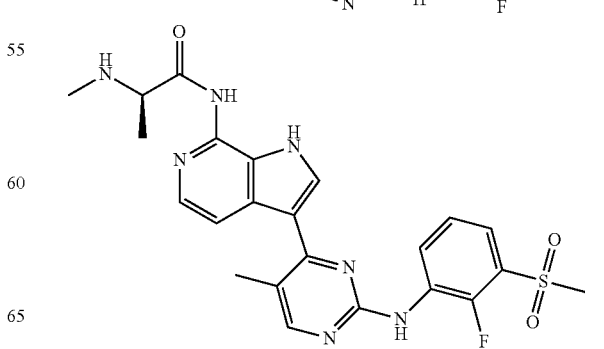

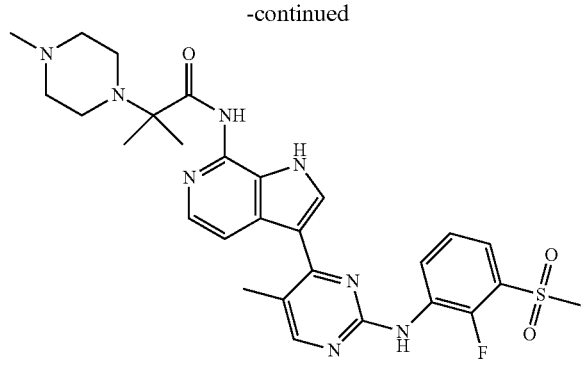
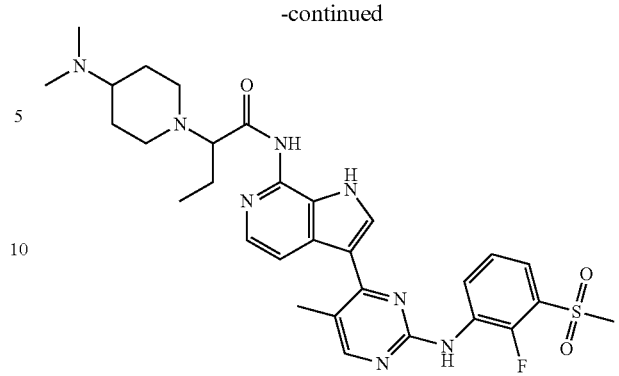
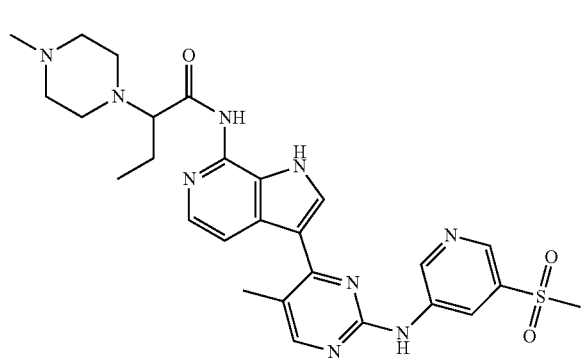
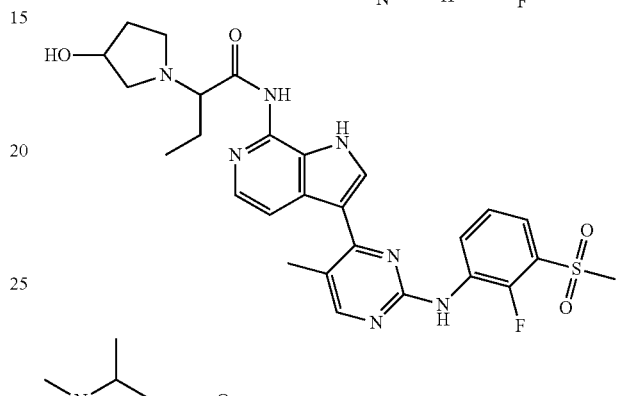
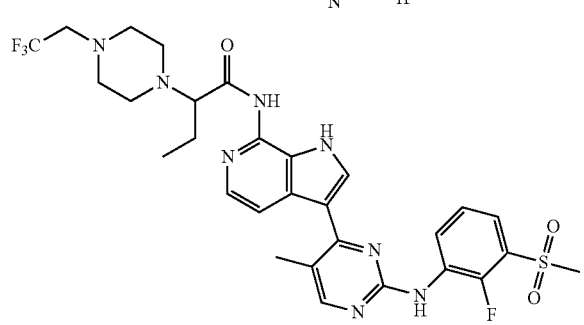
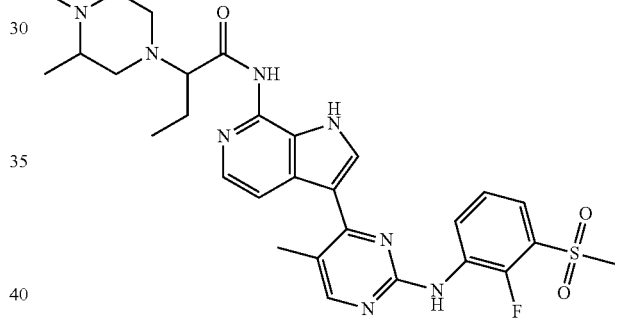
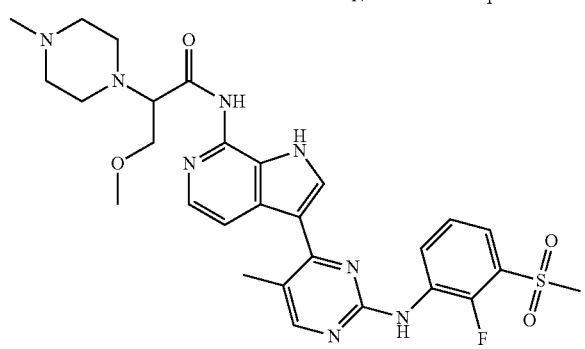
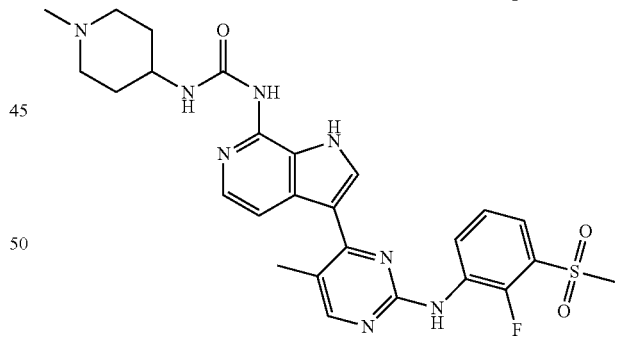
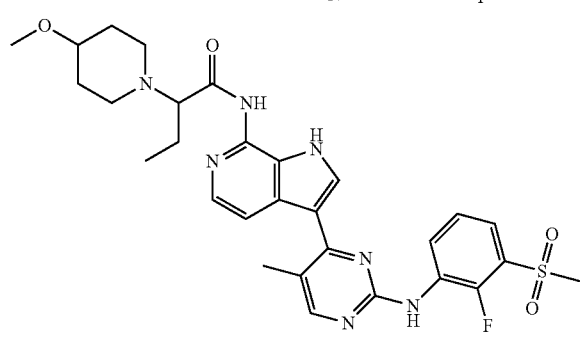
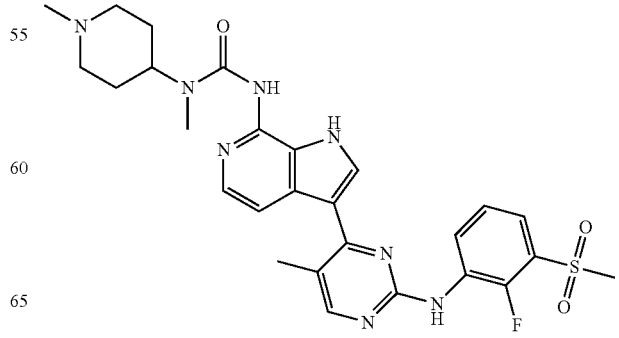

-continued
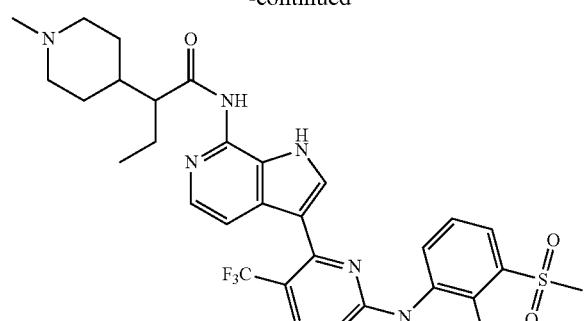
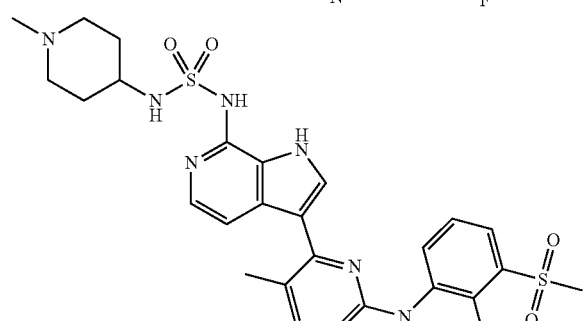
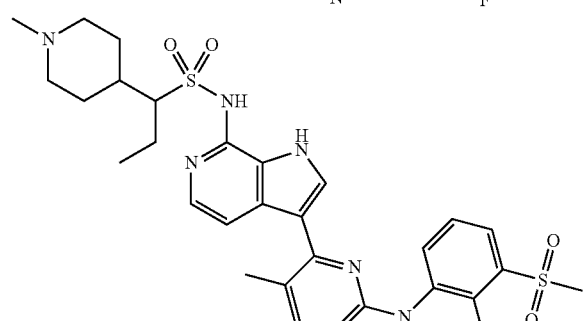
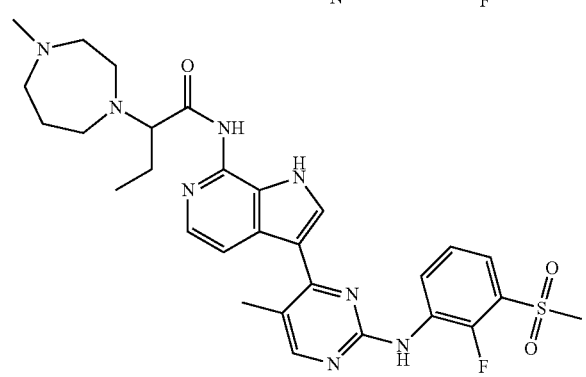
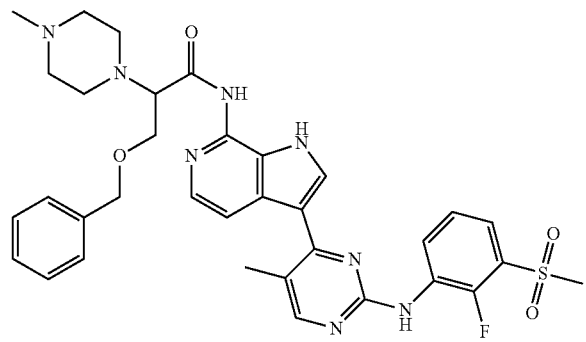
-continued
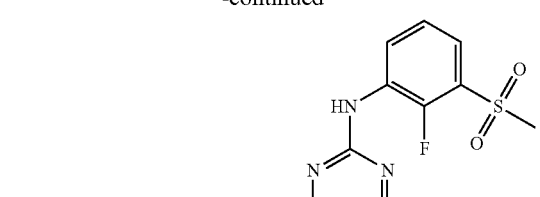
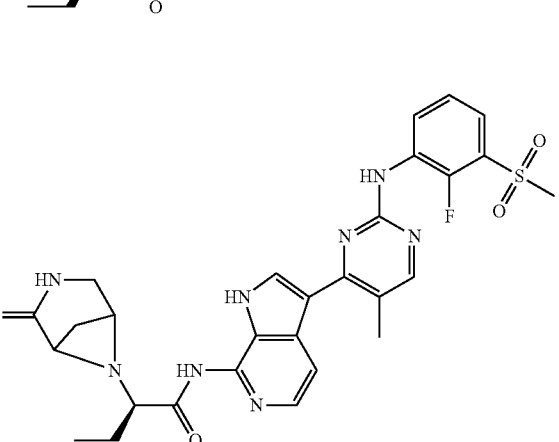
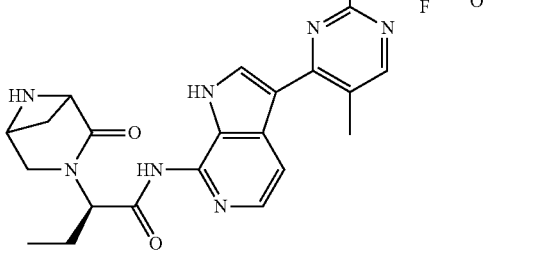
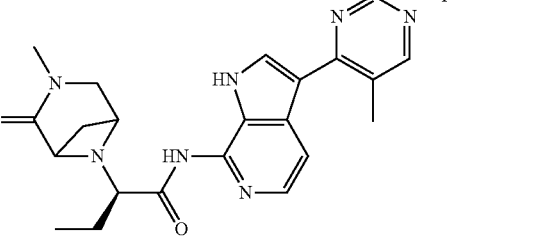

47
-continued
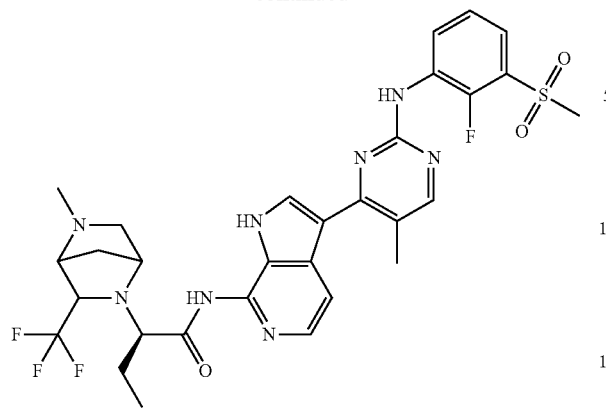
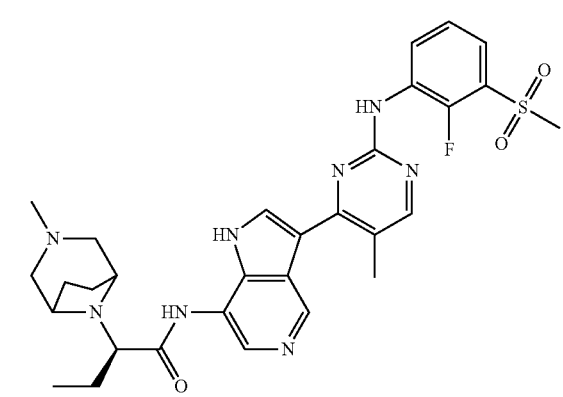
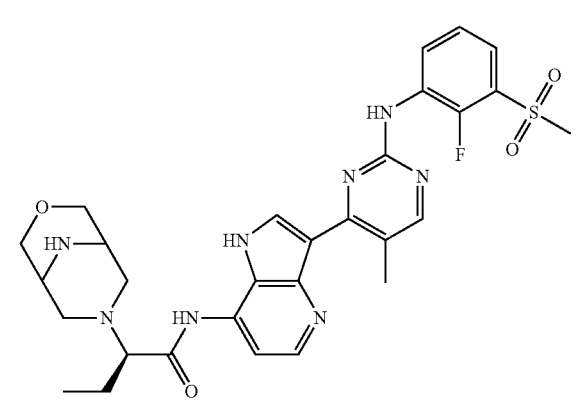
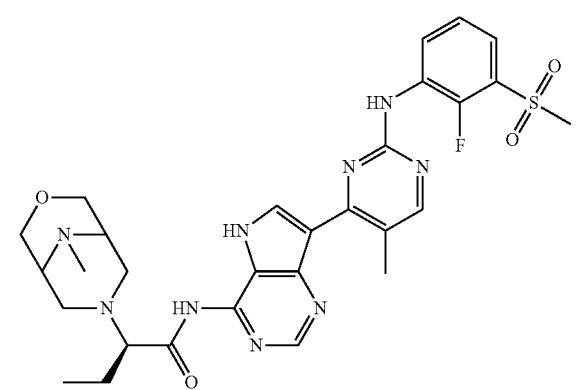
48
-continued
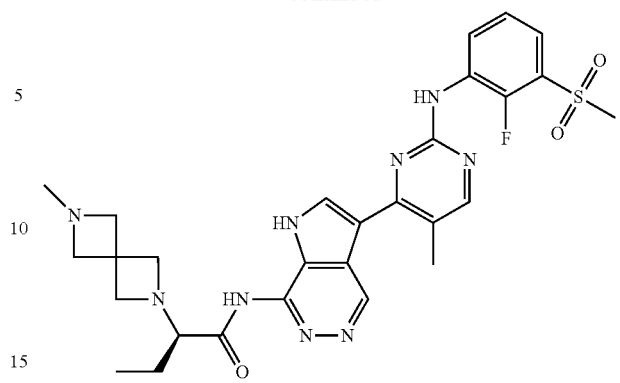
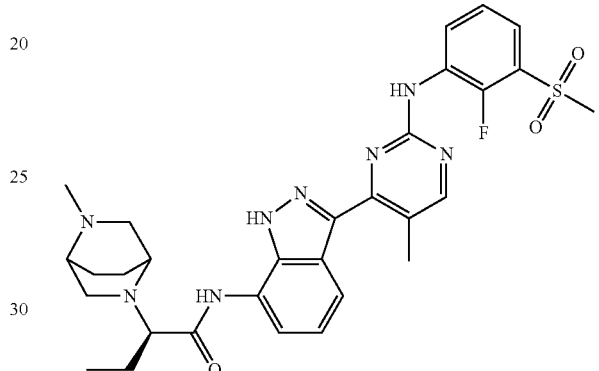
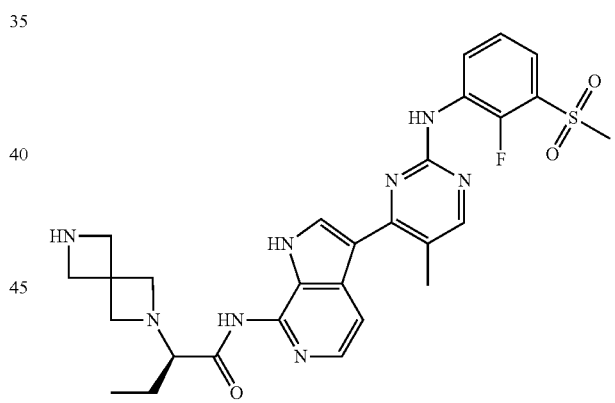
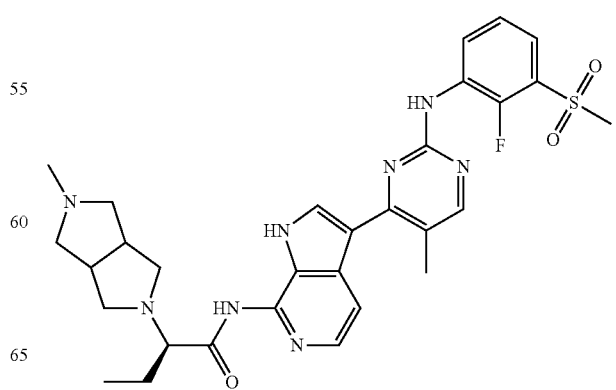

49
-continued
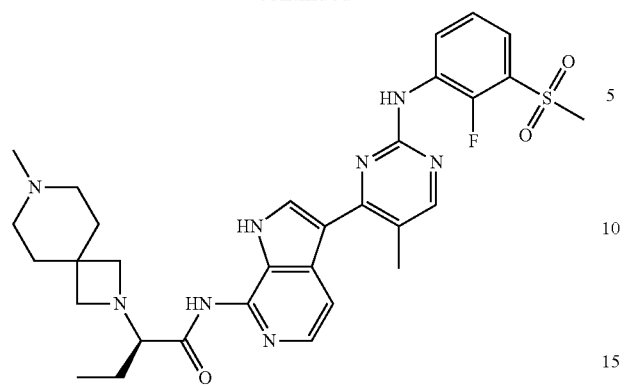
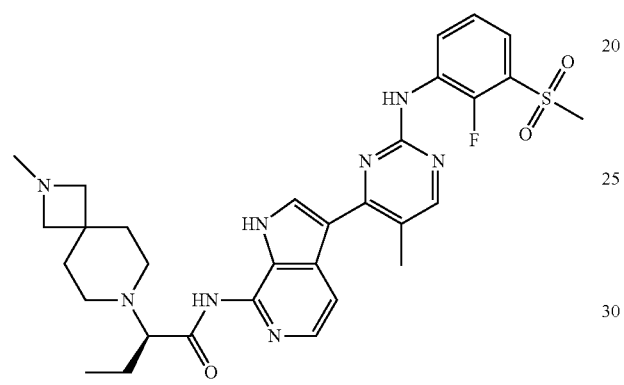
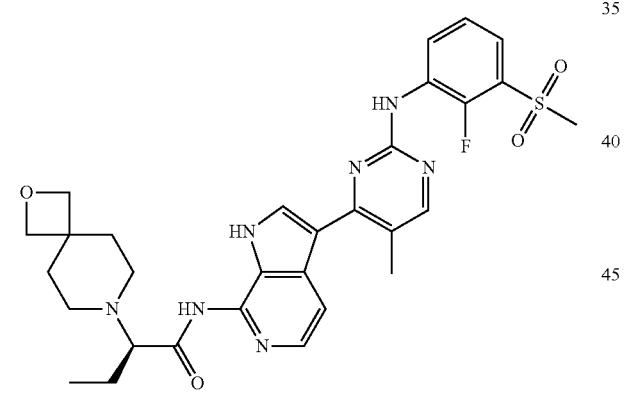
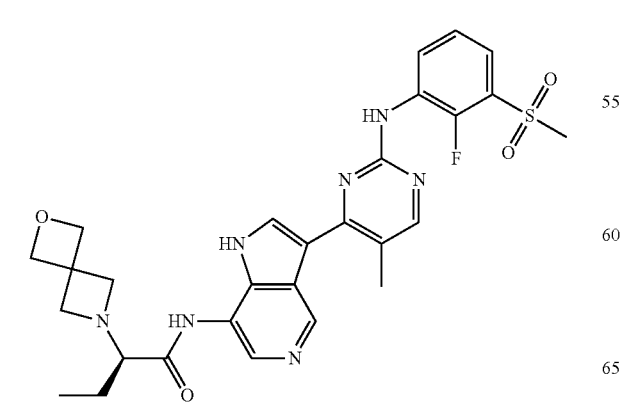
50
-continued
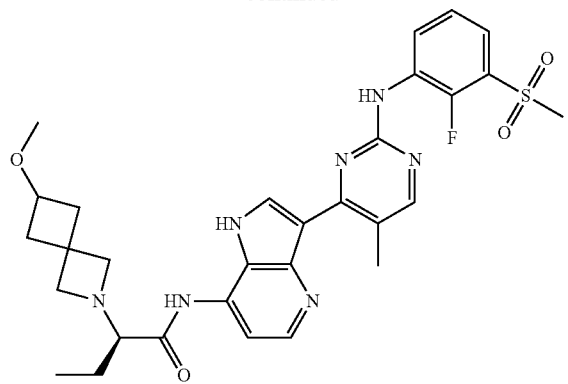
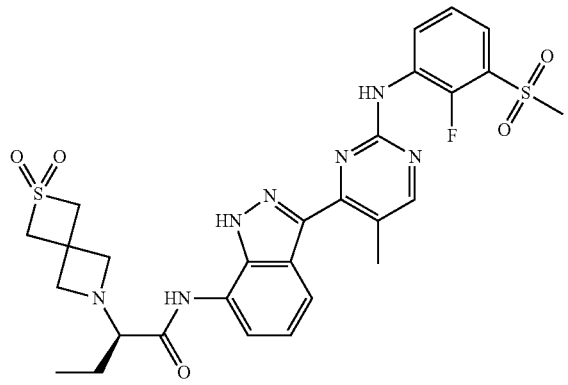
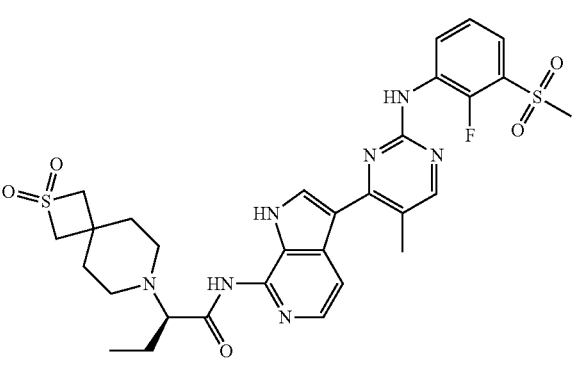
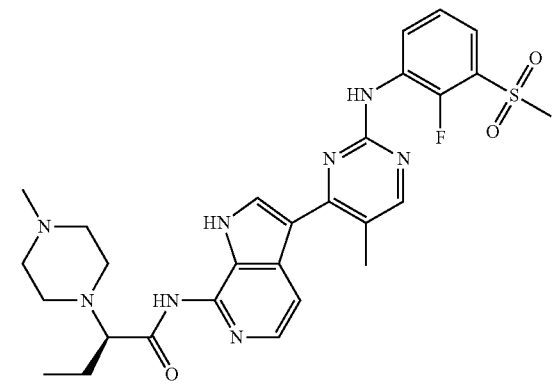

51
-continued
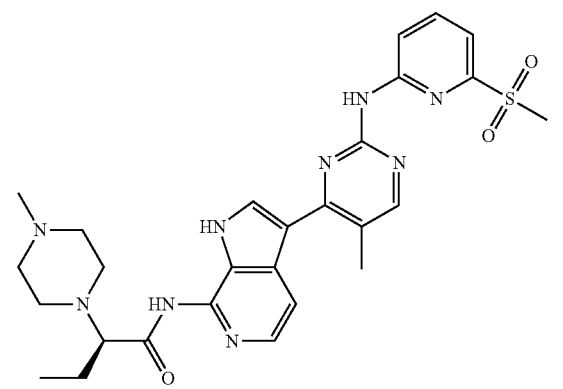
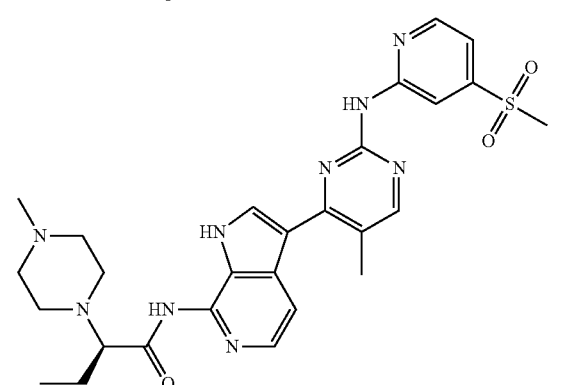
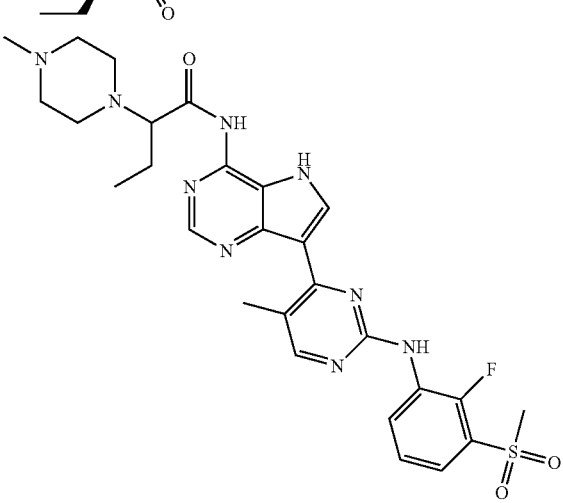
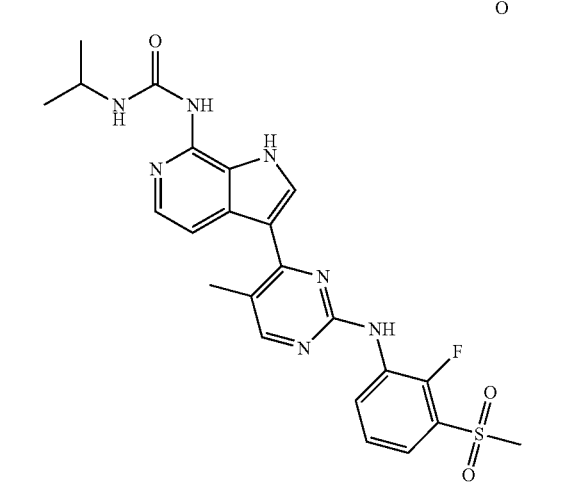
52
-continued
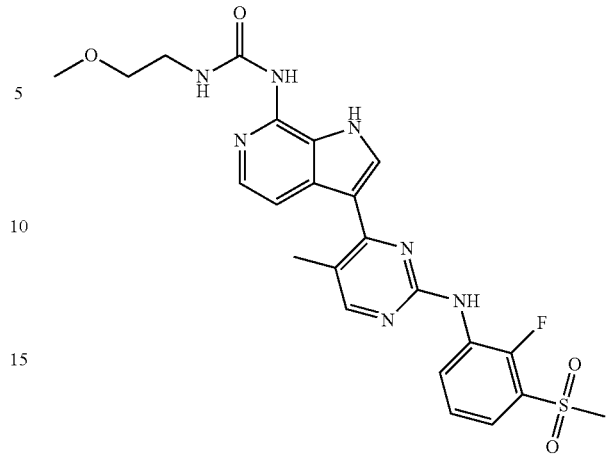
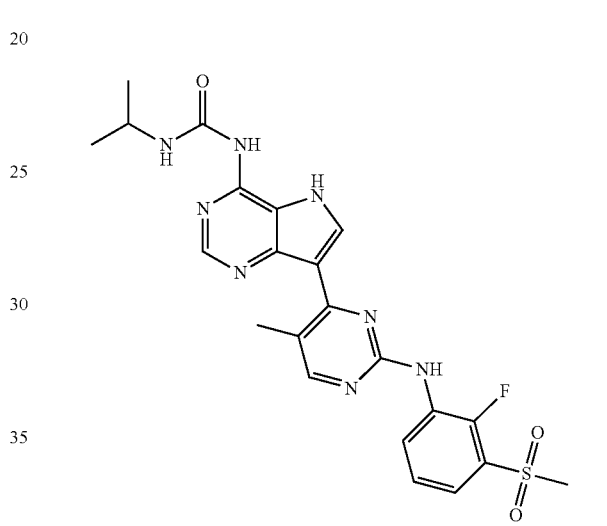
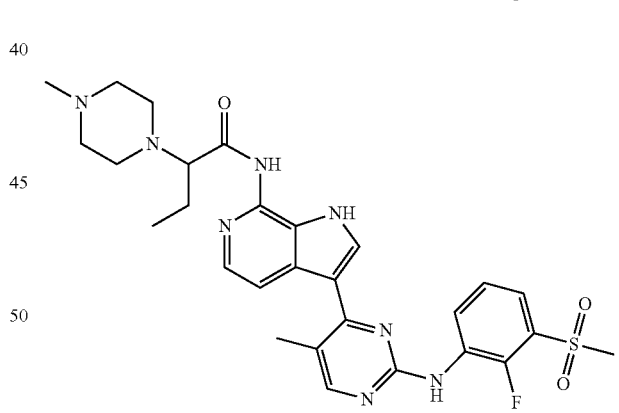
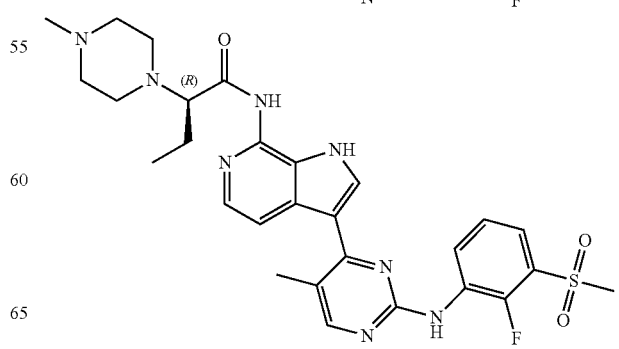

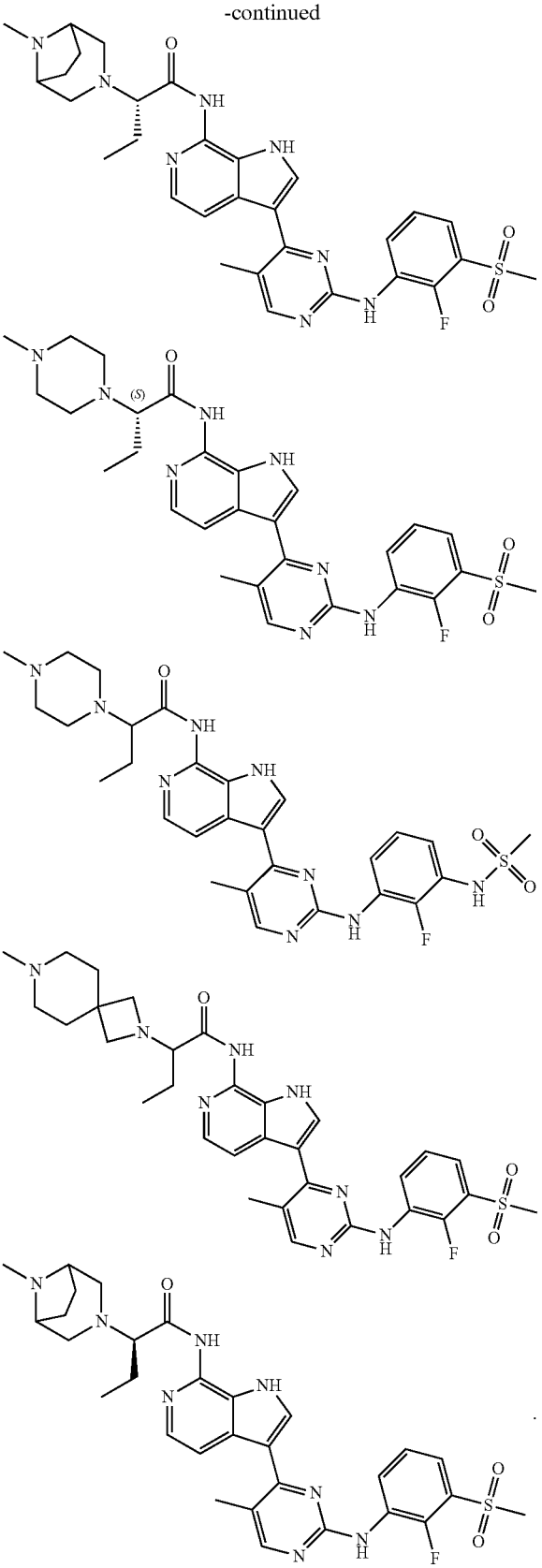

In the second aspect of the present invention, a pharmaceutical composition is provided, comprising: (1) the compound according to the first aspect of the present invention or stereoisomers or tautomers thereof, or pharmaceutically acceptable salts, hydrates or solvates thereof; (2) a pharmaceutically acceptable carrier.

In another preferred example, the pharmaceutical composition is injection, capsule, tablet, pill, pulvis or granule.

In another preferred example, the pharmaceutical composition also contains additional therapeutic drugs, and the additional therapeutic drugs are medicines for cancers, cardiovascular diseases, inflammation, immune diseases, myeloproliferative diseases, viral diseases, metabolic diseases, or organ transplant.

More preferably, the additional therapeutic drugs include (but are not limited to): 5-fluorouracil, Avastin™ (avastin, bevacizumab), bexarotene, bortezomib, calcitriol, canertinib, capecitabine, carboplatin, celecoxib, cetuximab, cisplatin, dasatinib, digoxin, enzastaurin, erlotinib, etoposide, everolimus, fulvestrant, gefitinib, 2,2-difluorodeoxycytidine (gemcitabine), genistein, imatinib, irinotecan, lapatinib, lenalidomide, letrozole, leucovorin, matuzumab, oxaliplatin, paclitaxel, panitumumab, pegfdgrastin, peglated alfa-interferon, pemetrexed, Polyphenon® E, satraplatin, sirolimus, (sutent, sunitinib), sulindac, taxotere, (temodar, temozomolomide), Torisel, temsirolimus, tipifamib, trastuzumab, valproic acid, vinflunine, Volociximab, Vorinostat, Sorafenib, ambrisentan, CD40 and/or CD154 specific antibodies, fusion proteins, NF-kB inhibitors, non-steroidal anti-inflammatory drugs, β-agonists such as salmeterol, coagulation factor FXa inhibitors (such as rivaroxaban, etc.), anti-TNF antibodies, prostaglandin drugs or montelukast.

In the third aspect of the present invention, the use of the compound according to the first aspect of the present invention or stereoisomers or tautomers thereof, or pharmaceutically acceptable salts, hydrates or solvates thereof, or the pharmaceutical composition according to the second aspect of the present invention is provided, which is used for preparing a pharmaceutical composition for preventing and/or treating diseases related to the activity or expression of JAK kinase.

In another preferred example, the diseases are selected from the group consisting of cancers, cardiovascular diseases, inflammation, immune or inflammatory diseases, myeloproliferative diseases, viral diseases, metabolic diseases, or organ transplant.

In another preferred example, the cancers (but are not limited to) are selected from the group consisting of non-small cell lung cancer, uterine cancer, rectal cancer, colon cancer, brain cancer, head cancer, neck cancer, bladder cancer, prostate cancer, breast cancer, kidney cancer, blood cancer, liver cancer, stomach cancer, thyroid cancer, nasopharyngeal cancer, or pancreatic cancer.

In another preferred example, the myeloproliferative diseases include (but are not limited to): essential thrombocythemia (ET), idiopathic myelofibrosis (IMF), chronic myelogenous leukemia (CML), primary myelofibrosis, chronic neutrophil leukemia (CNL) or polycythemia vera (PV).

In another preferred example, the immune or inflammatory diseases include (but are not limited to): rheumatoid arthritis, osteoarthritis, rheumatoid spondylitis, gout, asthma, bronchitis, rhinitis, chronic obstructive pulmonary disease, pulmonary fibrosis, cystic fibrosis, enteritis.

In another preferred example, the metabolic diseases include (but are not limited to): type II diabetes, type I diabetes, diabetic complications (such as diabetic nephropathy, diabetic retinopathy, non-alcoholic steatohepatitis, hepatic fibrosis, insulin resistance, obesity).

In the fourth aspect of the present invention, a JAK inhibitor is provided, wherein the inhibitor comprises the compound according to the first aspect of the present invention, or stereoisomers or tautomers thereof, or pharmaceutically acceptable salts, hydrates or solvates thereof.

In another preferred example, the JAK inhibitor selectively inhibits one or more JAK kinases selected from the group consisting of JAK1, JAK2, JAK3 or Tyk2.

In another preferred example, the JAK inhibitor is a highly selective JAK1 inhibitor.

It should be understood that, within the scope of the present invention, the above-mentioned technical features herein and the technical features specifically described in the following (such as the examples) can be combined with each other, thereby constituting new or preferred technical solutions which need not be specified again herein.

EMBODIMENTS FOR CARRYING OUT THE INVENTION

The inventor designed and synthesized a novel JAK kinase inhibitor after long-term and in-depth research. The inventor completed the present invention on this basis.

Terms

Unless otherwise defined, all technical and scientific terms used herein have the same meaning as commonly understood by one of ordinary skill in the art to which this invention belongs.

As used herein, when used in reference to a specifically recited value, the term "about" means that the value can vary by no more than 1% from the recited value. For example, as used herein, the expression "about 100" includes all values between 99 and 101 (e.g., 99.1, 99.2, 99.3, 99.4, etc.).

As used herein, the terms "containing" or "comprising (including)" can be open form, semi-closed form, and closed form. In other words, the terms also include "substantially consisting of" or "consisting of".

Definitions

As used herein, the term "alkyl" includes straight or branched alkyl groups. For example, $C_1$-$C_8$ alkyl refers to straight or branched alkyls having 1-8 carbon atoms, such as methyl, ethyl, propyl, isopropyl, butyl, isobutyl, tert-butyl, and the like.

As used herein, the term "alkenyl" includes straight or branched alkenyl groups. For example, $C_2$-$C_6$ alkenyl refers to straight or branched alkenyl groups having 2-6 carbon atoms, such as vinyl, allyl, 1-propenyl, isopropenyl, 1-butenyl, 2-butenyl, and the like.

As used herein, the term "alkynyl" includes straight or branched alkynyl groups. For example, "$C_2$-$C_6$ alkynyl" refers to straight or branched alkynyls having 2-6 carbon atoms, such as ethynyl, propynyl, butynyl, and the like.

As used herein, the term "$C_3$-$C_8$ cycloalkyl" refers to cycloalkyl groups having 3 to 10 carbon atoms. It may be a monocyclic ring, such as cyclopropyl, cyclobutyl, cyclopentyl, cyclohexyl, and the like. It may also be of bicyclic form, such as bridged or spiro ring form.

As used herein, the term "$C_1$-$C_8$ alkoxyl" refers to straight or branched alkoxyl groups having 1-8 carbon atoms; for example, methoxy, ethoxy, propoxy, isopropoxy, butoxy, isobutoxy, tert-butoxy, and the like.

As used herein, the term "3-10 membered heterocycloalkyl with 1-3 heteroatoms selected from the group consisting of N, S and O" refers to a saturated or partially saturated cyclic group having 3-10 atoms, wherein 1-3 atoms are heteroatoms selected from the group consisting of N, S and O. It may be a monocyclic ring or bicyclic form, such as bridged or spiro ring form. Specific examples may be oxetane, azetidine, tetrahydro-2H-pyranyl, piperidinyl, tetrahydrofuranyl, morpholinyl and pyrrolidinyl, and the like.

As used herein, the term "$C_6$-$C_{10}$ aryl" refers to aryl groups having 6 to 10 carbon atoms, such as phenyl, naphthyl, and the like.

As used herein, the term "5-10 membered heteroaryl having 1-3 heteroatoms selected from the group consisting of N, S and O" refers to cyclic aromatic groups having 5-10 atoms, of which 1-3 is selected from the group consisting of N, S and O. It may be a monocyclic ring or fused ring form. Specific examples may be pyridyl, pyridazinyl, pyrimidinyl, pyrazinyl, triazinyl, pyrrolyl, pyrazolyl, imidazolyl, (1,2,3)-triazolyl and (1,2,4)-triazolyl, tetrazyl, furyl, thienyl, isoxazolyl, thiazolyl, oxazolyl, etc.

Unless otherwise specified, all the groups described in the present invention may be substituted with substituents selected from the group consisting of halogen, nitrile, nitro, hydroxy, amino, $C_1$-$C_6$ alkyl-amine, $C_1$-$C_6$ alkyl, $C_2$-$C_6$ alkenyl, $C_2$-$C_6$ alkynyl, $C_1$-$C_6$ alkoxyl, halogenated $C_1$-$C_6$ alkyl, halogenated $C_2$-$C_6$ alkenyl, halogenated $C_2$-$C_6$ alkynyl, halogenated $C_1$-$C_6$ alkoxyl, allyl, benzyl, $C_6$-$C_{12}$ aryl, $C_1$-$C_6$ alkoxyl-$C_1$-$C_6$ alkyl, $C_1$-$C_6$ alkoxyl-carbonyl, phenoxycarbonyl, $C_2$-$C_6$ alkynyl-carbonyl, $C_2$-$C_6$ alkenyl-carbonyl, $C_3$-$C_6$ cycloalkyl-carbonyl, $C_1$-$C_6$ alkyl-sulfonyl, etc.

As used herein, "halogen" or "halogen atom" refers to F, Cl, Br, and I. As used herein, "halogen" or "halogen atom" refers to F, Cl, Br, and I. More preferably, the halogen or halogen atom is selected from F, Cl and Br. "Halogenated" means substituted by an atom selected from F, Cl, Br, and I.

Unless otherwise specified, the structural formula described herein are intended to include all isomeric forms (such as enantiomeric, diastereomeric, and geometric isomers (or conformational isomers)): for example, R, S configuration of asymmetrical centers, (Z), (E) isomers of double bonds, etc. Therefore, the single stereochemical isomers or enantiomers, diastereomers or geometric isomers (or conformers) of the compounds of the invention, or mixtures thereof all fall within the scope of the invention.

As used herein, the term "tautomer" means that structural isomers having different energies can exceed the low energy barrier and thereby transform between each other. For example, proton tautomers (proton shift) includes interconversion by proton transfer, such as 1H-carbazole and 2H-carbazole. Valence tautomers include interconversion through some bonding electron recombination.

As used herein, the term "solvate" refers to a complex of specific ratio formed by a compound of the invention coordinating to a solvent molecule.

The Compound of Formula I
A compound according to Formula I is provided:

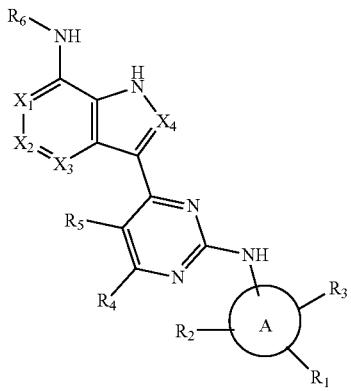

I wherein, $X^1$, $X^2$, $X^3$, $X^4$ are each independently CH or N; and at least one of $X^1$, $X^2$, $X^3$, and $X^4$ is N;

$R^1$, $R^3$ are independently selected from the group consisting of H, substituted or unsubstituted C1-C6 alkyl;

$R^2$ is independently selected from the group consisting of H, halogen, CN, substituted or unsubstituted C1-C6 alkyl, substituted or unsubstituted C1-C6 alkoxyl;

$R^4$, $R^5$ are independently selected from the group consisting of H, halogen, CN, substituted or unsubstituted C1-C6 alkyl;

$R^6$ is selected from the group consisting of H, substituted or unsubstituted C1-C6 alkyl, $R^7$—C(=O)—, $R^8$—S(=O)$_2$—, $R^9R^{10}$N—C(=O)—, $R^{11}R^{12}$N—S(=O)$_2$—, substituted or unsubstituted 5-12 membered heterocyclyl with 1-3 heteroatoms selected from N, S and O (including single ring, spiro ring, bridged ring or fused ring);

$R^7$, $R^8$, $R^9$, $R^{10}$, $R^{11}$, $R^{12}$ are each independently selected from the group consisting of H, substituted or unsubstituted C1-C6 alkyl, substituted or unsubstituted C1-C6 alkoxyl, substituted or unsubstituted C3-C8 cycloalkyl, substituted or unsubstituted 5-12 membered heterocyclyl with 1-3 heteroatoms selected from the group consisting of N, S and O;

unless otherwise specified, "substituted" refers to being substituted by one or more (for example, 2, 3, 4, etc.) substituents selected from the group consisting of halogen, C1-C6 alkoxyl, halogenated C1-C6 alkoxyl, C3-C8 cycloalkyl, halogenated C3-C8 cycloalkyl, methyl sulfone, oxo (=O), —CN, hydroxy, —NH$_2$, C1-C6 amine, carboxy, C1-C6 amide (—C(=O)—N(Rc)$_2$ or —NH—C(=O)(Rc), Rc is H or C1-C5 alkyl), or substituted or unsubstituted groups selected from the group consisting of C1-C6 alkyl, C6-C10 aryl, 5-10 membered heteroaryl with 1-3 heteroatoms selected from N, S, O, —(CH$_2$)—C6-C10 aryl, —(CH$_2$)-(5-10 membered heteroaryl with 1-3 heteroatoms selected from N, S and O), -(5-10 membered heteroarylene with 1-3 heteroatoms selected from N, S and O)—(C1-C6 alkyl), 5-12 membered heterocyclyl with 1-3 heteroatoms selected from N, S and O (including single ring, spiro ring, bridged ring or fused ring), and the substituents selected from the group consisting of halogen, C1-C6 alkyl, C1-C6 alkylene-OH, C1-C6 alkoxyl, oxo, —CN, —OH, C6-C10 aryl, 5-10 membered heteroaryl with 1-3 heteroatoms selected from N, S and O;

and in the compound of Formula I, each chiral center is in R configuration or S configuration.

In some embodiments, $X^1$, $X^2$, $X^3$, $X^4$, $R^1$, $R^2$, $R^3$, $R^4$, $R^5$, and $R^6$ are each independently the corresponding groups of the compounds in the examples.

In some embodiments, the compound of Formula I herein is selected from the following table:

1

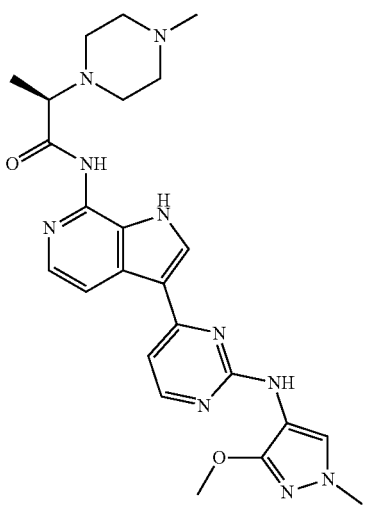 [SMILES: COc1nn(C)cc1Nc1nccc(-c2c[nH]c3c(NC(=O)[C@@H](C)N4CCN(C)CC4)nccc23)n1]

-continued
2
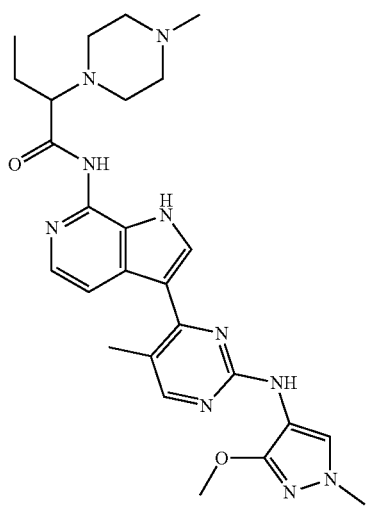 [SMILES: CCC(C(=O)Nc1nccc2c(-c3nc(Nc4cn(C)nc4OC)ncc3C)c[nH]c12)N1CCN(C)CC1]
3
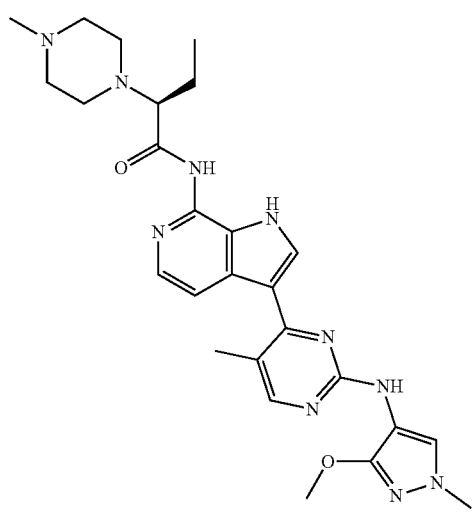
4
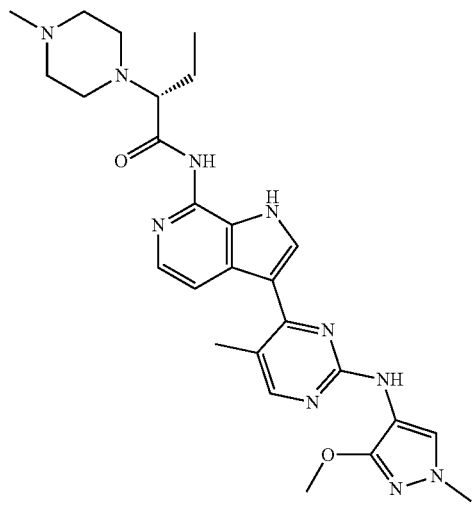

5
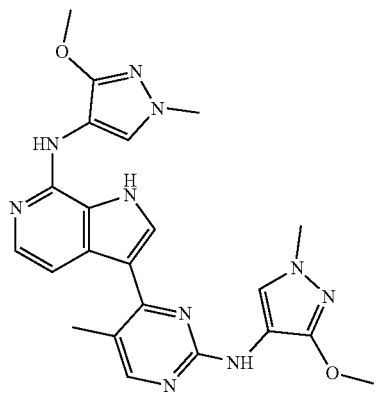 [SMILES: COc1nn(C)cc1Nc1ncc(C)c(-c2c[nH]c3c(Nc4cn(C)nc4OC)nccc23)n1]
6
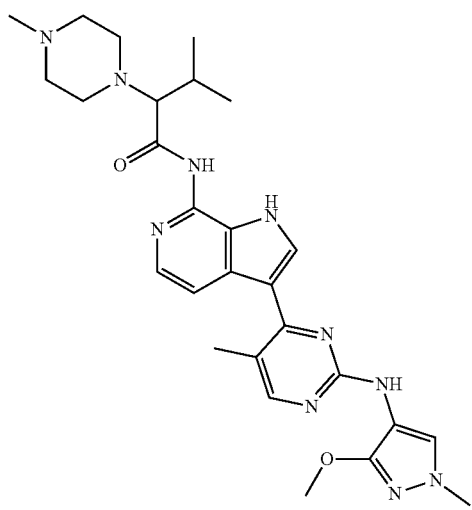
7
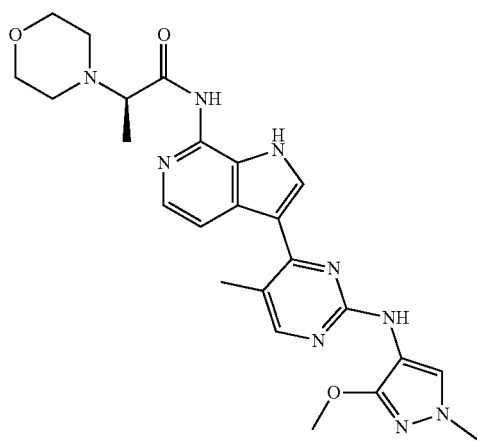 [SMILES: COc1nn(C)cc1Nc1ncc(C)c(-c2c[nH]c3c(NC(=O)[C@@H](C)N4CCOCC4)nccc23)n1]

8
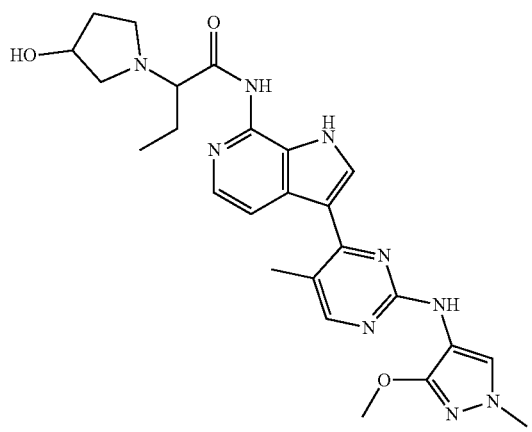 [SMILES: CCC(C(=O)Nc1nccc2c(-c3nc(Nc4cn(C)nc4OC)ncc3C)c[nH]c12)N1CCC(O)C1]
9
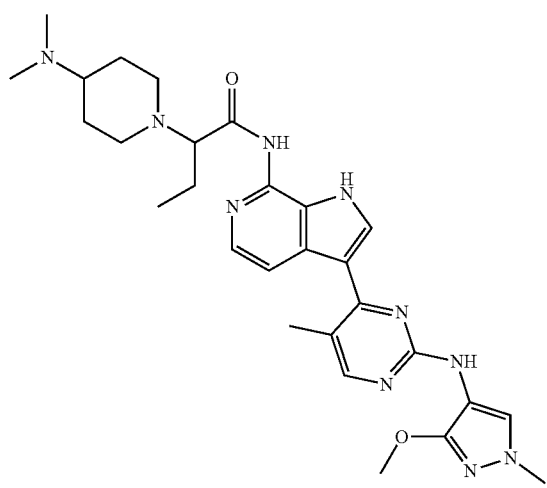
10
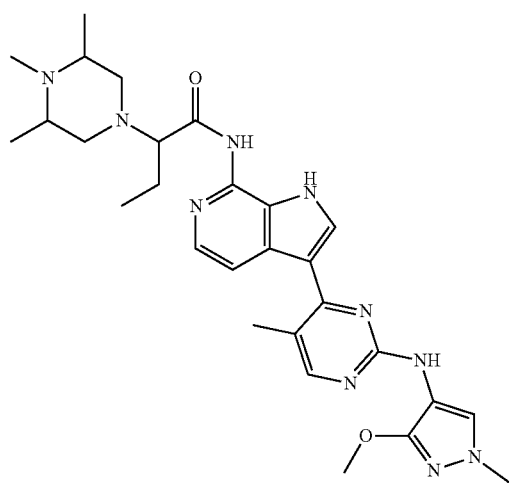

11
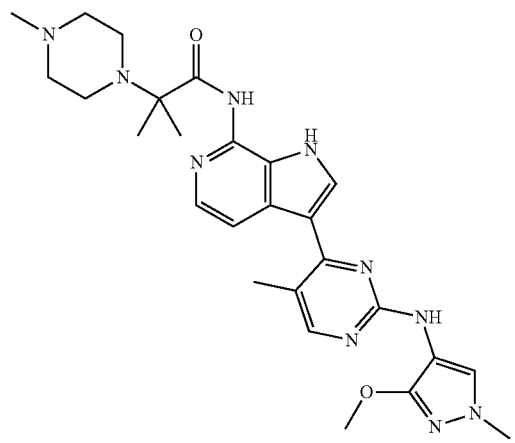
12
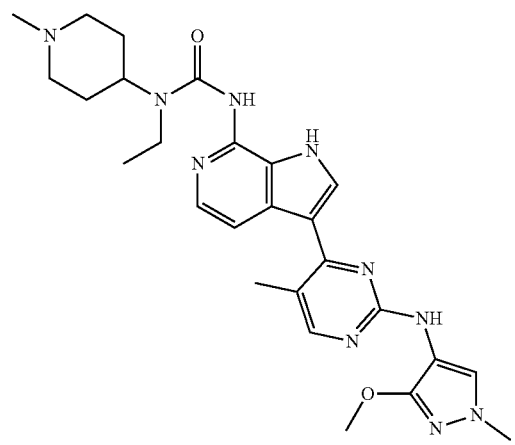
17
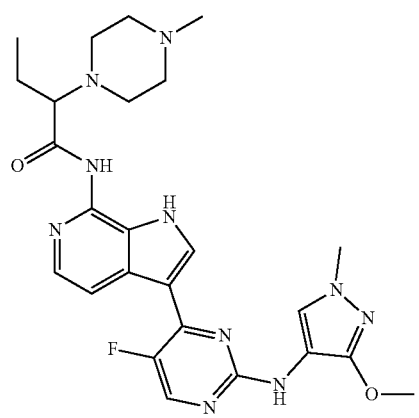 [SMILES: CCC(C(=O)Nc1nccc2c(-c3nc(Nc4cn(C)nc4OC)ncc3F)c[nH]c12)N1CCN(C)CC1]

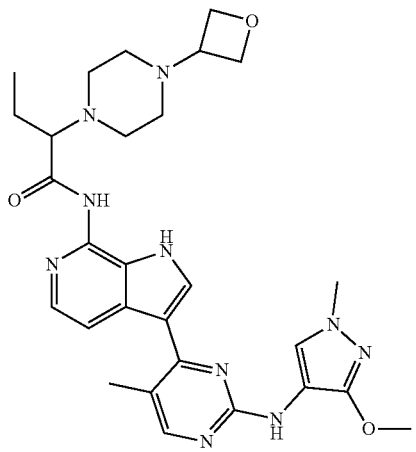 [SMILES: CCC(C(=O)Nc1nccc2c(-c3nc(Nc4cn(C)nc4OC)ncc3C)c[nH]c12)N1CCN(C2COC2)CC1]
18
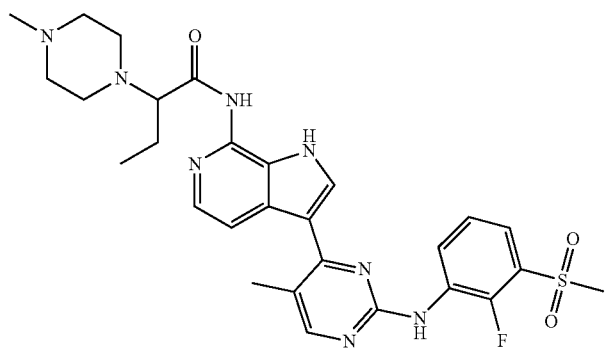
19
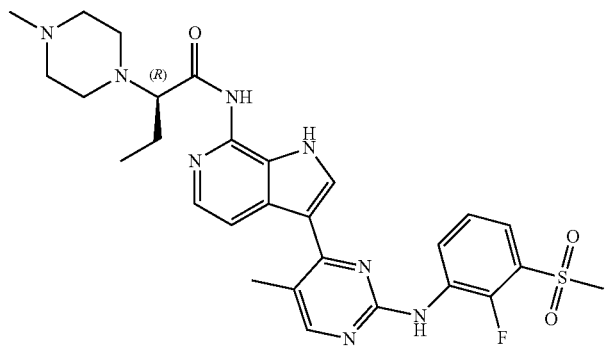
20
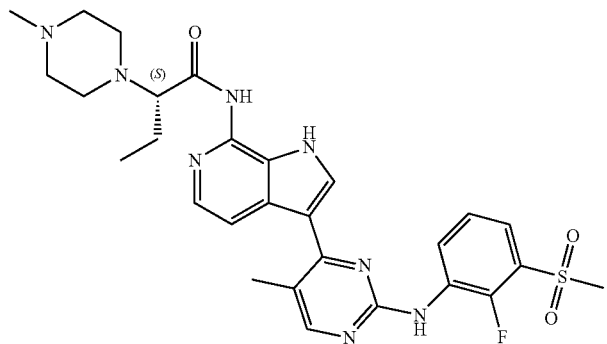
21

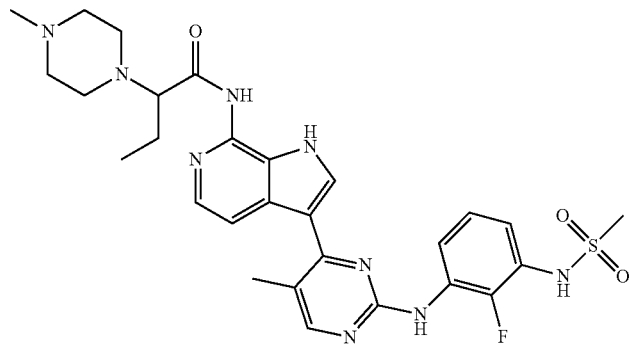 [SMILES: CCC(C(=O)Nc1nccc2c(-c3nc(Nc4cccc(NS(C)(=O)=O)c4F)ncc3C)c[nH]c12)N1CCN(C)CC1]
22
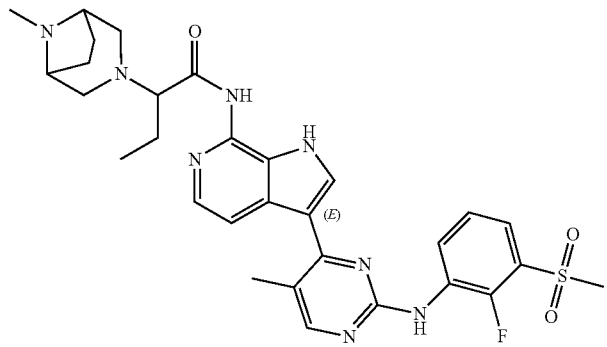
23
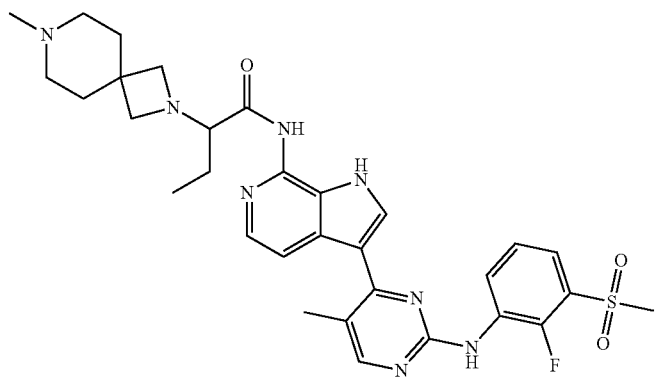
24
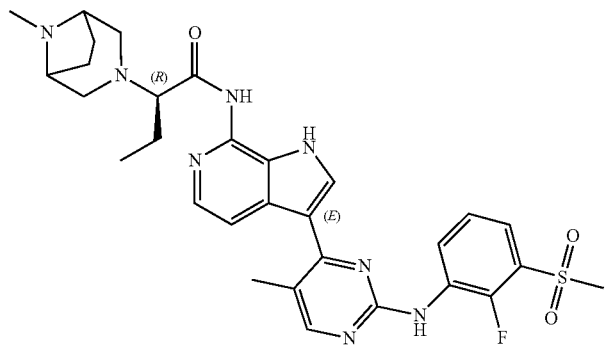
25

-continued
| | |
|---|---|
| 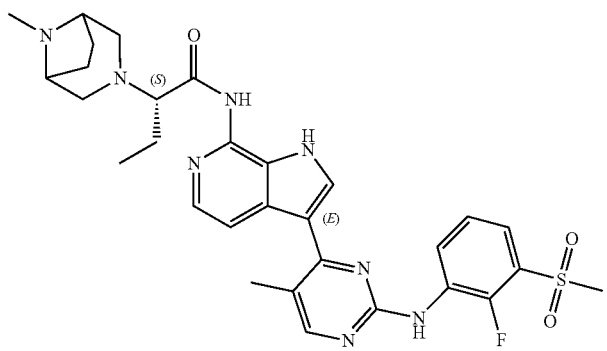 | 26 |
| 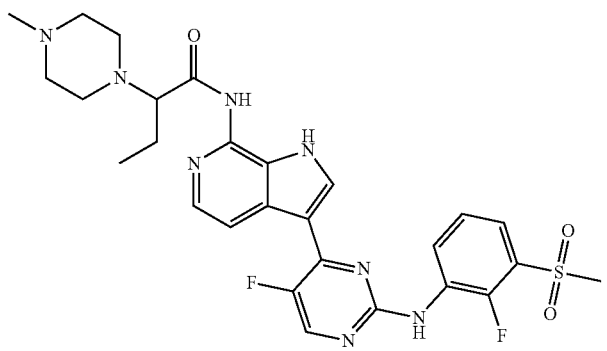 | 27 |
| 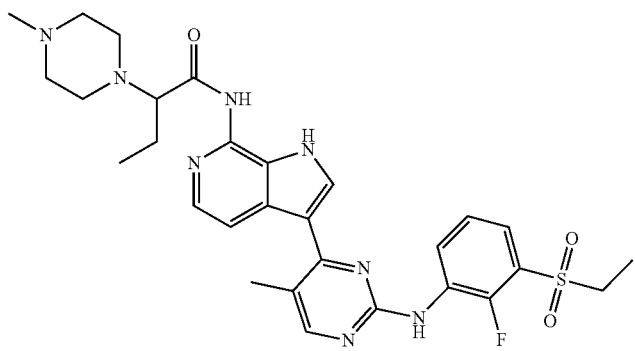 [SMILES: CCC(C(=O)Nc1nccc2c(-c3nc(Nc4cccc(S(=O)(=O)CC)c4F)ncc3C)c[nH]c12)N1CCN(C)CC1] | 28 |
| 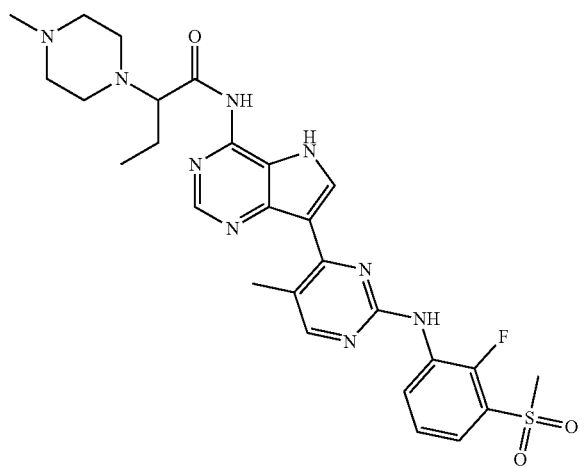 [SMILES: CCC(C(=O)Nc1ncnc2c(-c3nc(Nc4cccc(S(C)(=O)=O)c4F)ncc3C)c[nH]c12)N1CCN(C)CC1] | 29 |

30
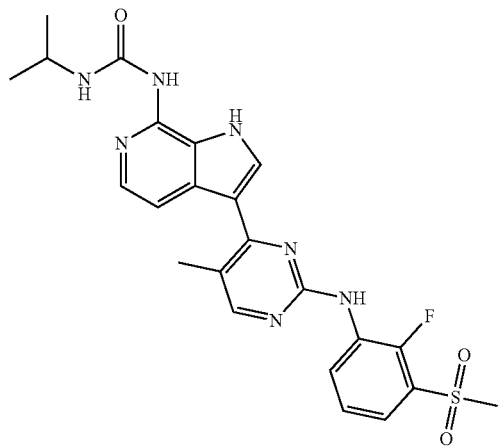 [SMILES: Cc1cnc(Nc2cccc(S(C)(=O)=O)c2F)nc1-c1c[nH]c2c(NC(=O)NC(C)C)nccc12]
31
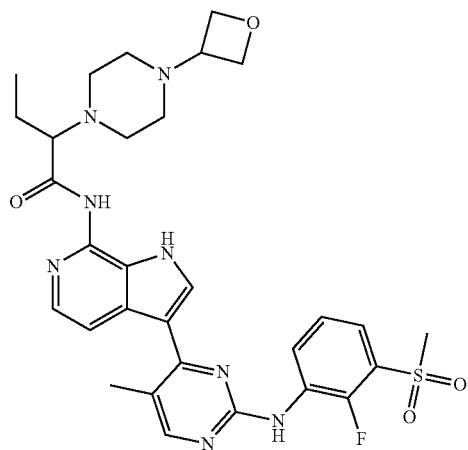 [SMILES: CCC(C(=O)Nc1nccc2c(-c3nc(Nc4cccc(S(C)(=O)=O)c4F)ncc3C)c[nH]c12)N1CCN(C2COC2)CC1]
32
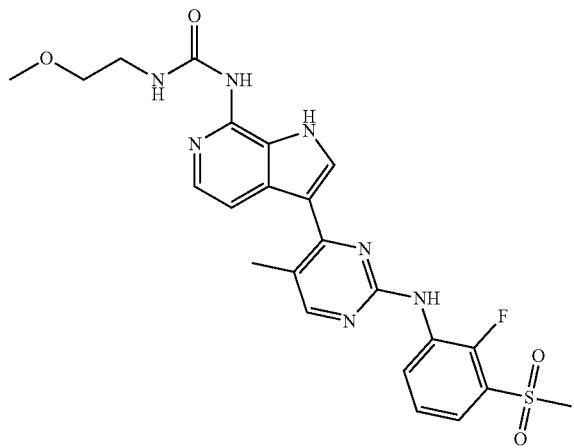

33
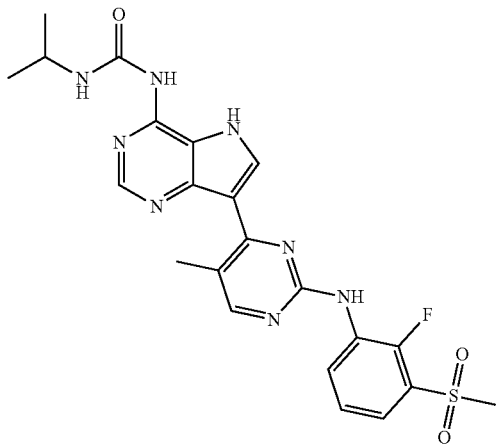 [SMILES: Cc1cnc(Nc2cccc(S(C)(=O)=O)c2F)nc1-c1c[nH]c2c(NC(=O)NC(C)C)ncnc12]
34
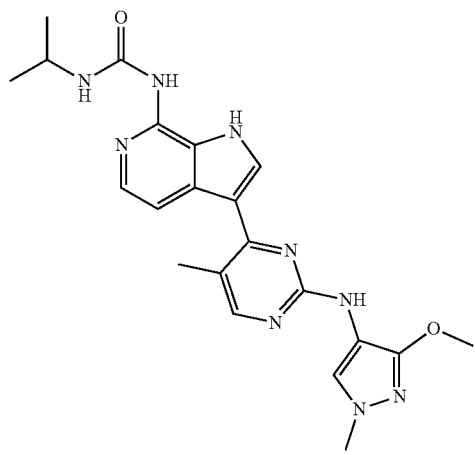 [SMILES: COc1nn(C)cc1Nc1ncc(C)c(-c2c[nH]c3c(NC(=O)NC(C)C)nccc23)n1]
35
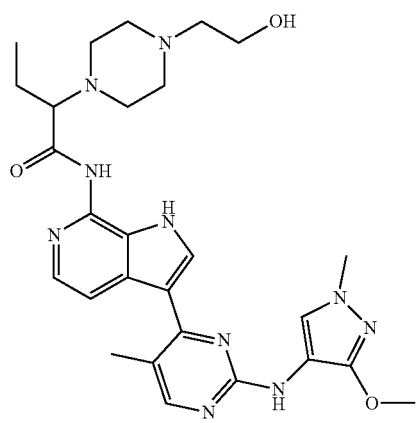 [SMILES: CCC(C(=O)Nc1nccc2c(-c3nc(Nc4cn(C)nc4OC)ncc3C)c[nH]c12)N1CCN(CCO)CC1]

36
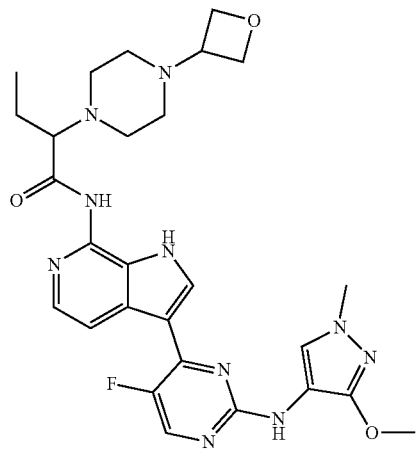 [SMILES: CCC(C(=O)Nc1nccc2c(-c3nc(Nc4cn(C)nc4OC)ncc3F)c[nH]c12)N1CCN(C2COC2)CC1]
37
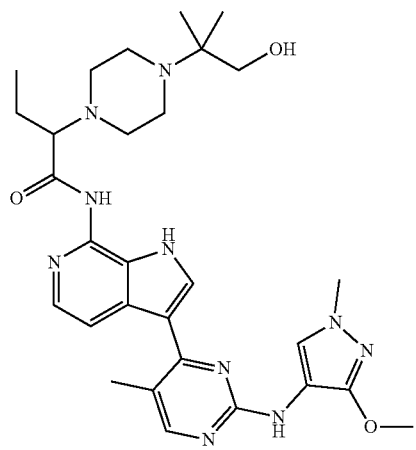 [SMILES: CCC(C(=O)Nc1nccc2c(-c3nc(Nc4cn(C)nc4OC)ncc3C)c[nH]c12)N1CCN(C(C)(C)CO)CC1]
38
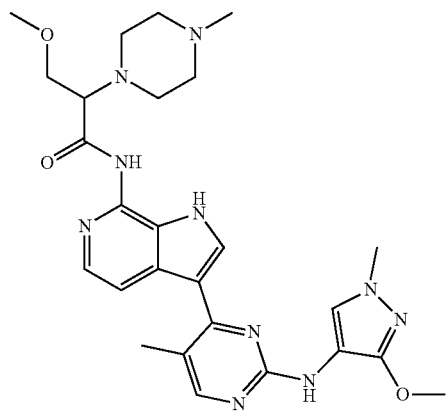

39
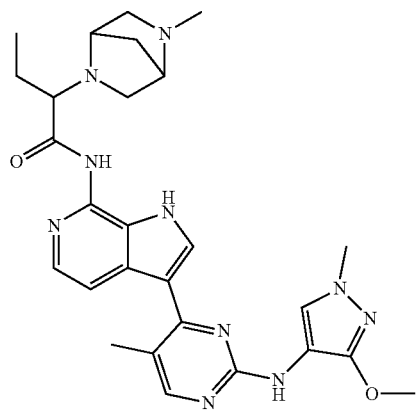 [SMILES: CCC(C(=O)Nc1nccc2c(-c3nc(Nc4cn(C)nc4OC)ncc3C)c[nH]c12)N1CC2CC1CN2C]
40
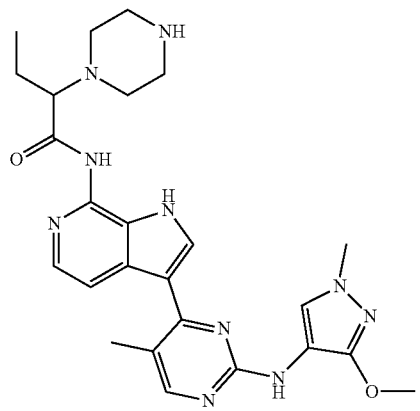 [SMILES: CCC(C(=O)Nc1nccc2c(-c3nc(Nc4cn(C)nc4OC)ncc3C)c[nH]c12)N1CCNCC1]
41
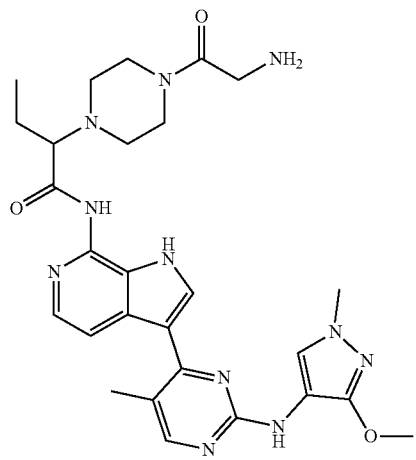 [SMILES: CCC(C(=O)Nc1nccc2c(-c3nc(Nc4cn(C)nc4OC)ncc3C)c[nH]c12)N1CCN(C(=O)CN)CC1]

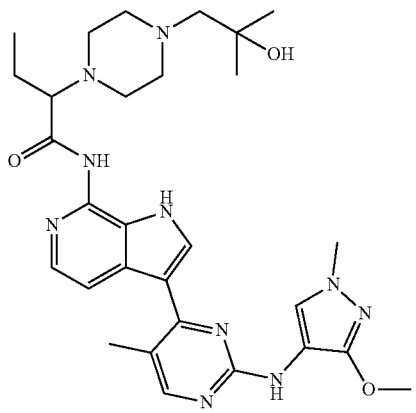 [SMILES: CCC(C(=O)Nc1nccc2c(-c3nc(Nc4cn(C)nc4OC)ncc3C)c[nH]c12)N1CCN(CC(C)(C)O)CC1]
42
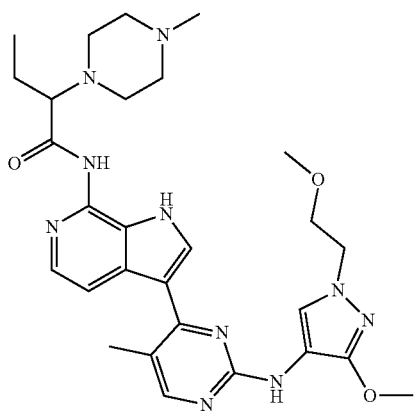 [SMILES: CCC(C(=O)Nc1nccc2c(-c3nc(Nc4cn(CCOC)nc4OC)ncc3C)c[nH]c12)N1CCN(C)CC1]
43
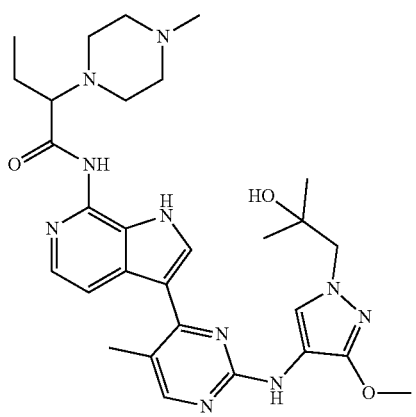 [SMILES: CCC(C(=O)Nc1nccc2c(-c3nc(Nc4cn(CC(C)(C)O)nc4OC)ncc3C)c[nH]c12)N1CCN(C)CC1]
44
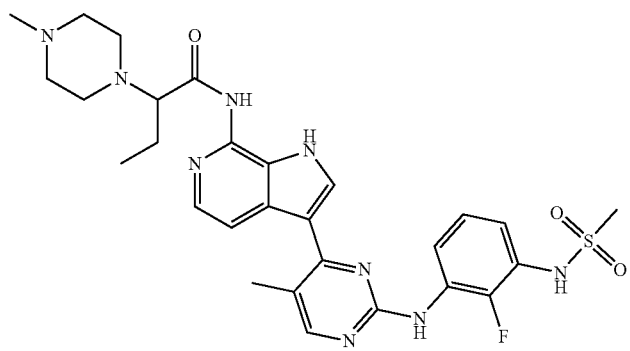 [SMILES: CCC(C(=O)Nc1nccc2c(-c3nc(Nc4cccc(NS(C)(=O)=O)c4F)ncc3C)c[nH]c12)N1CCN(C)CC1]
45

-continued
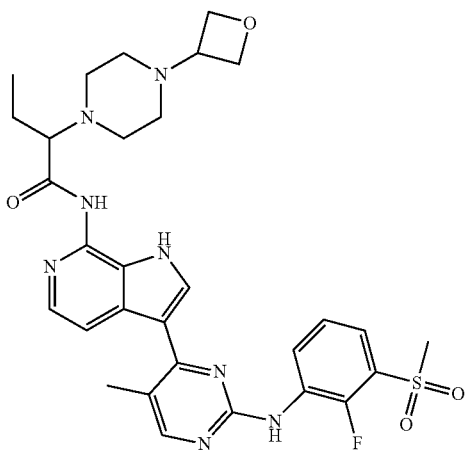 [SMILES: CCC(C(=O)Nc1nccc2c(-c3nc(Nc4cccc(S(C)(=O)=O)c4F)ncc3C)c[nH]c12)N1CCN(C2COC2)CC1]
46
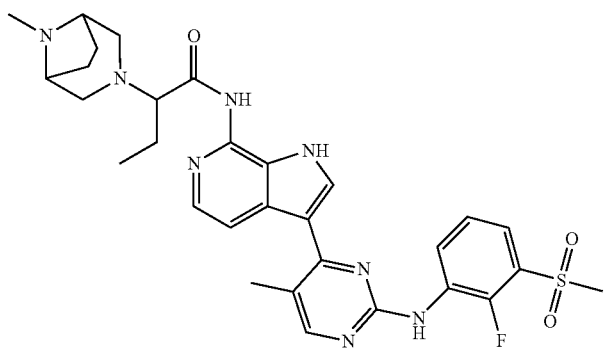
47
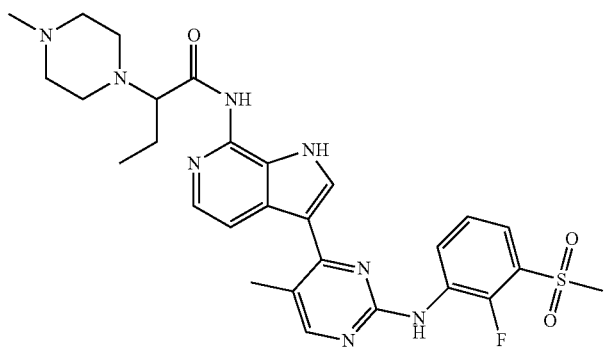
48
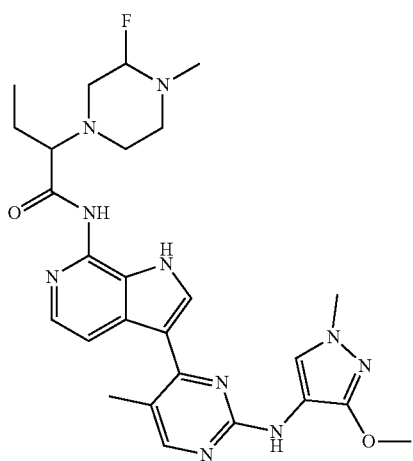 [SMILES: CCC(C(=O)Nc1nccc2c(-c3nc(Nc4cn(C)nc4OC)ncc3C)c[nH]c12)N1CCN(C)C(F)C1]
49

50
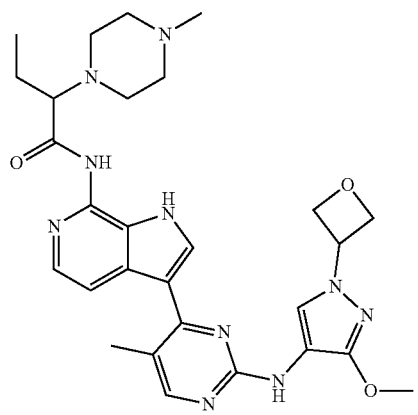 [SMILES: CCC(C(=O)Nc1nccc2c(-c3nc(Nc4cn(C5COC5)nc4OC)ncc3C)c[nH]c12)N1CCN(C)CC1]
51
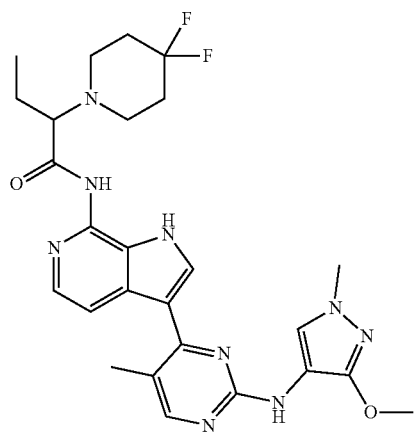 [SMILES: CCC(C(=O)Nc1nccc2c(-c3nc(Nc4cn(C)nc4OC)ncc3C)c[nH]c12)N1CCC(F)(F)CC1]
52
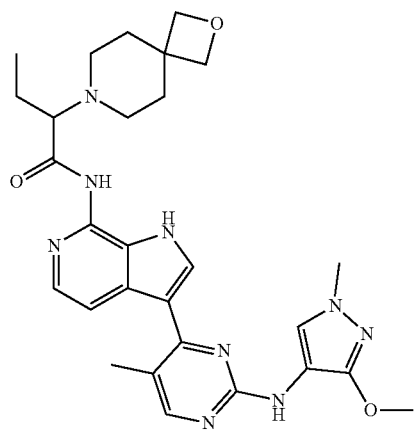 [SMILES: CCC(C(=O)Nc1nccc2c(-c3nc(Nc4cn(C)nc4OC)ncc3C)c[nH]c12)N1CCC2(CC1)COC2]

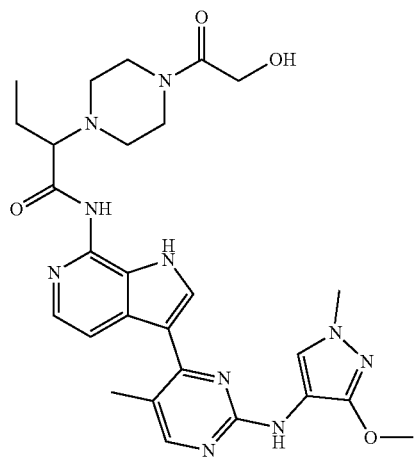 [SMILES: CCC(C(=O)Nc1nccc2c(-c3nc(Nc4cn(C)nc4OC)ncc3C)c[nH]c12)N1CCN(C(=O)CO)CC1]

56 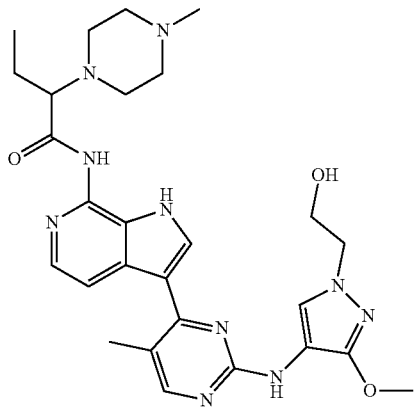 [SMILES: CCC(C(=O)Nc1nccc2c(-c3nc(Nc4cn(CCO)nc4OC)ncc3C)c[nH]c12)N1CCN(C)CC1]
57 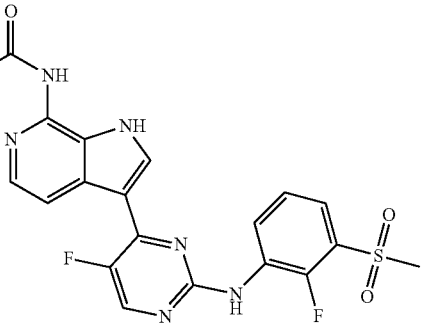
58 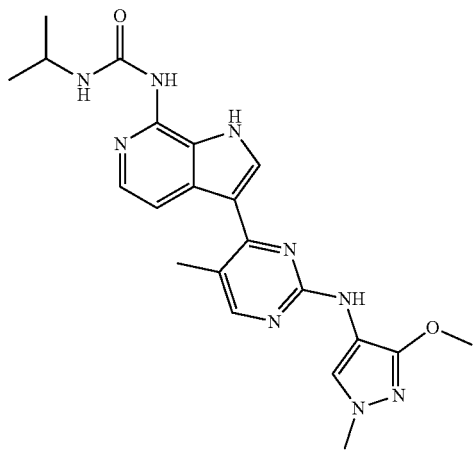 [SMILES: COc1nn(C)cc1Nc1ncc(C)c(-c2c[nH]c3c(NC(=O)NC(C)C)nccc23)n1]
59 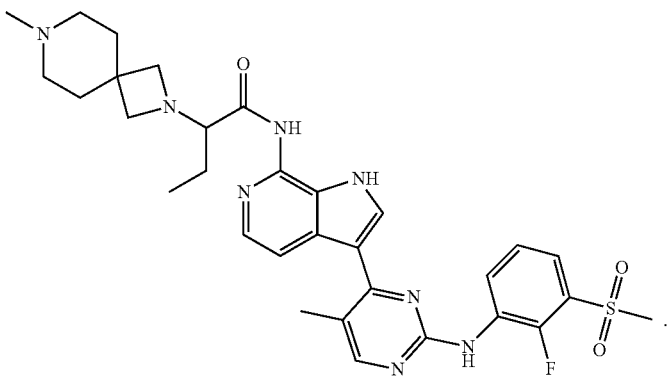

The compound herein can be a JAK inhibitor, in preferred examples, be a selective JAK kinase inhibitor, for example, selectively inhibits one or more of JAK1, JAK2, JAK3 or Tyk2. In preferred examples herein, the JAK inhibitor highly selectively inhibits JAK1.

Preparation of Compound of Formula I

The compound of Formula I herein can be prepared by the following method:

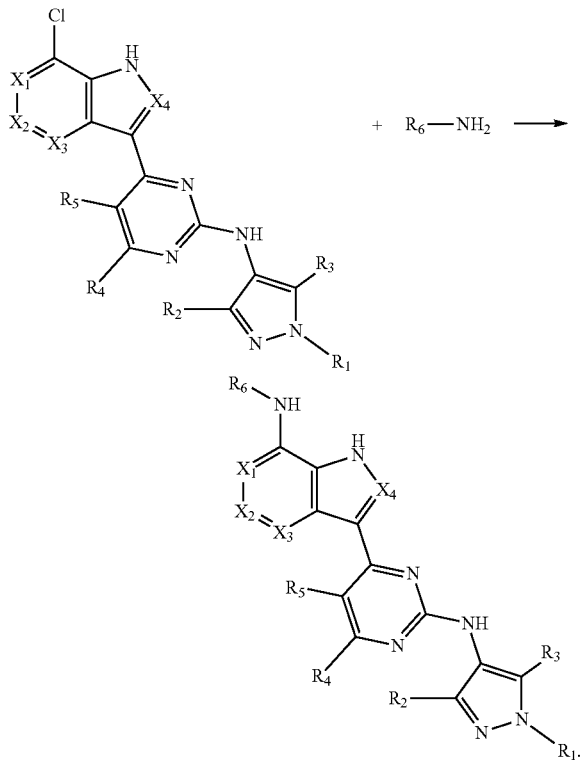

Pharmaceutical Composition and the Administration Thereof

Since the compound herein has excellent JAK kinase inhibitory activity, the compound of the present invention and various crystal forms thereof, pharmaceutically acceptable inorganic or organic salts, hydrates or solvates thereof, and pharmaceutical composition containing the compound according to the present invention as main active ingredient can be used to prevent and/or treat diseases related to the activity or expression of JAK kinase (for example, cancer).

The pharmaceutical composition of the invention comprises the compound of the present invention in a safe and effective dosage range and pharmaceutically acceptable excipients or carriers. Wherein the "safe and effective dosage" means that the amount of compound is sufficient to significantly ameliorate the condition without causing significant side effects. Generally, the pharmaceutical composition contains 1-2000 mg compounds of the invention per dose, preferably, 10-200 mg compounds of the invention per dose. Preferably, the "dose" is a capsule or tablet.

"Pharmaceutically acceptable carrier" means one or more compatible solid or liquid fillers, or gelatinous materials which are suitable for human use and should be of sufficient purity and sufficiently low toxicity. "Compatibility" means that each component in the composition can be admixed with the compounds of the present invention and with each other without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation of administration mode for the compound or pharmaceutical compositions of the present invention, and the representative administration mode includes (but is not limited to): oral, parenteral (intravenous, intramuscular or subcutaneous).

Solid dosage forms for oral administration include capsules, tablets, pills, powders and granules. In these solid dosage forms, the active compounds are mixed with at least one conventional inert excipient (or carrier), such as sodium citrate or $CaHPO_4$, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

Compounds of the present invention can be administrated alone, or in combination with any other pharmaceutically acceptable compounds.

In the case of co-administration, the pharmaceutical composition can also include one or more other pharmaceutically acceptable compounds. One or more other pharmaceutically acceptable compounds may be used simultaneously, separately or sequentially with the compound of the present invention.

When the pharmaceutical compositions are used, a safe and effective amount of compound of the present invention is applied to a mammal (such as human) in need of, wherein the dose of administration is a pharmaceutically effective dose. For a person weighed 60 kg, the daily dose is usually 1-2000 mg, preferably 20-500 mg. Of course, the particular dose should also depend on various factors, such as the route of administration, patient healthy status, which are well within the skills of an experienced physician.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

Example 1: (R)—N-(3-(2-((3-Methoxy-1-methyl-1H-pyrazol-4-yl)amino) pyrimidin-4-yl)-1H-pyrrolo[2,3-c]pyridin-7-yl)-2-(4-methylpiperazin-1-yl)propionamide

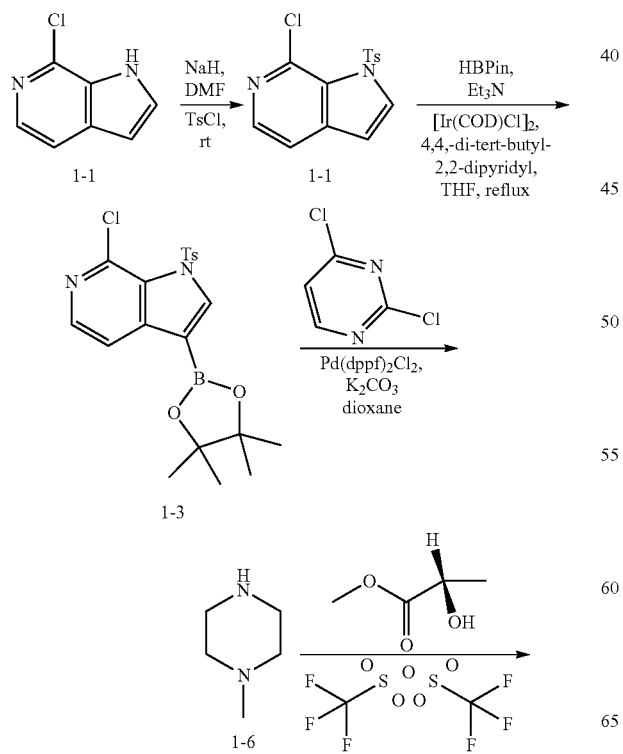

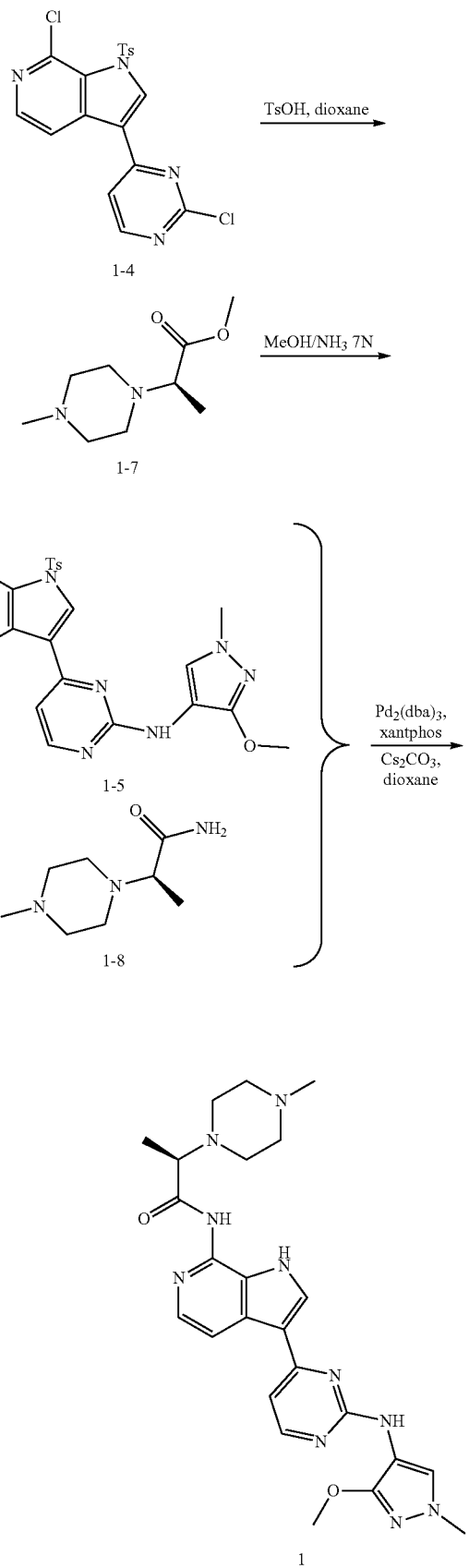

Example 1-2: 7-Chloro-1-tosyl-1H-pyrrolo[2,3-c]pyridine

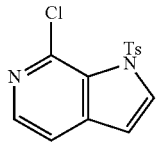

Sodium hydrogen (375 mg, 9.37 mmol) was added to the solution of compound 1-1 (950 mg, 6.25 mmol) in DMF (15 mL) in an ice-water bath. The mixture was stirred for 20 minutes under ice-water bath. Then p-toluenesulfonyl chloride (1.42 g, 9.37 mmol) was added to the solution in portions and stirred at room temperature for 4 hours. The reaction was monitored by TLC and LCMS. After 1-1 disappeared, the reaction was quenched with 100 ml of water. The mixture was extracted three times with ethyl acetate (50 ml*3). The organic phases were combined, dried over anhydrous sodium sulfate, and concentrated to give the product (1.45 g, yield 76%). MS (ESI): m/z=307 [M+H]$^+$.

Example 1-3: 7-Chloro-3-(4,4,5,5-tetramethyl-1,3,2-dioxaborolan-2-yl)-1-toluenesulfonyl-1H-pyrrolo[2,3-c]pyridine

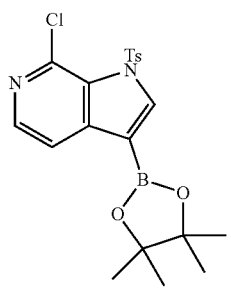 [SMILES: Cc1ccc(S(=O)(=O)n2cc(B3OC(C)(C)C(C)(C)O3)c3ccnc(Cl)c32)cc1]

A solution of compound 1-2 (1.01 g, 3.6 mmol), pinacolborane (1 g, 7.2 mmol), [Ir(COD)Cl]$_2$ (120 mg, 0.18 mmol), 4,4'-di-tert-butyl-2,2'-dipyridine (96 mg, 0.38 mmol) and triethylamine (727 mg, 7.2 mmol) in tetrahydrofuran (50 mL) was stirred at 80° C. for 3 hour under nitrogen atmosphere. The reaction was monitored by LCMS. After the reaction was completed, the solution was directly concentrated and purified by column chromatography (petroleum ether: ethyl acetate/10:1-8:1) to provide the 980 mg of product as a yellow solid, yield 63%. MS (ESI): m/z=433 [M+H]$^+$.

Example 1-4: 7-Chloro-3-(2-chloropyrimidin-4-yl)-1-tosyl-1H-pyrrolo[2,3-c]pyridine

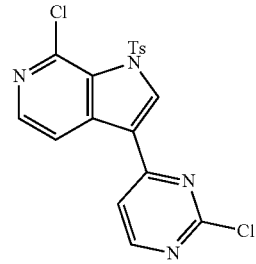 [SMILES: Cc1ccc(S(=O)(=O)n2cc(-c3ccnc(Cl)n3)c3ccnc(Cl)c32)cc1]

A solution of compound 1-3 (880 mg, 2 mmol), 2,4-dichloropyrimidine (301 mg, 2 mmol), Pd(dppf)Cl$_2$ (146 mg, 0.2 mmol) and potassium carbonate (552 mg, 4 mmol) in 1,4-dioxane (50 ml) was stirred overnight at 100° C. under nitrogen atmosphere. After the reaction was completed, the solution was concentrated to dryness, and 260 mg of product was purified by column chromatography (petroleum ether: ethyl acetate/5:1) with a yield of 30%. MS (ESI): m/z=419 [M+H]$^+$.

Examples 1-5: 4-(7-Chloro-1-tosyl-1H-pyrrolo[2,3-c]pyridin-3-yl)-N-(3-methoxy-1-methyl-1H-pyrazol-4-yl)pyrimidin-2-amine

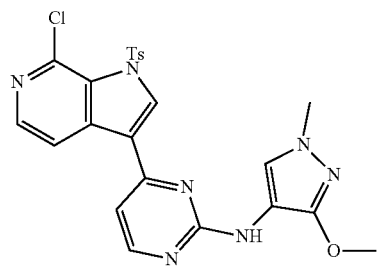 [SMILES: COc1nn(C)cc1Nc1nccc(-c2cn(S(=O)(=O)c3ccc(C)cc3)c3c(Cl)nccc23)n1]

A solution of compound 1-4 (230 mg, 0.55 mmol), 3-methoxy-1-methyl-1H-pyrazole-4-amine (84 mg, 0.66 mmol) and p-methyltoluenesulfonic acid (10 mg) in dioxane (15 ml) was stirred overnight at 100° C. After the reaction was completed, the mixture was neutralized with saturated sodium bicarbonate solution, extracted with ethyl acetate (30 ml), dried over anhydrous sodium sulfate, concentrated, and purified on a TLC plate to provide the product (20 mg, yield 10%). $^1$H NMR (400 MHz, CD$_3$OD-d4): δ (ppm): δ (ppm) 8.41 (s, 2H), 8.20 (d, J=5.6 Hz, 1H), 8.00 (d, J=4.8 Hz, 1H), 7.67 (s, 1H), 7.20 (d, J=5.2 Hz, 1H), 4.03 (s, 3H), 3.78 (s, 3H). MS-ESI: m/z 356[M+H]$^+$.

Examples 1-7: Methyl (R)-2-(4-methylpiperazin-1-yl)propionate

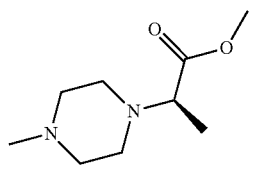

Dichloromethane (50 ml) and methyl (S)-2-hydroxypropionate (3 g, 28.8 mmol), 2,6-lutidine (3.7 ml, 31.7 mmol) was added into a three-necked flask (250 ml) under nitrogen atmosphere, and cooled to −78° C. Then trifluoromethanesulfonic anhydride (5.36 ml g, 31.7 mmol) was slowly added, and the mixture was stirred for 30 minutes, and then warmed to room temperature and stirred for another one hour. The organic phase was washed twice with 1N aqueous hydrochloric acid solution, dried over sodium sulfate, concentrated to residue. The resulting oil was dissolved in dichloromethane (50 ml), cooled to 0° C. Then 1-methylpiperazine (6.5 g, 64.6 mmol) was slowly added to the reaction solution, and potassium carbonate (21.2 g, 153.7 mmol) was added at 0° C. The mixture was stirred overnight at room temperature. After the reaction was completed, the reaction solution was washed with brine, dried, and concentrated to dryness to provide 5.7 g of yellow oil. MS (ESI): m/z=187 [M+H]$^+$.

Example 1-8: (R)-2-(4-methylpiperazin-1-yl)propionamide

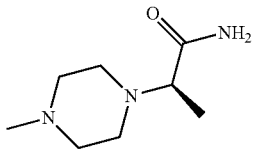

Ammonia methanol solution (7N, 46 mL), compound 1-7 (3.0 g, 16.1 mmol) was added to the autoclave (100 mL). The reaction mixture was heated to 150° C. and stirred for 48 hours. The reaction solution was directly concentrated to dryness, and the crude was purified to provide a white solid (480 mg, yield 17%). $^1$HNMR (400 MHz, MeOD): δ (ppm) 3.022-2.970 (m, 1H), 2.607-2.442 (m, 8H), 2.276 (s, 3H), 1.231 (d, J=3.6 Hz, 3H). MS (ESI): m/z=172 [M+H]$^+$.

Example 1: (R)—N-(3-(2-((3-Methoxy-1-methyl-1H-pyrazol-4-yl)amino) pyrimidin-4-yl)-1H-pyrrolo[2,3-c]pyridin-7-yl)-2-(4-methylpiperazin-1-yl) propionamide

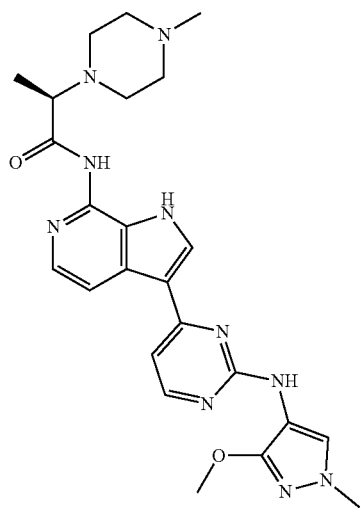 [SMILES: COc1nn(C)cc1Nc1nccc(-c2c[nH]c3c(NC(=O)[C@@H](C)N4CCN(C)CC4)nccc23)n1]

To a solution of Example 1-5 (25 mg, 0.070 mmol), (R)-2-(4-methylpiperazin-1-yl)propionamide (36 mg, 0.21 mmol), cesium carbonate (69 mg, 0.21 mmol) in dioxane (1 mL) were added bis(dibenzylideneacetone) palladium (13 mg, 0.014 mmol), 4,5-bisdiphenylphosphine-9,9-dimethylxanthene (16 mg, 0.028 mmol). The reaction solution was heated to 100° C. and stirred overnight. The reaction was monitored by LCMS. The target product (R)—N-(3-(2-((3-methoxy-1-methyl-1H-pyrazol-4-yl)amino)pyrimidin-4-yl)-1H-pyrrolo[2,3-c]pyridin-7-yl)-2-(4-methylpiperazin-1-yl) propionamide (1.3 mg, 3.8%) was obtained through preparative high performance liquid chromatography as a white solid. MS (ESI): m/z=491.7 [M+H]$^+$.

$^1$H NMR (400 MHz, DMSO-D6) δ 11.53 (s, 1H), 10.16 (s, 1H), 8.33-8.23 (m, 2H), 8.21 (d, J=5.3 Hz, 1H), 7.90 (s, 1H), 7.67 (s, 1H), 7.11 (d, J=5.3 Hz, 1H), 3.77 (s, 3H), 3.68 (s, 3H), 3.49 (d, J=7.0 Hz, 1H), 2.64-2.50 (m, 4H), 2.44-2.25 (m, 4H), 2.15 (s, 3H), 1.24 (d, J=7.0 Hz, 3H).

Example 2: N-(3-(2-((3-Methoxy-1-methyl-1H-pyrazol-4-yl)amino)-5-methylpyrimidin-4-yl)-1H-pyrrolo[2,3-c]pyridin-7-yl)-2-(4-methylpiperazin-1-yl)butanamide

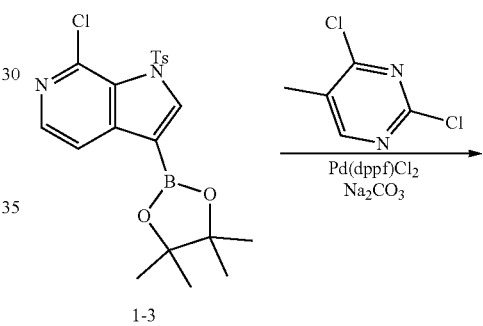

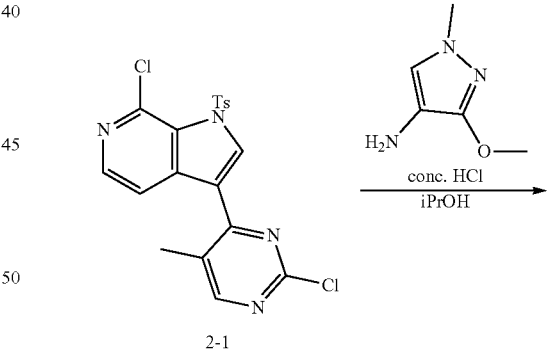

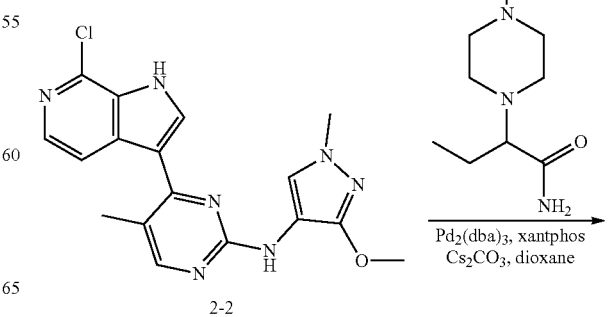

-continued

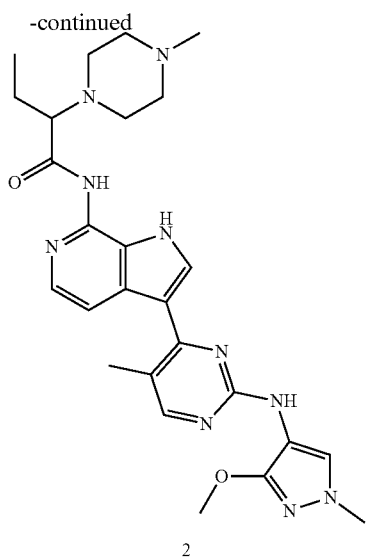

2

Example 2-1: 7-Chloro-3-(2-chloro-5-methylpyrimidin-4-yl)-1-tosyl-1H-pyrrolo[2,3-c]pyridine

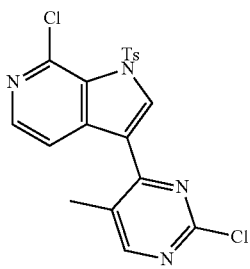 [SMILES: Cc1ccc(S(=O)(=O)n2cc(-c3nc(Cl)ncc3C)c3ccnc(Cl)c32)cc1]

To the mixture of tetrahydrofuran/water (15 ml/5 ml) were added Example 1-3 (350 mg, 0.81 mmol), 2,4-dichloro-5-methylpyrimidine (264 mg, 1.62 mmol), Pd(dppf)Cl$_2$ (60 mg, 0.08 mmol) and sodium carbonate (168 mg, 1.22 mmol) sequentially. The mixture was stirred at 80° C. for 2 hours. LCMS showed that the reaction was completed. The reaction solution was diluted with ethyl acetate and washed with water. The organic phase was dried with anhydrous sodium sulfate and concentrated to give a crude product. The obtained crude product was purified through a silica gel column (petroleum ether:ethyl acetate=5:1) to provide a yellow solid (200 mg, yield 57%. MS (ESI): m/z=432 [M+H]$^+$.

Example 2-2: 4-(7-Chloro-1H-pyrrolo[2,3-c]pyridin-3-yl)-N-(3-methoxy-1-methyl-1H-pyrazole-4-yl)-5-methylpyrimidin-2-amine

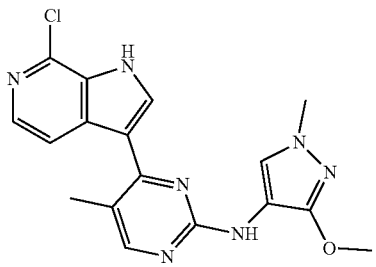 [SMILES: COc1nn(C)cc1Nc1ncc(C)c(-c2c[nH]c3c(Cl)nccc23)n1]

Compound Example 2-2 (25 mg, yield 8%) as a light yellow solid was obtained from Example 2-1 (365 mg, 0.843 mmol) by a similar method to Example 1. MS (ESI): m/z=370 [M+H]$^+$. $^1$H NMR (400 MHz, MeOD-d4): δ (ppm) 8.25 (s, 1H), 8.17 (s, 1H), 8.13 (s, 1H), 7.95 (d, J=5.6, 1H), 7.63 (s, 1H), 3.89 (s, 3H), 3.73 (s, 3H), 2.39 (s, 3H).

Example 2: N-(3-(2-((3-Methoxy-1-methyl-1H-pyrazol-4-yl)amino)-5-methylpyrimidin-4-yl)-1H-pyrrolo[2,3-c]pyridin-7-yl)-2-(4-methylpiperazin-1-yl)butanamide A white solid (7.8 mg, yield 22%) was obtained from Example 2-2 (25 mg, 0.068 mmol) using a similar method to Example 1. MS (ESI): m/z=519 [M+H]$^+$. $^1$H NMR (400 MHz, CD$_3$OD) δ 8.16-8.10 (m, 2H), 8.07 (s, 1H), 7.89 (d, J=5.6 Hz, 1H), 7.64 (s, 1H), 3.88 (s, 3H), 3.71 (s, 3H), 3.25-3.20 (m, 1H), 2.85-2.52 (m, 8H), 2.37 (s, 3H), 2.32 (s, 3H), 1.96-1.79 (m, 2H), 1.06 (t, J=7.4 Hz, 3H).

Example 3: (S)—N-(3-(2-((3-Methoxy-1-methyl-1H-pyrazol-4-yl)amino)-5-methylpyrimidin-4-yl)-1H-pyrrolo[2,3-c]pyridin-7-yl)-2-(4-methylpiperazin-1-yl)butanamide

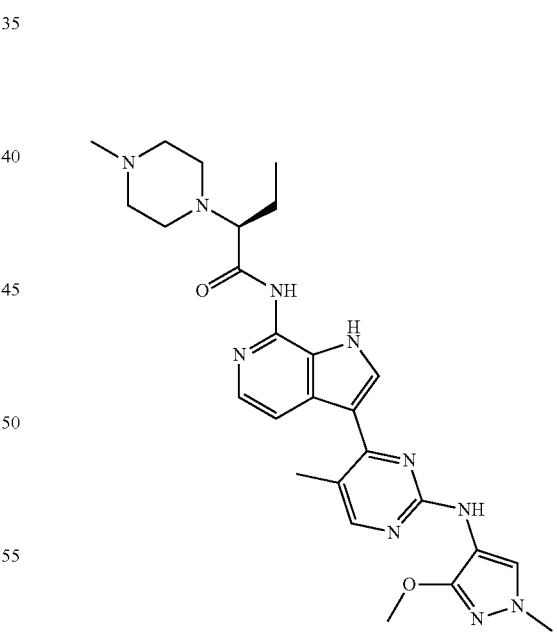

The target compound was prepared as described in Example 2, replacing the corresponding starting materials.

MS (ESI): m/z=519 [M+H]$^+$. $^1$H NMR (400 MHz, CD$_3$OD) δ 8.17-8.09 (m, 2H), 8.07 (s, 1H), 7.89 (d, J=5.6 Hz, 1H), 7.64 (s, 1H), 3.88 (s, 3H), 3.71 (s, 3H), 3.24-3.20 (m, 1H), 2.85-2.52 (m, 8H), 2.37 (s, 3H), 2.30 (s, 3H), 1.96-1.78 (m, 2H), 1.06 (t, J=7.4 Hz, 3H).

Example 4: (R)—N-(3-(2-((3-Methoxy-1-methyl-1H-pyrazol-4-yl)amino)-5-methylpyrimidin-4-yl)-1H-pyrrolo[2,3-c]pyridin-7-yl)-2-(4-methylpiperazin-1-yl)butanamide

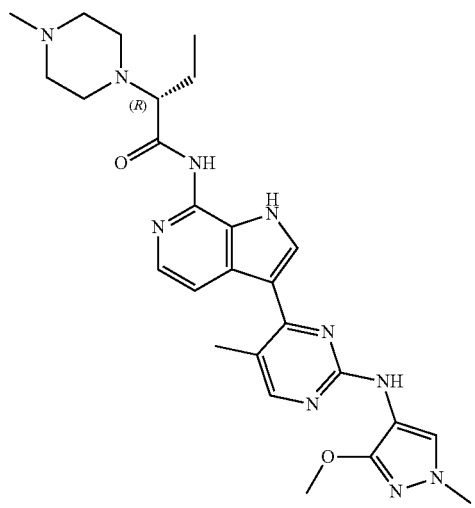

The target compound was prepared as described in Example 2, replacing the corresponding starting materials.
MS (ESI): m/z=519 [M+H]⁺. 1H NMR (400 MHz, CD3OD) δ 8.14-8.09 (m, 2H), 8.06 (s, 1H), 7.88 (d, J=5.7 Hz, 1H), 7.63 (s, 1H), 3.88 (s, 3H), 3.70 (s, 3H), 3.21 (dd, J=7.7, 5.6 Hz, 1H), 2.85-2.49 (m, 8H), 2.36 (s, 3H), 2.30 (s, 3H), 1.95-1.80 (m, 2H), 1.06 (t, J=7.4 Hz, 3H).

Example 5: N-(3-Methoxy-1-methyl-1H-pyrazol-4-yl)-3-(2-((3-methoxy-1-methyl-1H-pyrazole-4-yl)amino)-5-methylpyrimidin-4-yl)-1H-pyrrolo[2,3-c]pyridin-7-amine

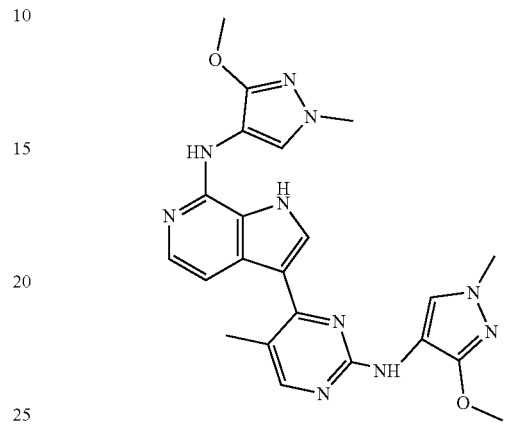

The target compound was prepared as described in Example 2, replacing the corresponding starting materials.
MS (ESI): m/z=461[M+H]⁺. ¹H NMR (400 MHz, DMSO-D6-d6): δ (ppm) 11.9 (s, 1H), 8.14 (s, 1H), 8.11 (s, 1H), 8.06 (d, J=3.2, 1H), 8.02 (s, 1H), 7.98 (s, 1H), 7.68 (m, 2H), 3.90 (s, 3H), 3.79 (s, 3H), 3.70 (s, 3H), 3.68 (s, 3H), 2.33 (s, 3H).

The following compounds were prepared using a similar method to Example 2, replacing the corresponding starting materials.

| Example | Compounds structure | LCMS, HNMR |
|---|---|---|
| 6 | 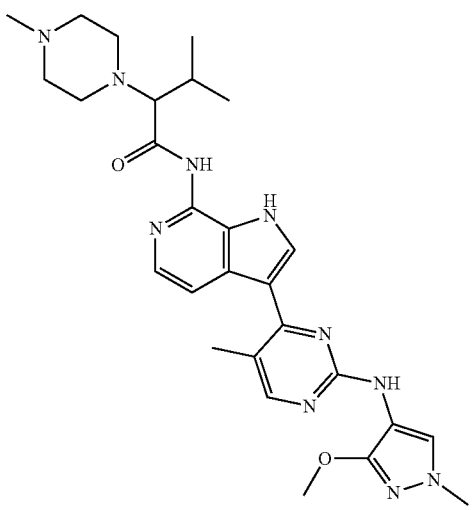 | MS (ESI): m/z = 533.1[M + H]⁺. ¹H NMR (400 MHz,CD3OD) δ 8.16-8.10 (m, 2H), 8.07 (s, 1H), 7.90 (d, J = 5.7 Hz, 1H), 7.64 (s, 1H), 3.88 (s, 3H), 3.71 (s, 3H), 3.05 (d, J = 9.0 Hz, 1H), 2.79 (s, 4H), 2.53 (s, 4H), 2.38 (s, 3H), 2.31-2.19 (m, 4H), 1.07 (d, J = 6.7 Hz, 3H), 1.01 (d, J = 6.6 Hz, 3H). |

| Example | Compounds structure | LCMS, HNMR |
|---|---|---|
| 7 | 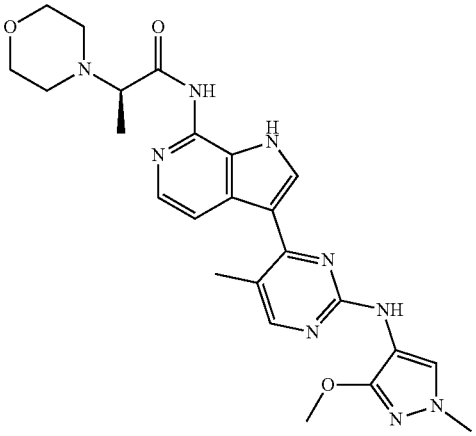 [SMILES: COc1nn(C)cc1Nc1ncc(C)c(-c2c[nH]c3c(NC(=O)[C@@H](C)N4CCOCC4)nccc23)n1] | MS (ESI): m/z = 492[M + H]⁺. ¹H NMR (400 MHz, CD3OD) δ 8.16-8.10 (m, 2H), 8.07 (s, 1H), 7.88 (d, J = 5.7 Hz, 1H), 7.63 (s, 1H), 3.88 (s, 3H), 3.84-3.79 (m, 4H), 3.71 (s, 3H), 3.44-3.36 (m, 1H), 2.75-2.60 (m, 4H), 2.37 (s, 3H), 1.39 (d, J = 7.0 Hz, 3H). |
| 8 | 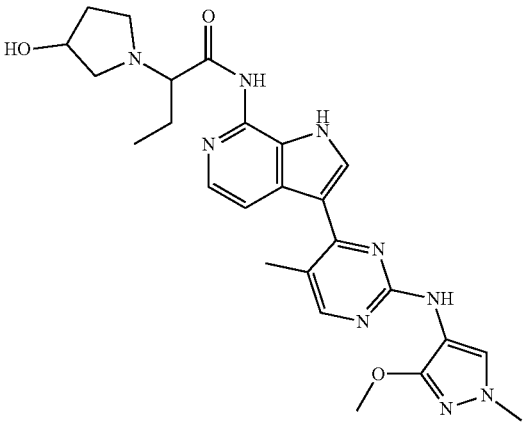 [SMILES: CCC(C(=O)Nc1nccc2c(-c3nc(Nc4cn(C)nc4OC)ncc3C)c[nH]c12)N1CCC(O)C1] | MS (ESI): m/z = 506[M + H]⁺. ¹H NMR (400 MHz, CD3OD) δ 8.17-8.11 (m, 2H), 8.08 (s, 1H), 7.91-7.87 (m, 1H), 7.64 (s, 1H), 4.39-4.33 (m, 1H), 3.88 (s, 3H), 3.71 (s, 3H), 3.15-3.08 (m, 1H), 3.05-2.98 (m, 1H), 2.93-2.87 (m, 1H), 2.82 2.72 (m, 1H), 2.70-2.62 (m, 1H), 2.38 (s, 3H), 2.24-2.12 (m, 1H), 1.99-1.87 (m, 2H), 1.83-1.74 (m, 1H), 1.05 (t, J = 7.5 Hz, 3H). |
| 9 | 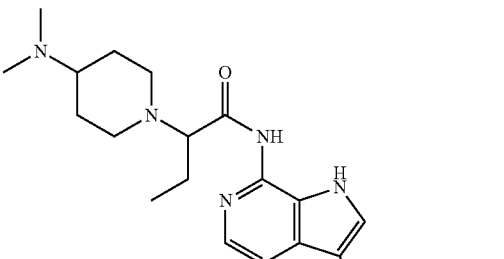 | MS (ESI): m/z = 547[M + H]⁺. ¹H NMR (400 MHz, CD3OD) δ 8.16-8.10 (m, 2H), 8.07 (s, 1H), 7.89 (d, J = 5.7 Hz, 1H), 7.64 (s, 1H), 3.88 (s, 3H), 3.71 (s, 3H), 3.21 (dd, J = 8.1, 5.2 Hz, 1H), 3.14-3.04 (m, 2H), 2.47 (t, J = 10.8 Hz, 1H), 2.37 (s, 3H), 2.35-2.23 (m, 8H), 1.95-1.79 (m, 4H), 1.71-1.57 (m, 2H), 1.06 (t, J = 7.4 Hz, 3H). |

-continued

| Example | Compounds structure | LCMS,HNMR |
|---------|---------------------|-----------|
| 10 | | MS (ESI): m/z = 547[M + H]⁺. ¹H NMR (400 MHz, CD3OD) δ 8.17-8.12 (m, 2H), 8.07 (s, 1H), 7.90 (d, J = 5.7 Hz, 1H), 7.63 (s, 1H), 3.88 (s, 3H), 3.71 (s, 3H), 3.36-3.30 (m, 1H), 3.09 (s, 4H), 2.69 (s, 3H), 2.60 (t, J = 11.7 Hz, 1H), 2.48 (t, J = 11.6 Hz, 1H), 2.37 (s, 3H), 1.98-1.80 (m, 2H), 1.33-1.24 (m, 6H), 1.07 (t, J = 7.4 Hz, 3H). |
| 11 | | MS (ESI): m/z = 639[M + H]⁺. ¹H NMR (400 MHz, CD3OD) δ 8.15-8.10 (m, 2H), 8.07 (s, 1H), 7.87 (d, J = 5.7 Hz, 1H), 7.64 (s, 1H), 3.88 (s, 3H), 3.71 (s, 3H), 2.68 (s, 8H), 2.37 (s, 3H), 2.33 (s, 3H), 1.37 (s, 6H). |
| 12 | | MS (ESI): m/z = 394[M + H]⁺. ¹H NMR (400 MHz, DMSO-d₆) δ 11.85 (s, 1H), 9.16 (s, 1H), 8.90 (brs, 1H), 8.14 (d, J = 2.8 Hz, 1H), 8.12 (s, 1H), 8.04 (s, 1H), 7.88 (brs, 1H), 7.72 (d, J = 5.4 Hz, 1H), 7.61 (s, 1H), 6.96 (brs, 1H), 3.74 (s, 3H), 3.64 (s, 3H), 2.29 (s, 3H). |

Example 17: N-(3-(5-Fluoro-2-((3-methoxy-1-methyl-1H-pyrazol-4-yl) amino)pyrimidin-4-yl)-1H-pyrrole[2,3-c]pyridin-7-yl)-2-(4-methylpiperazin-1-yl)butanamide
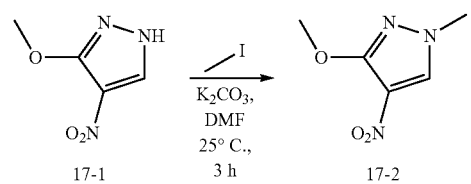
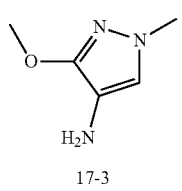
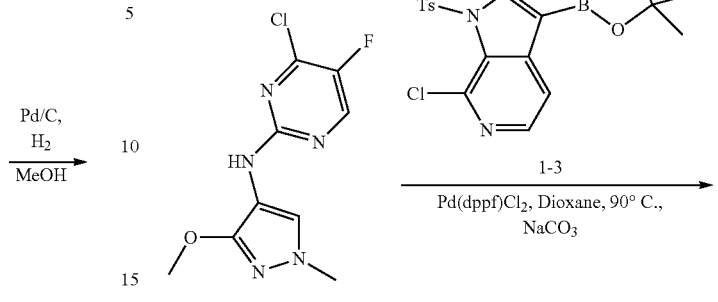
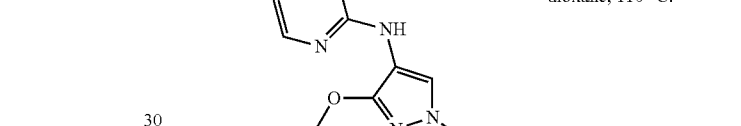
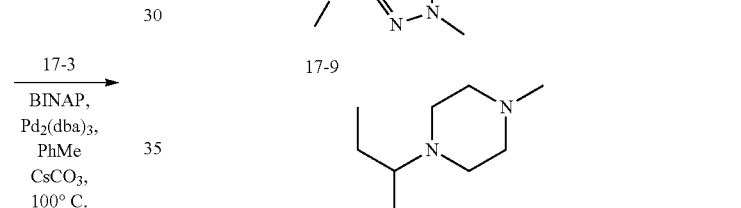
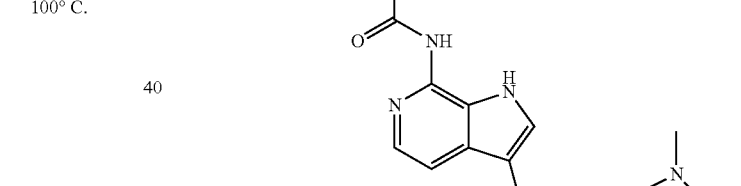
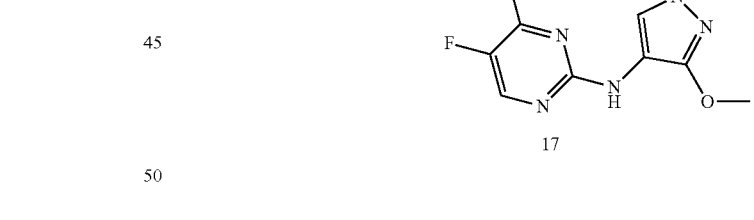
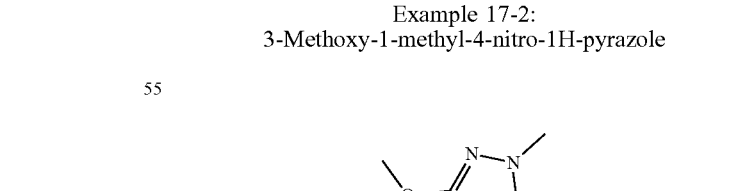
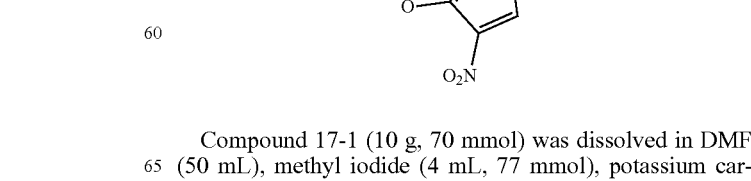
Example 17-2:
3-Methoxy-1-methyl-4-nitro-1H-pyrazole
Compound 17-1 (10 g, 70 mmol) was dissolved in DMF (50 mL), methyl iodide (4 mL, 77 mmol), potassium carbonate (14.8 g, 105 mmol) were added, under nitrogen atmosphere. The reaction mixture was stirred for 2 hours at 25° C. After the reaction was completed, monitored by TLC, then the reaction mixture was cooled to room temperature. The reaction solution was poured into water (50 mL), extracted with ethyl acetate (50 mL×2). The combined organic phases were washed with water (100 mL) and saturated brine (100 mL) sequentially, and dried with anhydrous sodium sulfate, then filtered. The filtrate was evaporated under reduced pressure. The crude product was purified by column (petroleum ether/ethyl acetate=1/1) to give a pale yellow solid 17-2 (8.9 g, yield 81%).

$^1$H NMR (400 MHz, CDCl$_3$) δ 7.92 (s, 1H), 3.96 (s, 3H), 3.73 (s, 3H).

Example 17-3: 3-Methoxy-1-methyl-1H-pyrazol-4-amine

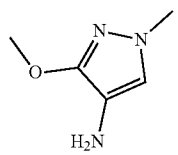

Compound 17-2 (8.9 g, 57 mmol) was dissolved in methanol (50 mL). After Pd/C (0.9 g) was added under hydrogen atmosphere, the reaction solution was stirred at 25° C. for 4 hours. After the reaction was completed, monitored by LCMS, then the reaction solution was filtered. The obtained filtrate was evaporated under reduced pressure to afford a dark red liquid 17-3 (6.6 g, 91%). ESI-MS m/z=128[M+H]$^+$.

$^1$H NMR (400 MHz, DMSO) δ 6.90 (s, 1H), 3.74 (s, 3H), 3.52 (s, 3H), 3.31 (s, 2H).

Example 17-5: 2-Chloro-5-fluoro-4-((4-methoxybenzyl)oxo)pyrimidine

Tetrahydrofuran (50 mL) was slowly dropped into a three-necked flask containing NaH (3.7 g, 89.9 mmol) at 0° C. under nitrogen atmosphere. After addition, the solution of PMBOH (9.9 g, 71.9 mmol) in tetrahydrofuran (50 mL) was slowly dropped into the reaction solution at 0° C. Then the reaction solution was maintained at 0° C. for 30 minutes. The mixture was slowly dropped into the solution of 17-4 (10.0 g, 59.9 mmol) in tetrahydrofuran (50 mL) at −20° C. After addition, the reaction solution was maintained at −20° C.-0° C. for 1 hour, monitored by LC-MS. After the reaction was completed, the reaction solution was slowly poured into saturated ammonium chloride aqueous solution (100 mL), extracted with ethyl acetate (100 mL×2), dried over anhydrous sodium sulfate. The filtrate was evaporated under reduced pressure to remove the solvent. The crude product was purified by column (petroleum ether/ethyl acetate=1/1) to provide 17-5 as a pale yellow solid (14.0 g, 87.1% yield).

LC-MS: LC-MS (ESI): m/z (M+H)$^+$ 269.0.

Example 17-6: 5-Fluoro-N-(3-methoxy-1-methyl-1H-pyrazol-4-yl)-4-((4-methoxybenzyl)oxo)pyrimidine-2-amine

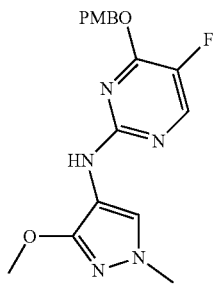

A solution of 17-5 (2.0 g, 7.5 mmol), 17-3 (0.95 g, 7.5 mmol), Pd$_2$(dba)$_3$ (0.13 g, 0.15 mmol), BINAP (0.18 g, 0.30 mmol), cesium carbonate (4.8 g, 15.0 mmol) in toluene (10 mL) was heated to 100° C. under nitrogen protection, and maintained for 3 hours. The reaction solution was monitored by LC-MS. After the reaction was completed, water (200 mL) was added to the reaction solution, and extracted with ethyl acetate (200 mL×2). The combined organic layers were washed with brine, dried over anhydrous sodium sulfate. The filtrate was evaporated under reduced pressure to remove the solvent. The crude product was purified by column (petroleum ether/ethyl acetate=1/1) to provide 17-6 as a yellow solid (2.0 g, 74.7% yield).

LC-MS: LC-MS (ESI): m/z (M+H)$^+$ 360.0.

Example 17-7: 5-Fluoro-2-((3-methoxy-1-methyl-1H-pyrazol-4-yl)amino) pyrimidine-4-phenol

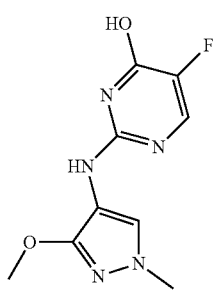 [SMILES: COc1nn(C)cc1Nc1ncc(F)c(O)n1]

17-6 (2.0 g, 5.6 mmol) was added to the solution of 4N hydrochloric acid in 1,4-dioxane (20 mL). The resulting mixture was stirred at room temperature for thirty minutes, and monitored by LC-MS. After the reaction, the solvent was distilled off under reduced pressure. Ethyl acetate (20 mL) was added to the crude product for recrystallization to provide 17-7 as a yellow solid (1.0 g, 75.0% yield). LC-MS (ESI): m/z (M+H)$^+$ 240.1.

Example 17-8: 4-Chloro-5-fluoro-N-(3-methoxy-1-methyl-1H-pyrazol-4-yl)pyrimidin-2-amine

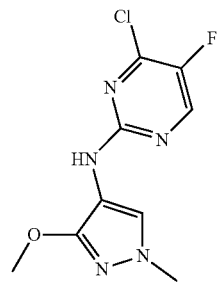 [SMILES: COc1nn(C)cc1Nc1ncc(F)c(Cl)n1]

A solution of 17-7 (1.0 g, 4.2 mmol) in phosphorus oxychloride (10 ml) was heated to 80° C. and maintained for 3 hours, and monitored by LC-MS. After the reaction was completed, the phosphorus oxychloride was evaporated to residue. The crude product was extracted with saturated sodium bicarbonate solution (50 mL) and dichloromethane (50 mL*2). The combined organic layers were washed with brine, dried over anhydrous sodium sulfate. The filtrate was evaporated under reduced pressure to remove the solvent. The crude product was purified by column (petroleum ether/ethyl acetate=1/1) to provide 17-8 (1.0 g, 92.9% yield) as a yellow solid LC-MS: LC-MS (ESI): m/z (M+H)+ 258.2.

Example 17-9: 4-(7-Chloro-1-tosyl-1H-pyrrolo[2,3-c]pyridin-3-yl)-5-fluoro-N-(3-methoxy-1-methyl-1H-pyrazol-4-yl)pyrimidin-2-amine

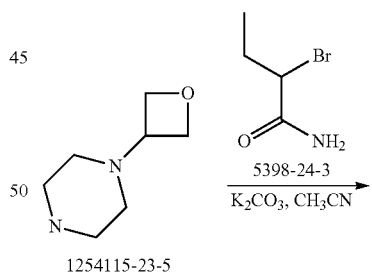

A solution of 17-8 (0.4 g, 1.6 mmol), 7A (0.88 g, 2.1 mmol), Pd(dppf)Cl$_2$ (0.11 g, 0.16 mmol), sodium carbonate (0.5 g, 4.8 mmol) in dioxane (10 mL) and water (2 mL) was heated to 90° C. under nitrogen atmosphere and maintained for 30 minutes. The reaction solution was monitored by LC-MS. After the reaction was completed, water (50 mL) was added to the reaction solution, and extracted with dichloromethane (50 mL*2). The combined organic layers were washed with brine, and dried over anhydrous sodium sulfate. The filtrate was evaporated under reduced pressure to remove the solvent. The crude product was purified by column (dichloromethane/methanol=10/1) to give 17-9 (0.56 g, 62.5% yield) as a white solid.

LC-MS (ESI): m/z (M+H)+ 528.1.

Example 17: N-(3-(5-Fluoro-2-((3-methoxy-1-methyl-1H-pyrazol-4-yl) amino)pyrimidin-4-yl)-1H-pyrrole[2,3-c]pyridin-7-yl)-2-(4-methylpiperazin-1-yl)butanamide

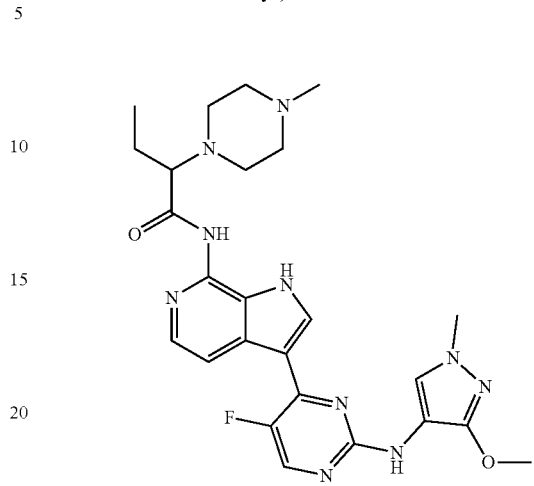

MS (ESI): m/z=523.50 [M+H]+.

$^1$HNMR (400 MHz, DMSO-d$_6$) δ 11.57 (s, 1H), 10.53 (s, 1H), 8.43 (s, 2H), 8.30 (d, J=3.8 Hz, 1H), 8.21 (s, 1H), 7.92 (s, 1H), 7.64 (s, 1H), 3.76 (s, 3H), 3.68 (s, 3H), 3.39 (s, 1H), 2.62 (d, J=18.9 Hz, 4H), 2.32 (s, 4H), 2.12 (s, 3H), 1.83-1.72 (m, 1H), 1.70-1.60 (m, 1H), 0.91 (t, J=7.4 Hz, 3H).

Example 18: N-(3-(2-((3-methoxy-1-methyl-1H-pyrazol-4-yl)amino)-5-methylpyrimidin-4-yl)-1H-pyrrolo[2,3-c]pyridin-7-yl)-2-(4-(oxbutan-3-yl) piperazin-1-yl)butanamide The target compound was prepared using a similar method to Example 2, replacing the corresponding starting materials.

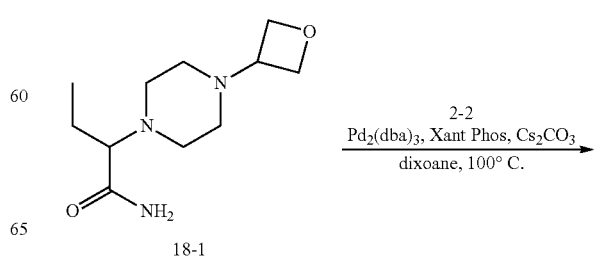

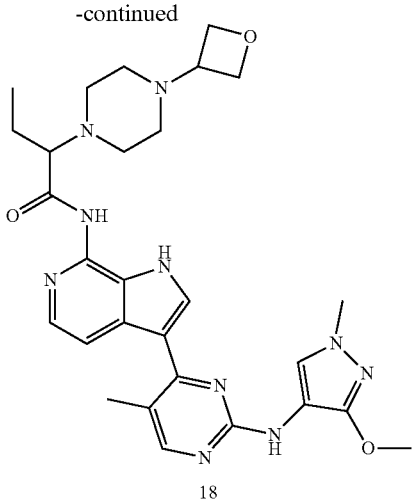

18

Example 18-1: 2-(4-(Oxbutacyclo-3-yl)piperazin-1-yl)butanamide

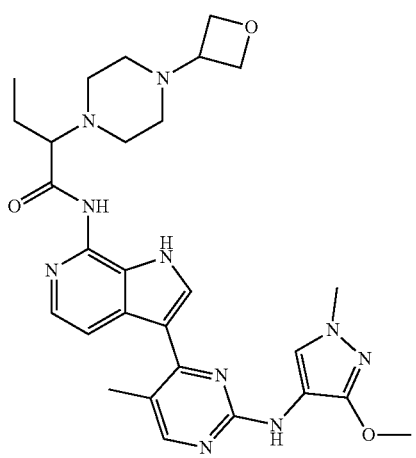 [SMILES: CCC(C(=O)Nc1nccc2c(-c3nc(Nc4cn(C)nc4OC)ncc3C)c[nH]c12)N1CCN(C2COC2)CC1]

To a solution of compound CAS:1254115-23-5 (300 mg, 2.11 mmol), 2-bromobutyramide (350 mg, 2.11 mmol) in acetonitrile (5 mL) was added potassium carbonate (583 mg, 4.22 mmol). The mixture was heated at 60° C. for 16 hours. After the reaction liquid was cooled, the inorganic salt was filtered off and the mother liquor was concentrated. The residue was separated and purified on a reverse phase C-18 column (acetonitrile/ammonium bicarbonate aqueous solution) to provide the title compound 18-1 (400 mg, 83%) as a white solid. MS (ESI): m/z=228.1 [M+H]$^+$.

Example 18: N-(3-(2-((3-Methoxy-1-methyl-1H-pyrazol-4-yl)amino)-5-methylpyrimidin-4-yl)-1H-pyrrolo[2,3-c]pyridin-7-yl)-2-(4-(oxbutan-3-yl) piperazin-1-yl)butanamide To a solution of compound 2-2 (60 mg, 0.16 mmol), 17-10 (90 mg, 0.4 mmol), cesium carbonate (168 mg, 52 mmol) in anhydrous dioxane (3 mL) were added tris(dibenzylideneacetone)dipalladium (0) (30 mg, 0.032 mmol) and 4,5-bisdiphenylphosphine-9,9-dimethylxanthene (30 mg, 0.052 mmol). The reaction mixture was heated and sealed at 110° C. for 2 hours under nitrogen protection. The mixture was cooled and filtered, and washed with methanol. The filtrate was concentrated and purified by high performance liquid chromatography to give the title compound 18 (20 mg, 22%) as a pale yellow solid. MS (ESI): m/z=561.2 [M+H]$^+$.

$^1$H NMR (400 MHz, CD$_3$OD): δ 8.15-8.13 (m, 2H), 8.10 (s, 1H), 7.88 (d, J=6.4 Hz, 1H), 7.63 (s, 1H), 4.68 (t, J=6.4 Hz, 2H), 4.58 (t, J=6.4 Hz, 2H), 3.88 (s, 3H), 3.71 (s, 3H), 3.56-3.51 (m, 1H), 3.25-3.22 (m, 1H), 2.83-2.72 (m, 4H), 2.51-2.45 (m, 4H), 2.37 (s, 3H), 1.93-1.84 (m, 2H), 1.06 (t, J=7.2 Hz, 3H).

Example 19: N-(3-(2-((2-Fluoro-3-(methylsulfonyl)phenyl)amino)-5-methylpyrimidin-4-yl)-1H-pyrrolo[2,3-c]pyridin-7-yl)-2-(4-methylpiperazin-1-yl)butanamide

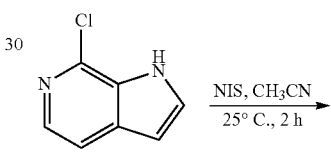

1-1

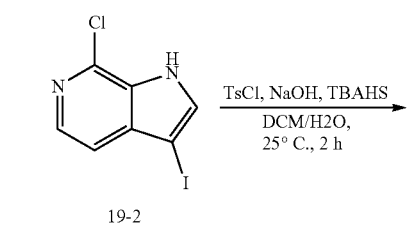

19-2

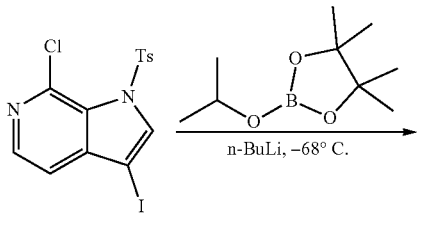

19-3

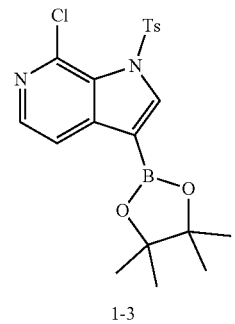

1-3

-continued
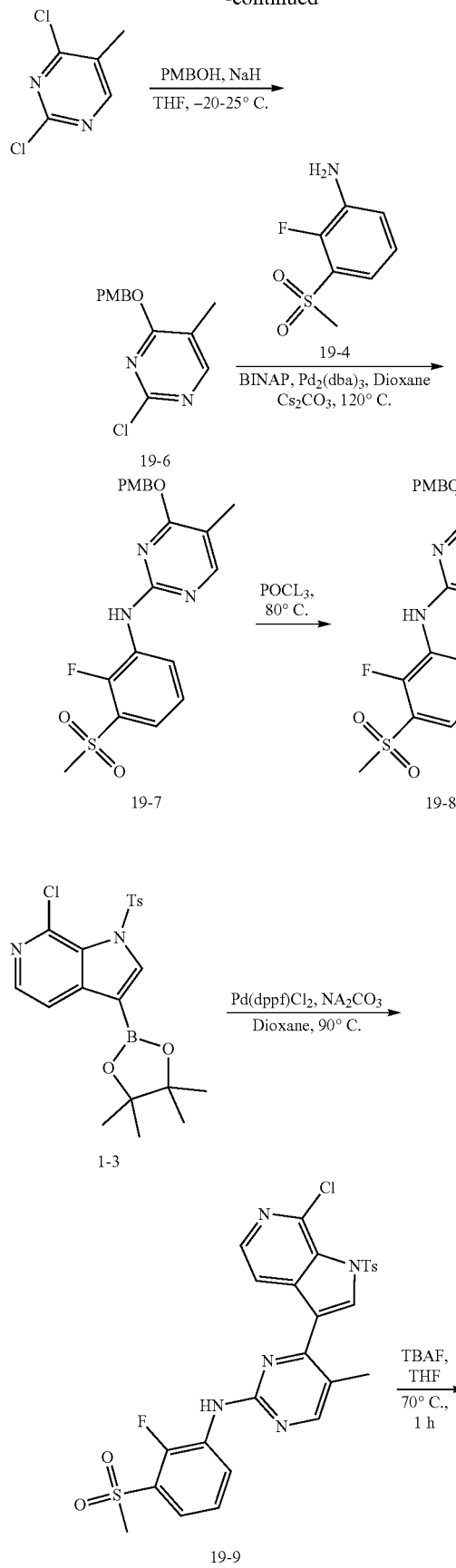
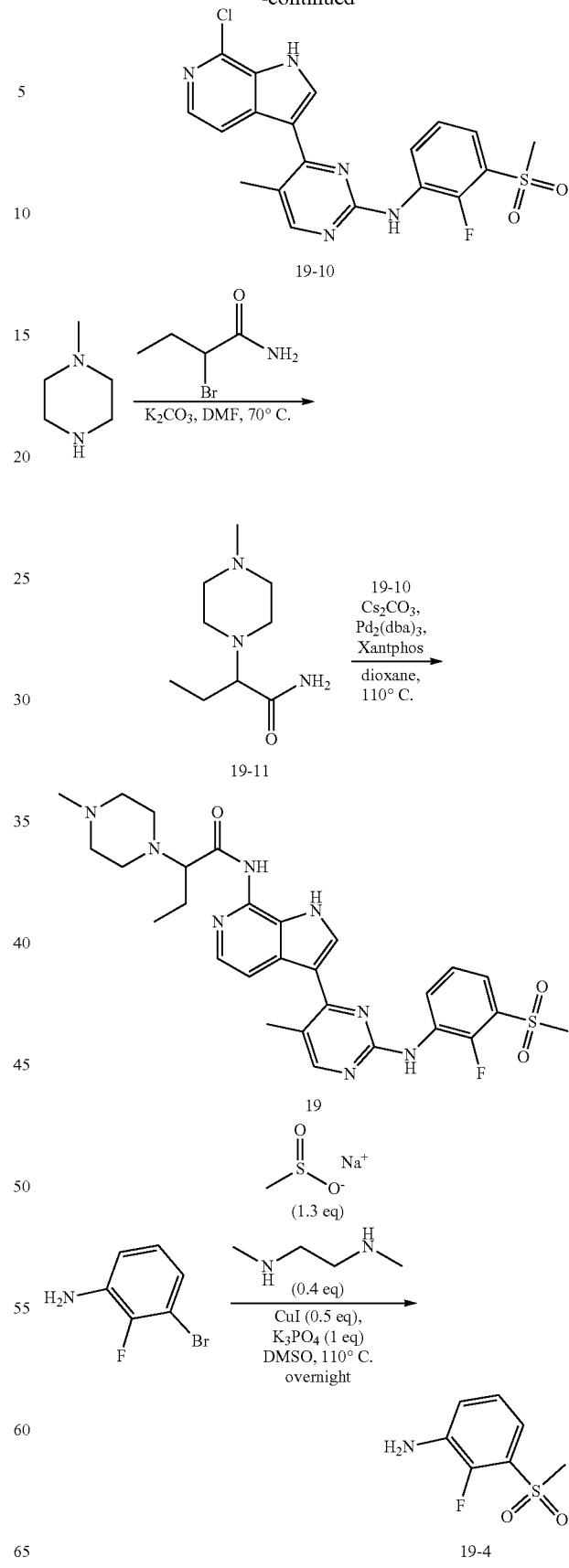

Example 19-2: 7-Chloro-3-iodo-1H-pyrrolo[2,3-c]pyridine

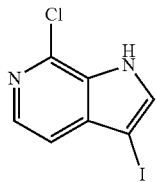

NIS (100 g, 450 mmol) was slowly added to the solution of 1-1 (57 g, 375 mmol) in acetonitrile (400 mL) under 0-25° C., and then the reaction was kept at 25° C. for 1 h, and monitored by LC-MS. After the reaction was completed, the solid was collected, washed with acetonitrile (50 ml), and dried to give 19-2 (85 g, 81.6% yield) as a white solid. LC-MS (ESI): m/z (M+H)$^+$ 279.1.

Example 19-3: 7-Chloro-3-iodo-1-tosyl-1H-pyrrolo[2,3-c]pyridine

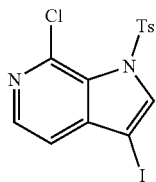 [SMILES: Cc1ccc(S(=O)(=O)n2cc(I)c3ccnc(Cl)c32)cc1]

To the solution of 19-2 (85 g, 305.8 mmol), sodium hydroxide (122.3 g, 3058 mmol) and tetrabutylammonium sulfide (10.3 g, 30.5 mmol) in dichloromethane (850 mL) and water (366 mL), TsCl (87.2 g, 458.7 mmol) was slowly added under 0° C. The reaction was kept at 25° C. for 2 hours and monitored by LC-MS. After the reaction, the aqueous layer was separated and extracted with dichloromethane (200 mL×2). The organic layers were combined, washed with saturated brine, dried over anhydrous sodium sulfate, and spin-dried. The concentrate was pulped with ethyl acetate (200 mL). The solid was collected and washed with ethyl acetate, and dried to provide 19-3 (85.0 g, 64.4% yield) as a white solid. LC-MS (ESI): m/z (M+H)$^+$ 433.1.

Example 1-3: 7-Chloro-3-(4,4,5,5-tetramethyl-1,3,2-dioxaborolan-2-yl)-1-toluenesulfonyl-1H-pyrrolo[2,3-c]pyridine

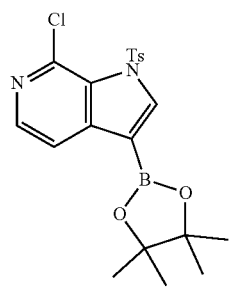 [SMILES: Cc1ccc(S(=O)(=O)n2cc(B3OC(C)(C)C(C)(C)O3)c3ccnc(Cl)c32)cc1]

Under 0° C., isopropyl magnesium bromide (1 M, 77.7 mL, 77.7 mmol) was slowly dropped into a solution of 19-3 (28.0 g, 64.8 mmol) in tetrahydrofuran (560 mL) within 30 minutes. Then the reaction solution was maintained at 0° C. for 30 minutes. The reaction solution was slowly dropped into isopropyl boronic acid pinacol ester (14.4 g, 77.8 mmol) at 0° C., and the reaction solution was maintained at 0° C. for 1 hour. After the reaction was completed, reaction solution was slowly poured into saturated ammonium chloride aqueous solution (560 mL), extracted with ethyl acetate (200 mL×2). The organic layers were combined, washed with saturated brine, dried with anhydrous sodium sulfate and spin-dried. The concentrate was recrystallized with acetonitrile (100 mL) to provide a white solid (12.0 g, 42.9% yield). LC-MS (ESI): m/z (M+H)$^+$ 433.1.

Example 19-4: 2-Fluoro-3-(methylsulfonyl)aniline

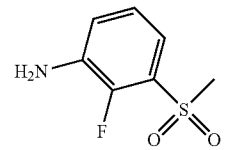

The compound 3-bromo-2-fluoroaniline (16 g, 84.2 mmol) was dissolved in dimethyl sulfoxide (80 mL), then sodium methanesulfinate (12.42 g, 109.5 mmol), N,N'-dimethylethylenediamine (3.62 mL, 33.68 mmol), cuprous iodide (8 g, 42.1 mmol) and potassium phosphate (22.3 g, 84.2 mmol) were added. The reaction solution was stirred at 110° C. for 16 hours. TLC showed that the reaction was completed, and the reaction mixture was cooled to room temperature, poured into water (300 mL), and extracted with ethyl acetate (200 mL×2). The organic layers was combined, washed with saturated brine (300 mL), dried over sodium sulfate and filtered. The filtrate was evaporated to remove solvent under reduced pressure. The crude product was purified by column (petroleum ether/ethyl acetate=1/1) to give compound 19-4 (7.36 g, yield 46.2%) as a yellow solid. ESI-MS m/z=190[M+H]$^+$

Example 19-6: 2-Chloro-4-((4-methoxybenzyl)oxo)-5-methylpyrimidine

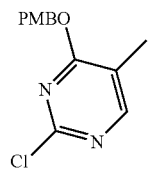

Tetrahydrofuran (100 mL) was slowly dropped into a three-necked flask containing NaH (11.1 g, 277.5 mmol) at 0° C. under nitrogen protection. After dripping, the solution of PMBOH (30.0 g, 217.4 mmol) in tetrahydrofuran (100 mL) was slowly dropped into the reaction solution at 0° C. Then the reaction solution was maintained at 0° C. for 30 minutes. Under −20° C., the mixture was slowly dropped into a solution of 2,4-dichloro-5-methylpyrimidine 19-5 (30.0 g, 84.0 mmol) in tetrahydrofuran (100 mL), then the reaction solution was maintained at −20° C.-0° C. for 1 hour and monitored by LC-MS. After the reaction was completed, the solution was slowly poured into saturated ammonium chloride aqueous solution (200 mL), extracted with ethyl acetate (200 mL×2), dried with anhydrous sodium sulfate and spin-dried. The concentrate was pulped with petroleum ether (300 mL). The white solid was collected, washed with petroleum ether (50 ml), and dried to give 19-6 (27.0 g, 55.6% yield) as a white solid. LC-MS (ESI): m/z (M+H)$^+$ 265.1.

Example 19-7: N-(2-Fluoro-3-(methylsulfonyl)phenyl)-4-((4-methoxybenzyl) oxo)-5-methylpyrimidin-2-amine

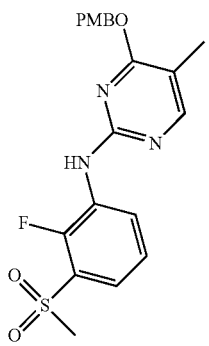

The solution of 19-6 (27.0 g, 102.7 mmol), YN-HDB-107 (19.0 g, 102.7 mmol), Pd$_2$(dba)$_3$ (2.7 g, 3.0 mmol), BINAP (3.7 g, 6.0 mmol), cesium carbonate (66.3 g, 204.0 mmol) in toluene (100 mL) was heated to 120° C. under nitrogen atmosphere, and maintained for 30 minutes. The reaction solution was monitored by LC-MS. After the reaction, water (200 mL) was added to the reaction solution and extracted with ethyl acetate (200 mL*2). The organic layer was combined, washed with brine, dried over anhydrous sodium sulfate, and evaporated. The concentrate was recrystallized with methyl tert-butyl ether (500 mL) to provide 19-7 (25.0 g, 58.8% yield) as a white solid. LC-MS (ESI): m/z (M+H)$^+$ 418.7.

Example 19-8: 4-Chloro-N-(2-fluoro-3-(methylsulfonyl)phenyl)-5-methylpyrimidin-2-amine

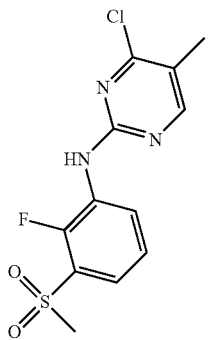 [SMILES: Cc1cnc(Nc2cccc(S(C)(=O)=O)c2F)nc1Cl]

A solution of 19-7 (25.0 g, 60.0 mmol) in phosphorus oxychloride (125 ml) was heated to 80° C. and maintained at this temperature for 3 hours. The reaction solution was monitored by LC-MS. After the reaction, the phosphorus oxychloride was evaporated to residue. The residue was dissolved in dichloromethane (200 ml), and the mixture was adjusted to pH 8 with saturated sodium bicarbonate solution. The organic layer was separated, and the aqueous layer was extracted once with dichloromethane (50 ml). The organic layers were combined, dried with anhydrous sodium sulfate, spin-dried. The concentrate was pulped with methyl tert-butyl ether to provide 19-8 (16.0 g, 84.7% yield) as a white solid. LC-MS (ESI): m/z (M+H)$^+$ 316.2.

Example 19-9: 4-(7-Chloro-1-tosyl-1H-pyrrolo[2,3-c]pyridin-3-yl)-N-(2-fluoro-3-(methylsulfonyl))phenyl)-5-methylpyrimidin-2-amine

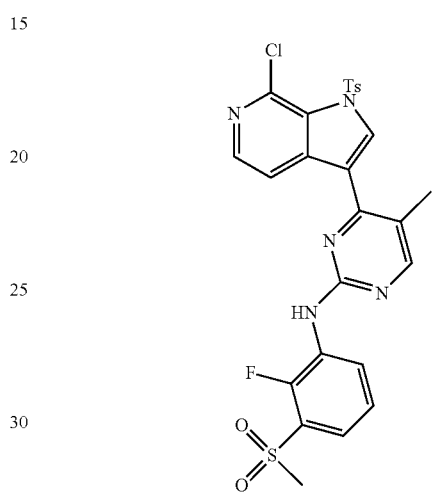

The solution of 1-3 (7.4 g, 17.0 mmol), 19-8 (2.7 g, 8.5 mmol), Pd(dppf)Cl$_2$ (0.62 g, 0.85 mmol) and sodium carbonate (3.6 g, 64.0 mmol) in dioxane (74 ml) and water (7.4 ml) were heated to 90° C. under nitrogen atmosphere and maintained at 90° C. for 1 hour. The reaction was monitored by LC-MS. After the reaction was completed, the dioxane was concentrated to dryness. The concentrate was dissolved in dichloromethane (50 ml) and water (10 ml). The organic layer was separated, and the aqueous layer was extracted with dichloromethane (20 ml*2). The organic layers were combined, dried with anhydrous sodium sulfate, and spin-dried. The concentrate was purified by column chromatography (elution solvent: 0-5% methanol in dichloromethane) to provide 19-9 as a white solid (4.5 g, 45.3% yield). LC-MS (ESI): m/z (M+H)$^+$ 586.1.

Example 19-10: 4-(7-Chloro-1H-pyrrolo[2,3-c]pyridin-3-yl)-N-(2-fluoro-3-(methylsulfonyl)phenyl)-5-methylpyrimidin-2-amine

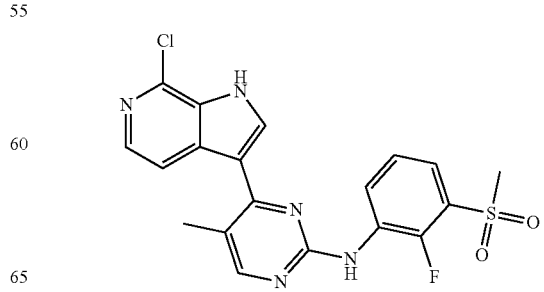

To a solution of 19-9 (1500 mg, 2.56 mmol) in tetrahydrofuran (15 ml) was added the solution of tetrabutylammonium bromide in tetrahydrofuran (1M) (5.12 ml, 5.12 mmol), and heated at 70° C. for 1 hour. After the reaction was completed, the solution was concentrated and purified on a silica gel column (mobile phase dichloromethane:methanol=10:1) to obtain the title compound (850 mg, 77%) as a yellow solid.

MS(ESI): m/z=431.8 [M+H]$^+$.

Example 19-11:
2-(4-Methylpiperazin-1-yl)butanamide

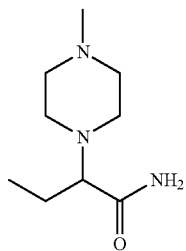

The compound 1-methylpiperazine (3.8 g, 38 mmol) was dissolved in N,N-dimethylformamide (50 ml), and the compound 2-bromobutanamide (15.8 g, 95 mmol) and potassium carbonate (10.5 g, 76 mmol) were added. The reaction solution was stirred at 70° C. for 16 hours. LCMS showed that the reaction was completed, the solution was cooled to room temperature, poured into water (200 ml), and extracted with ethyl acetate (100 ml*2). The organic layers were combined, washed with saturated brine (50 ml), and dried with anhydrous sodium sulfate. The reaction mixture was filtered, and the filtrate was evaporated under reduced pressure to remove the solvent. The crude product was purified by column (dichloromethane/methanol=0-50%) to obtain compound (2) as a white solid (7.4 g, yield 100%).

ESI-MS m/z=186[M+H]$^+$

Example 19: N-(3-(2-((2-Fluoro-3-(methylsulfonyl)phenyl)amino)-5-methylpyrimidin-4-yl)-1H-pyrrolo[2,3-c]pyridin-7-yl)-2-(4-methylpiperazin-1-yl)butanamide

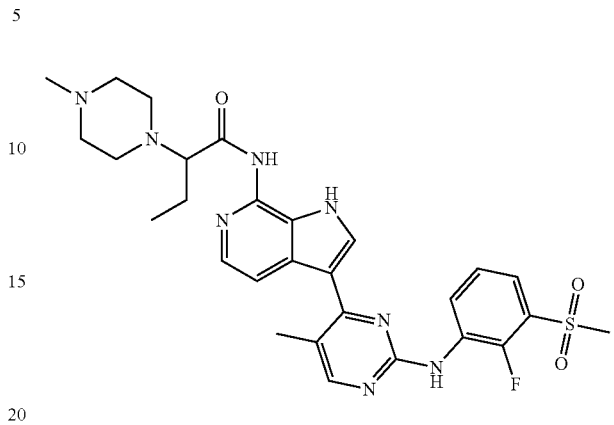

To a solution of 19-10 (52 mg, 0.12 mmol), 2-(4-methylpiperazin-1-yl)butanamide (33 mg, 0.18 mmol) and cesium carbonate (78 mg, 0.24 mmol) in 1,4-dioxane (1.5 ml) were added the solution of tris(dibenzylideneacetone)dipalladium (22 mg, 0.024 mmol) and 4,5-bis(diphenylphosphino)-9,9-dimethylxanthene (28 mg, 0.048 mmol). The reaction was heated overnight at 110° C. under nitrogen atmosphere. After the reaction was completed, the solution was filtered through celite. The filtrate was concentrated and purified on a reverse phase column (mobile phase: acetonitrile/ammonium bicarbonate aqueous solution) to provide the title compound 19 (24.4 mg, 34%) as a yellow solid.

MS (ESI): m/z=291.0 [M/2+H]$^+$.

$^1$HNMR (400 MHz, DMSO-d$_6$) δ 11.46 (s, 1H), 10.49 (s, 1H), 9.24 (s, 1H), 8.29 (s, 1H), 8.23 (t, J=7.2 Hz, 1H), 8.13 (s, 1H), 8.10 (d, J=5.5 Hz, 1H), 7.84 (d, J=5.6 Hz, 1H), 7.52 (t, J=6.5 Hz, 1H), 7.38 (t, J=7.9 Hz, 1H), 3.38 (s, 1H), 3.25 (s, 3H), 2.62 (d, J=16.1 Hz, 4H), 2.35 (s, 3H), 2.30 (s, 3H), 2.11 (s, 3H), 1.82-1.73 (m, 1H), 1.68-1.60 (m, 1H), 0.91 (t, J=7.4 Hz, 3H).

The following compounds were prepared with the method as described in Example 19:

| Number | Compound structure | LCMS, HNMR |
|---|---|---|
| 31 | 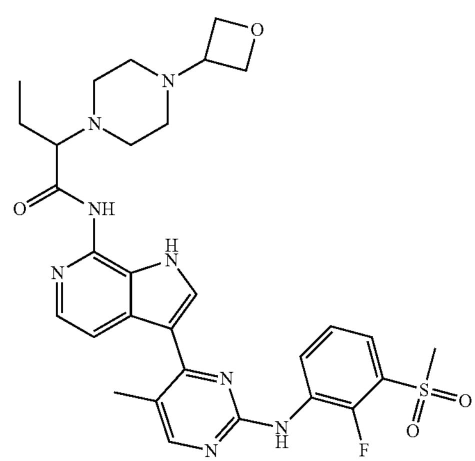 [SMILES: CCC(C(=O)Nc1nccc2c(-c3nc(Nc4cccc(S(C)(=O)=O)c4F)ncc3C)c[nH]c12)N1CCN(C2COC2)CC1] | MS (ESI): m/z = 623.1 [M + H]$^+$.<br>1H NMR (400 MHz, DMSO-d$_6$) δ 11.54-11.49 (m, 1H), 10.56 (s, 1H), 9.27 (s, 1H), 8.33 (s, 1H), 8.27 (s, 1H), 8.18 (d, J = 3.2 Hz, 1H), 8.14 (d, J = 5.6 Hz, 1H), 7.88 (d, J = 5.6 Hz, 1H), 7.56 (s, 1H), 7.43 (d, J = 8.0 Hz, 1H), 4.54-4.48 (m, 2H), 4.40 (t, J = 6.0 Hz, 2H), 3.48-3.42 (m, 1H), 3.40-3.35 (m, 1H), 3.29 (s, 3H), 2.69 (d, J = 17.2 Hz, 4H), 2.28 (s, 4H), 1.86-1.77 (m, 1H), 1.72-1.65 (m, 1H), 0.95 (t, J = 7.2 Hz, 3H). |

Example 20: (S)—N-(3-(2-((2-Fluoro-3-(methylsulfonyl)phenyl)amino)-5-methylpyrimidin-4-yl)-1H-pyrrolo[2,3-c]pyridin-7-yl)-2-(4-methylpiperazin-1-yl)butanamide

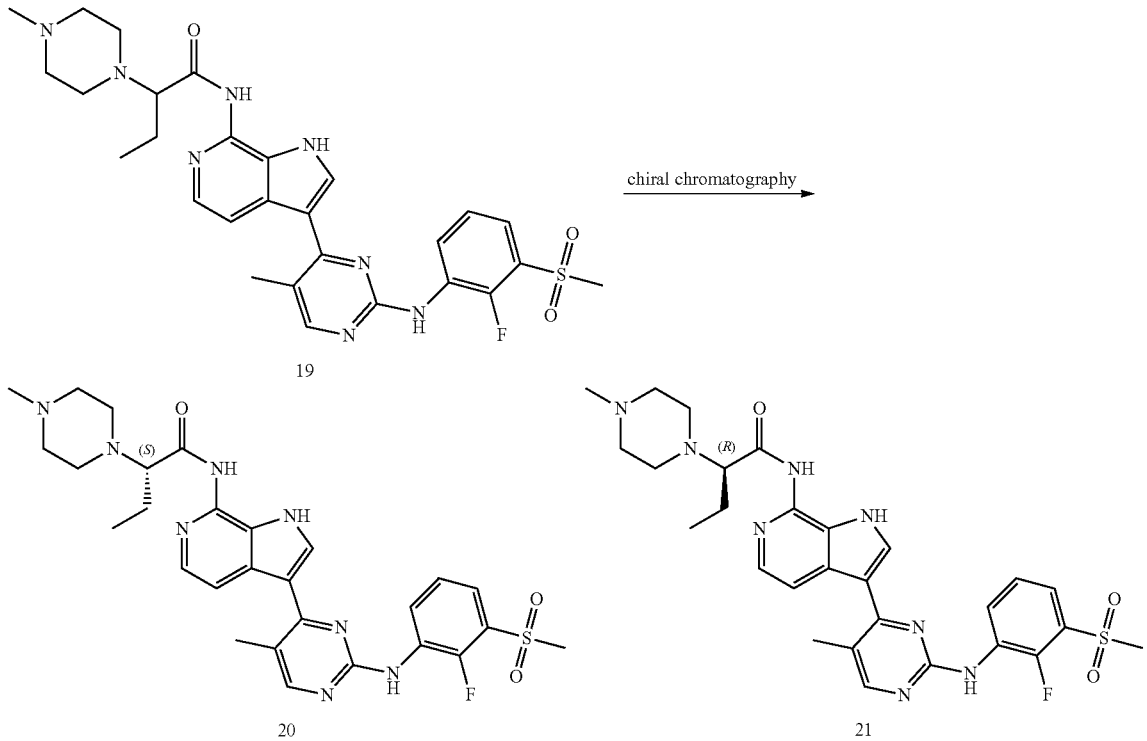

Example 20 (5.1 mg, 28%) was obtained from Example 19 (18 mg, 0.03 mmol) after chiral separation as a white solid and Example 21 (4.8 mg, 26%) as a yellow solid.

MS (ESI): m/z=291.0 [M/2+H]⁺.

¹HNMR (400 MHz, DMSO-d6) δ 11.46 (s, 1H), 10.49 (s, 1H), 9.24 (s, 1H), 8.29 (s, 1H), 8.23 (t, J=7.2 Hz, 1H), 8.14 (d, J=2.3 Hz, 1H), 8.10 (d, J=5.5 Hz, 1H), 7.84 (d, J=5.6 Hz, 1H), 7.52 (t, J=6.5 Hz, 1H), 7.38 (t, J=7.9 Hz, 1H), 3.38 (s, 1H), 3.25 (s, 3H), 2.62 (d, J=16.1 Hz, 4H), 2.35 (s, 3H), 2.30 (s, 3H), 2.11 (s, 3H), 1.82-1.73 (m, 1H), 1.68-1.60 (m, 1H), 0.91 (t, J=7.4 Hz, 3H).

Example 21: (R)—N-(3-(2-((2-Fluoro-3-(methylsulfonyl)phenyl)amino)-5-methylpyrimidin-4-yl)-1H-pyrrolo[2,3-c]pyridin-7-yl)-2-(4-methylpiperazin-1-yl)butanamide (ESI): m/z=291.0 [M/2+H]⁺.

¹HNMR (400 MHz, DMSO-d₆) δ 11.49 (s, 1H), 10.50 (s, 1H), 9.24 (s, 1H), 8.30 (s, 1H), 8.23 (t, J=7.1 Hz, 1H), 8.14 (s, 1H), 8.10 (d, J=5.5 Hz, 1H), 7.85 (d, J=5.6 Hz, 1H), 7.54-7.51 (m, 1H), 7.38 (t, J=8.0 Hz, 1H), 3.38 (s, 1H), 3.26 (s, 3H), 2.62 (d, J=15.6 Hz, 4H), 2.36 (s, 3H), 2.29 (s, 3H), 2.11 (s, 3H), 1.83-1.72 (m, 1H), 1.71-1.58 (m, 1H), 0.91 (t, J=7.4 Hz, 3H).

Example 22: N-(3-(2-((2-Fluoro-3-(methylsulfonylamino)phenyl)amino)-5-methylpyrimidin-4-yl)-1H-pyrrolo[2,3-c]pyridin-7-yl)-2-(4-methylpiperazin-1-yl)butanamide

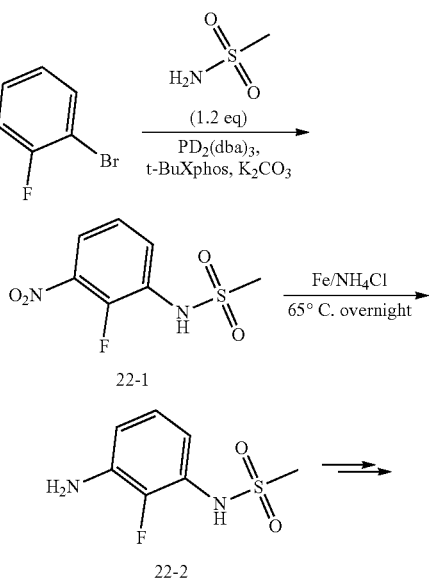

-continued

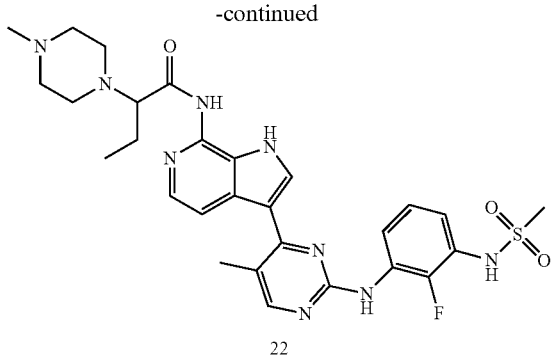

22

Example 22-1:
N-(2-Fluoro-3-nitrophenyl)methanesulfonamide

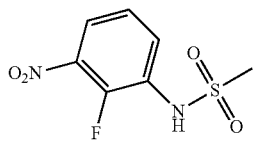

The compound 1-bromo-2-fluoro-3-nitrobenzene (1 g, 4.54 mmol) was dissolved in dioxane (15 ml). Methylsulfonamide (519 mg, 5.45 mmol), tris(dibenzylideneacetone) dipalladium (412 mg, 0.45 mmol), 2-di-tert-butylphosphine-2',4',6'-triisopropylbiphenyl (287 mg, 0.675 mmol) and potassium carbonate (1.24 g, 9 mmol) were added. The reaction solution was stirred at 80° C. for 2 hours. TLC showed that the reaction was completed, then the solution was evaporated to residue. The crude product was dissolved in ethyl acetate (20 ml) and water (30 ml) was added, and the mixture was separated. the water layer was adjusted to pH-4 with 2N hydrochloric acid (10 ml). The mixture was extracted with ethyl acetate (20 ml) and separated. The organic phase was dried over anhydrous sodium sulfate and filtered. The filtrate was evaporated under reduced pressure to provide compound 22-1 as a yellow solid (810 mg, yield 76.2%).

ESI-MS m/z=235[M+H]$^+$

Example 22-2:
N-(3-Amino-2-fluorophenyl)methanesulfonamide

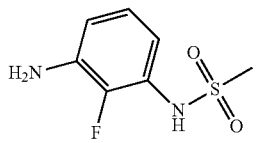

Compound (2) (810 mg, 1.65 mmol) was dissolved in tetrahydrofuran (8 ml), methanol (4 ml) and water (2 ml). Iron powder (970 mg, 17.3 mmol) and ammonium chloride (1.85 g, 34.6 mmol) were added, and the mixture was stirred at 65° C. for 16 hours. TLC showed that the reaction was completed, and the reaction solution was filtered by celite, the filtrate was evaporated under reduced pressure. The crude product was dissolved in ethyl acetate (20 ml) in which water (20 ml) was added and separated. The organic phase was dried over anhydrous sodium sulfate and filtered. The filtrate was evaporated under reduced pressure to remove the solvent. The crude product was purified by column (petroleum ether/ethyl acetate=1/1) to provide a yellow solid compound (3) (650 mg, yield 92%).

ESI-MS m/z=205[M+H]$^+$.

Example 22: N-(3-(2-((2-Fluoro-3-(methylsulfonylamino)phenyl)amino)-5-methylpyrimidin-4-yl)-1H-pyrrolo[2,3-c]pyridin-7-yl)-2-(4-methylpiperazin-1-yl)butanamide

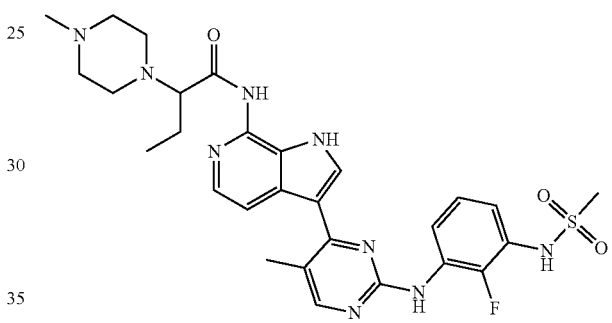

The target compound was obtained according to the method in Example 19, replacing the corresponding starting materials.

MS (ESI): m/z=298.5 [M/2+H]$^+$.
$^1$HNMR (400 MHz, DMSO-d$_6$) δ 11.43 (s, 1H), 10.58 (s, 1H), 9.60 (s, 1H), 8.91 (s, 1H), 8.25 (s, 1H), 8.11 (d, J=5.4 Hz, 2H), 7.85 (d, J=5.6 Hz, 1H), 7.70-7.62 (m, 1H), 7.11 (d, J=5.4 Hz, 2H), 3.44 (s, 1H), 2.97 (s, 3H), 2.70 (s, 8H), 2.36 (s, 3H), 2.34 (s, 3H), 1.85-1.74 (m, 1H), 1.71-1.57 (m, 1H), 0.92 (t, J=7.4 Hz, 3H).

Example 23: N-(3-(2-((2-Fluoro-3-(methylsulfonyl)phenyl)amino)-5-methylpyrimidin-4-yl)-1H-pyrrolo[2,3-c]pyridin-7-yl)-2-(8-methyl-3,8-diazabicyclo[3.2.1]octane-3-yl)butanamide

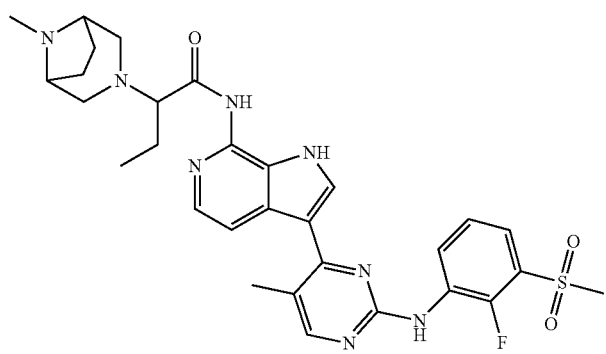

23 chiral chromatography →

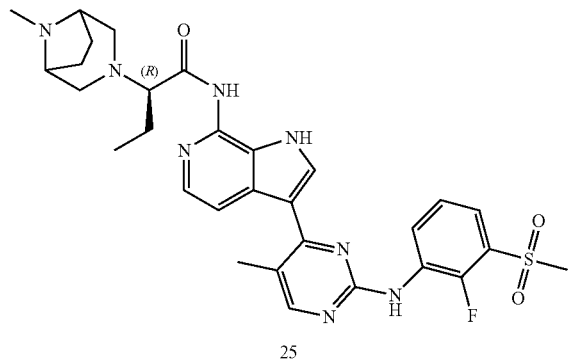

25

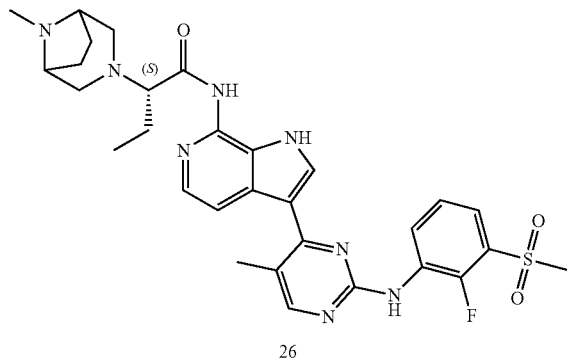

26

The target compound was obtained according to the method in Example 19, replacing the corresponding starting materials. Example 23 was chiral resolved to provide Example 25 and Example 26.

MS (ESI): m/z=304.0 [M/2+H]$^+$.

$^1$HNMR (400 MHz, DMSO-d$_6$) δ 11.44 (s, 1H), 10.68 (s, 1H), 9.25 (s, 1H), 8.30 (s, 1H), 8.22 (t, J=7.7 Hz, 1H), 8.11 (d, J=5.1 Hz, 2H), 7.86 (d, J=5.5 Hz, 1H), 7.53 (t, J=6.1 Hz, 1H), 7.39 (t, J=8.0 Hz, 1H), 3.83 (s, 2H), 3.25 (s, 3H), 2.79 (s, 2H), 2.59 (s, 3H), 2.36 (s, 3H), 2.04 (s, 2H), 1.95 (s, 2H), 1.78-1.71 (m, 1H), 1.68-1.60 (m, 1H), 1.30 (s, 1H), 1.20 (s, 1H), 1.19 (s, 1H), 0.93 (t, J=7.3 Hz, 3H).

Example 25: (R)—N-(3-(2-((2-Fluoro-3-(methylsulfonyl)phenyl)amino)-5-methylpyrimidin-4-yl)-1H-pyrrolo[2,3-c]pyridin-7-yl)-2-(8-methyl-3,8-diazabicyclo[3.2.1]octane-3-yl)butanamide MS (ESI): m/z=304.0 [M/2+H]$^+$.

$^1$HNMR (400 MHz, DMSO-d$_6$) δ 11.50 (s, 1H), 10.43 (s, 1H), 9.26 (s, 1H), 8.29 (s, 1H), 8.22 (t, J=7.7 Hz, 1H), 8.14 (s, 1H), 8.11 (d, J=5.4 Hz, 1H), 7.85 (d, J=5.6 Hz, 1H), 7.53 (t, J=6.4 Hz, 1H), 7.38 (t, J=8.0 Hz, 1H), 3.26 (s, 3H), 3.16 (s, 2H), 2.71 (s, 1H), 2.63 (s, 3H), 2.35 (s, 3H), 2.20 (s, 3H), 1.87 (s, 2H), 1.77-1.70 (m, 3H), 1.69-1.58 (m, 1H), 0.92 (t, J=7.3 Hz, 3H).

Example 26: (S)—N-(3-(2-((2-Fluoro-3-(methylsulfonyl)phenyl)amino)-5-methylpyrimidin-4-yl)-1H-pyrrolo[2,3-c]pyridin-7-yl)-2-(8-methyl-3,8-diazabicyclo[3.2.1]octane-3-yl)butanamide MS (ESI): m/z=304.0 [M/2+H]$^+$.

$^1$HNMR (400 MHz, DMSO-d$_6$) δ 11.51 (s, 1H), 10.40 (s, 1H), 9.26 (s, 1H), 8.29 (s, 1H), 8.23 (t, J=7.0 Hz, 1H), 8.14 (s, 1H), 8.11 (d, J=5.5 Hz, 1H), 7.85 (d, J=5.5 Hz, 1H), 7.53 (t, J=6.3 Hz, 1H), 7.38 (t, J=8.0 Hz, 1H), 3.26 (s, 3H), 3.08 (s, 2H), 2.68 (s, 1H), 2.59 (s, 3H), 2.35 (s, 3H), 2.15 (s, 3H), 1.85 (s, 2H), 1.77-1.70 (m, 3H), 1.64 (dd, J=14.0, 6.9 Hz, 1H), 0.92 (t, J=7.3 Hz, 3H).

Example 24: N-(3-(2-((2-Fluoro-3-(methylsulfonyl)phenyl)amino)-5-methylpyrimidin-4-yl)-1H-pyrrolo[2,3-c]pyridin-7-yl)-2-(7-methyl-2,7-diazaspiro[3.5]nonane-2-yl)butanamide

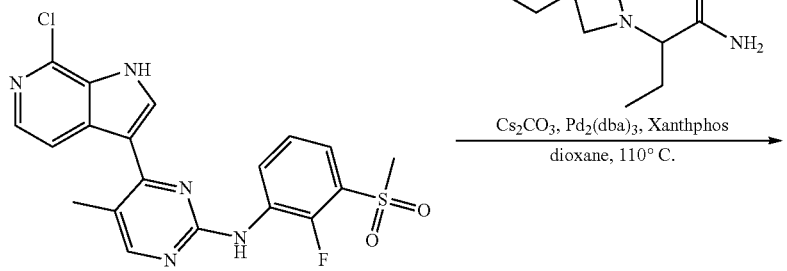

19-10

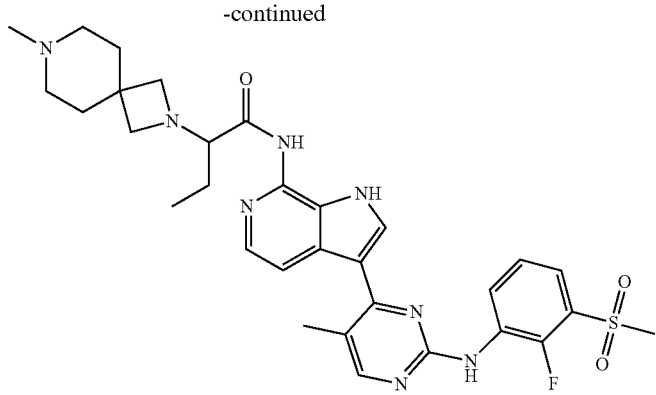
24
The target compound was obtained by using a method similar to that in Example 19, replacing the corresponding starting materials
MS (ESI): m/z=311.0 [M/2+H]⁺.
¹HNMR (400 MHz, DMSO-d₆) δ 11.52 (s, 1H), 10.08 (s, 1H), 9.25 (s, 1H), 8.30 (s, 1H), 8.22 (t, J=7.5 Hz, 1H), 8.13 (s, 2H), 7.85 (s, 1H), 7.53 (t, J=6.3 Hz, 1H), 7.38 (t, J=8.0 Hz, 1H), 3.26 (s, 3H), 3.14 (s, 6H), 2.87 (s, 4H), 2.52 (s, 2H), 2.36 (s, 3H), 1.87 (s, 4H), 1.62 (s, 2H), 0.88 (t, J=7.2 Hz, 3H).
Example 27: N-(3-(5-Fluoro-2-((2-fluoro-3-(methylsulfonyl)phenyl) amino)pyrimidin-4-yl)-1H-pyrrolo[2,3-c]pyridin-7-yl)-2-(4-methylpiperazin-1-yl)butanamide
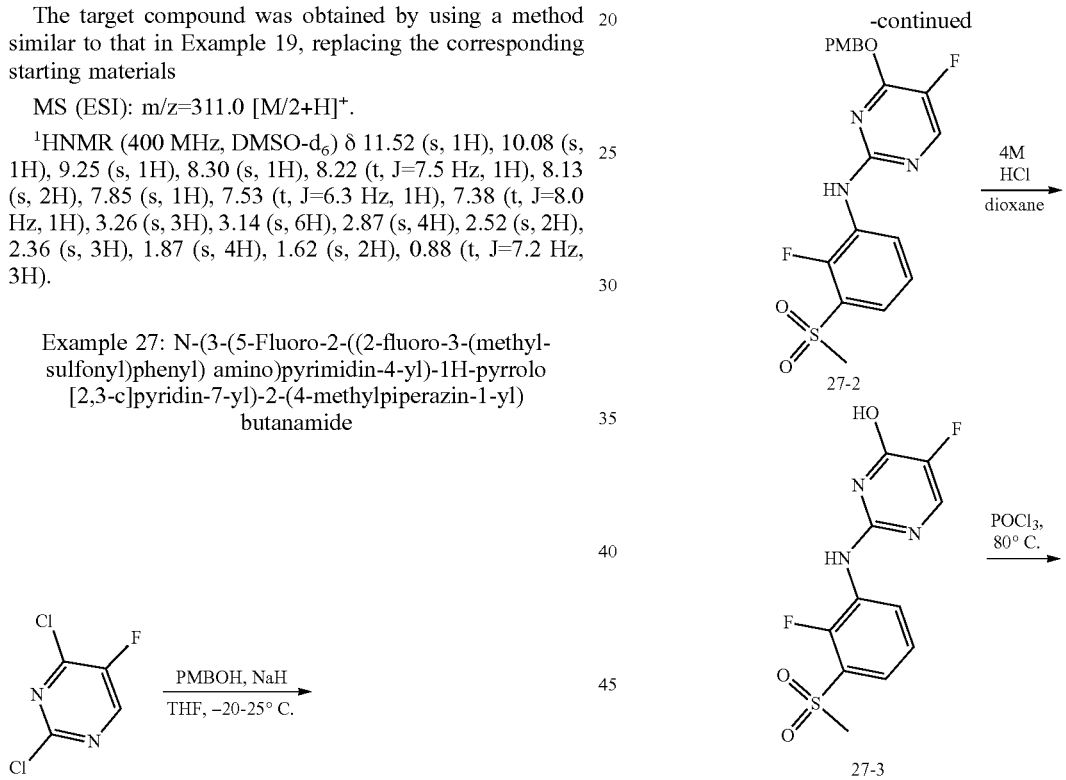

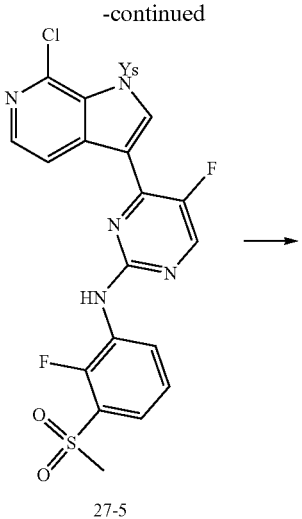

27-5

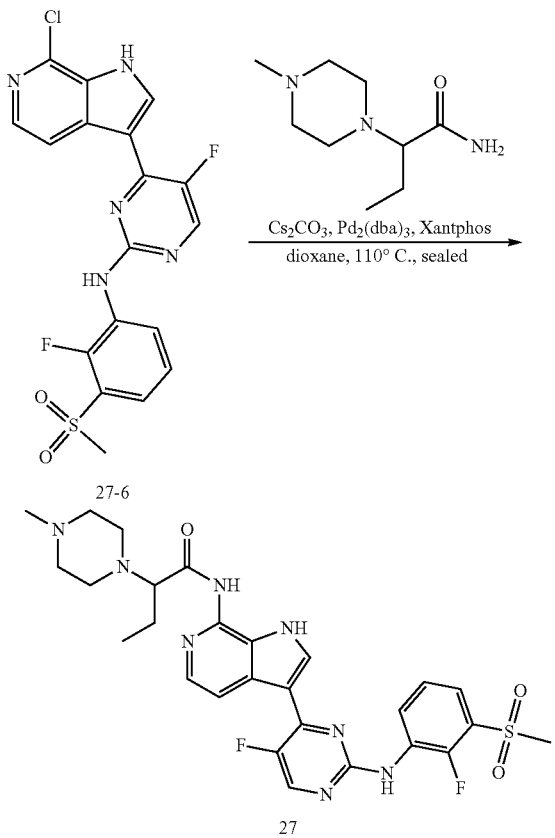

27-6

27

Example 27-1: 2-Chloro-5-fluoro-4-((4-methoxy-benzyl)oxo)pyrimidine

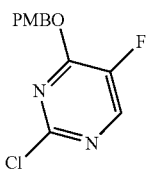

Tetrahydrofuran (50 mL) was slowly dropped into a three-necked flask containing NaH (3.7 g, 89.9 mmol) at 0° C. under nitrogen atmosphere. After dripping, the solution of PMBOH (9.9 g, 71.9 mmol) in tetrahydrofuran (50 mL) was slowly dropped into the reaction solution at 0° C. After dripping, the reaction solution was maintained at 0° C. for 30 minutes. The mixture was slowly dropped into the solution of 2,4-dichloro-5-fluoropyrimidine (10.0 g, 59.9 mmol) in tetrahydrofuran (50 mL) at −20° C. After dripping, the reaction solution was maintained at −20° C.-0° C. for 1 hour and monitored by LC-MS. After the reaction was completed, the mixture was slowly poured into saturated ammonium chloride aqueous solution (100 mL), extracted with ethyl acetate (100 mL×2), dried over anhydrous sodium sulfate. The filtrate was evaporated under reduced pressure to remove the solvent. The crude product was purified by column (petroleum ether/ethyl acetate=1/1) to provide 27-1 as a pale yellow solid (14.0 g, 87.1% yield). LC-MS (ESI): m/z (M+H)+ 269.0.

Example 27-2: 5-Fluoro-N-(2-fluoro-3-(methyl-sulfonyl)phenyl)-4-((4-methoxybenzyl)oxo)pyrimi-din-2-amine

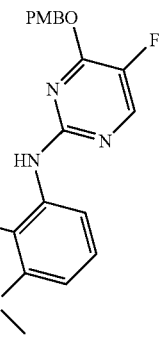

The solution of 27-1 (8.0 g, 29.8 mmol), 19-4 (5.6 g, 29.8 mmol), Pd$_2$(dba)$_3$ (0.54 g, 0.59 mmol), BINAP (0.74 g, 1.2 mmol), cesium carbonate (19.4 g, 59.6 mmol) in toluene (80 mL) was heated to 120° C. under nitrogen protection, and maintained at this temperature for 30 minutes. The reaction solution was monitored by LC-MS. After the reaction was completed, water (200 mL) was added to the reaction solution, and the mixture was extracted with ethyl acetate (200 mL×2). The organic layers were combined, washed with brine, dried over anhydrous sodium sulfate. The filtrate was evaporated under reduced pressure to remove the solvent. The crude product was purified by column (petroleum ether/ethyl acetate=1/1) to provide 27-2 (10.0 g, 79.9% yield) as a red oil.

LC-MS (ESI): m/z (M+H)+ 421.1.

Example 27-3: 5-Fluoro-2-((2-fluoro-3-(methylsulfonyl)phenyl)amino) pyrimidine-4-phenol

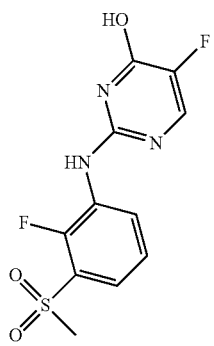 [SMILES: CS(=O)(=O)c1cccc(Nc2ncc(F)c(O)n2)c1F]

27-2 (2.0 g, 4.8 mmol) was added to 1,4-dioxane (15 ml) containing 4N hydrochloric acid and the mixture was stirred at room temperature for thirty minutes, and monitored by LC-MS. After the reaction was completed, the solvent was evaporated under reduced pressure. Ethanol (2 ml), ethyl acetate (20 ml), and methyl tert-butyl ether (20 ml) were added to the crude product for recrystallization to provide 27-3 (1.0 g, 68.8% yield) as a white solid. LC-MS (ESI): m/z (M+H)$^+$ 302.1.

Example 27-4: 4-Chloro-5-fluoro-N-(2-fluoro-3-(methylsulfonyl)phenyl) pyrimidin-2-amine

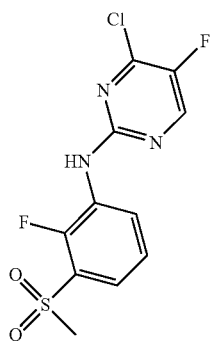 [SMILES: CS(=O)(=O)c1cccc(Nc2ncc(F)c(Cl)n2)c1F]

A solution of 27-3 (1.0 g, 3.3 mmol) in phosphorus oxychloride (20 ml) was heated to 80° C. and maintained at this temperature for 3 hours, and the reaction was monitored by LC-MS. After the reaction was completed, the phosphorus oxychloride was spin-dried. The crude product was purified by column (petroleum ether/ethyl acetate=1/1) to provide 27-4 (1.0 g, 97.8% yield) as a white solid. LC-MS (ESI): m/z (M+H)$^+$ 319.2.

Example 27-5: 4-(7-Chloro-1-tosyl-1H-pyrrolo[2,3-c]pyridin-3-yl)-5-fluoro-N-(2-fluoro-3-(methanesulfonyl)phenyl)pyrimidin-2-amine

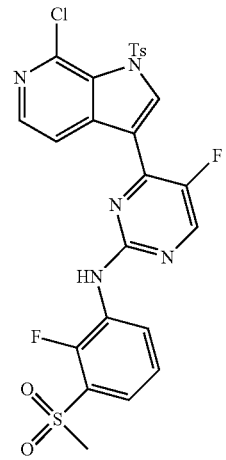 [SMILES: Cc1ccc(S(=O)(=O)n2cc(-c3nc(Nc4cccc(S(C)(=O)=O)c4F)ncc3F)c3ccnc(Cl)c32)cc1]

A solution of 27-4 (1.0 g, 3.1 mmol), 1-3 (1.3 g, 3.1 mmol), Pd(dppf)Cl$_2$ (0.21 g, 0.3 mmol), sodium carbonate (0.95 g, 9.0 mmol) in dioxane (10 ml) and water (2 ml) was heated to 90° C. under nitrogen atmosphere and maintained at this temperature for 30 minutes. The reaction solution was monitored by LC-MS. After the reaction, water (50 ml) was added to the reaction solution and the resulting mixture was extracted with dichloromethane (50 ml*2). The organic layers were combined, washed with brine, and dried with anhydrous sodium sulfate. The filtrate was evaporated under reduced pressure to remove the solvent. The crude product was purified by column (dichloromethane/methanol=10/1) to give a white solid 10 (0.6 g, 33.3% yield). LC-MS (ESI): m/z (M+H)$^+$ 589.0.

Example 27-6: 4-(7-Chloro-1-tosyl-1H-pyrrolo[2,3-c]pyridin-3-yl)-5-fluoro-N-(2-fluoro-3-(methanesulfonyl)phenyl)pyrimidin-2-amine

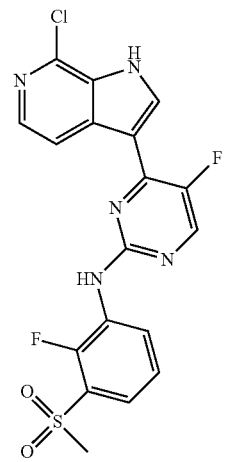 [SMILES: CS(=O)(=O)c1cccc(Nc2ncc(F)c(-c3c[nH]c4c(Cl)nccc34)n2)c1F]

The target compound was obtained using a similar method to Examples 19-0, replacing the corresponding starting materials.

MS (ESI): m/z=436.1 [M+H]+.

Example 27: N-(3-(5-Fluoro-2-((2-fluoro-3-(methylsulfonyl)phenyl)amino) pyrimidin-4-yl)-1H-pyrrolo[2,3-c]pyridin-7-yl)-2-(4-methylpiperazin-1-yl)butanamide

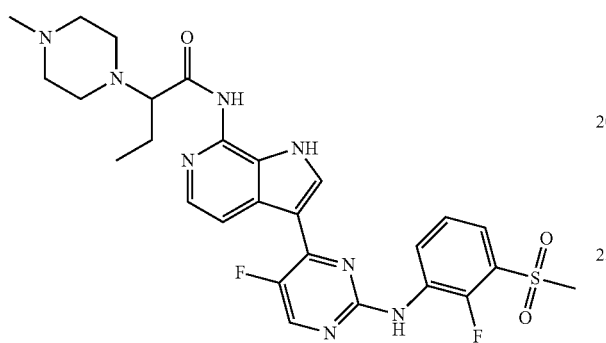

The target compound was obtained using a similar method to Example 17, replacing the corresponding starting materials.

MS (ESI): m/z=585.51 [M+H]+.

1HNMR (400 MHz, DMSO-d6) δ 11.66 (s, 1H), 10.56 (s, 1H), 9.53 (s, 1H), 8.46 (d, J=3.7 Hz, 1H), 8.27 (s, 1H), 8.22 (d, J=5.4 Hz, 1H), 8.18-8.11 (m, 2H), 7.91 (d, J=5.5 Hz, 1H), 7.60 (t, J=6.2 Hz, 1H), 7.44 (t, J=8.1 Hz, 1H), 3.40 (s, 1H), 3.29 (s, 3H), 2.64 (d, J=19.1 Hz, 4H), 2.36 (s, 4H), 2.15 (s, 3H), 1.84-1.73 (m, 1H), 1.69-1.64 (mz, 1H), 0.91 (t, J=7.4 Hz, 3H).

The following target compounds were obtained using a method similar to that in Example 17, replacing the corresponding starting materials.

Example 29: N-(7-(2-((2-Fluoro-3-(methylsulfonyl)phenyl)amino)-5-methylpyrimidin-4-yl)-5H-pyrrolo[3,2-d]pyrimidin-4-yl)-2-(4-methylpiperazin-1-yl)butanamide

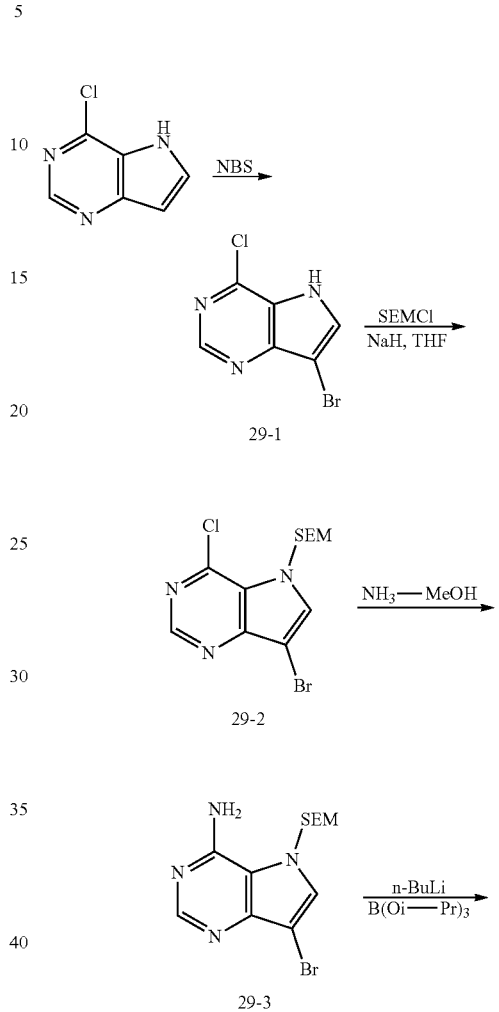

| Number | Compound structure | LCMS,HNMR |
|---|---|---|
| 28 | 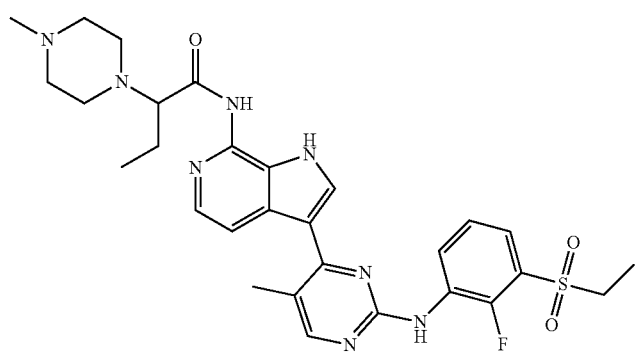 [SMILES: CCC(C(=O)Nc1nccc2c(-c3nc(Nc4cccc(S(=O)(=O)CC)c4F)ncc3C)c[nH]c12)N1CCN(C)CC1] | MS (ESI): m/z = 595.41 [M + H]+. 1HNMR (400 MHz, DMSO-d6) δ 11.46 (s, 1H), 10.49 (s, 1H), 9.22 (s, 1H), 8.30 (s, 1H), 8.24 (t, J = 7.1 Hz, 1H), 8.13 (d, J = 2.9 Hz, 1H), 8.10 (d, J = 5.5 Hz, 1H), 7.85 (d, J = 5.5 Hz, 1H), 7.51 (t, J = 6.2 Hz, 1H), 7.39 (t, J = 7.9 Hz, 1H), 3.39 (s, 1H), 3.33 (dd, J = 14.9, 7.5 Hz, 2H), 2.63 (d, J = 16.9 Hz, 4H), 2.35 (s, 7H), 2.12 (s, 3H), 1.83-1.73 (m, 1H), 1.70-1.60 (m, 1H), 1.09 (t, J = 7.4 Hz, 3H), 0.91 (t, J = 7.4 Hz, 3H). |

-continued

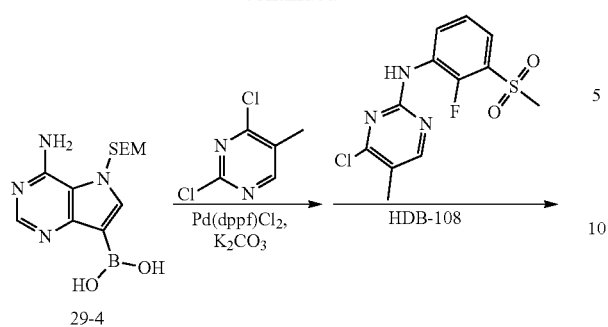

29-4

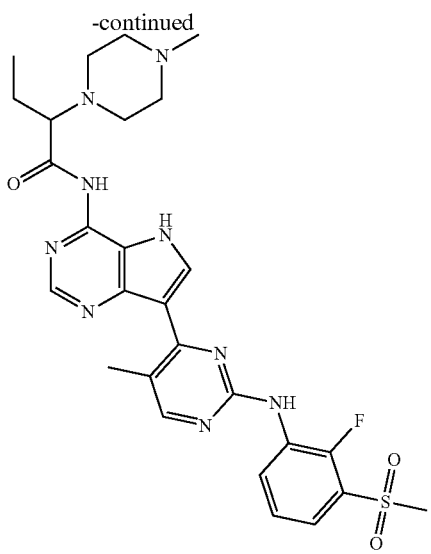

HDB-108

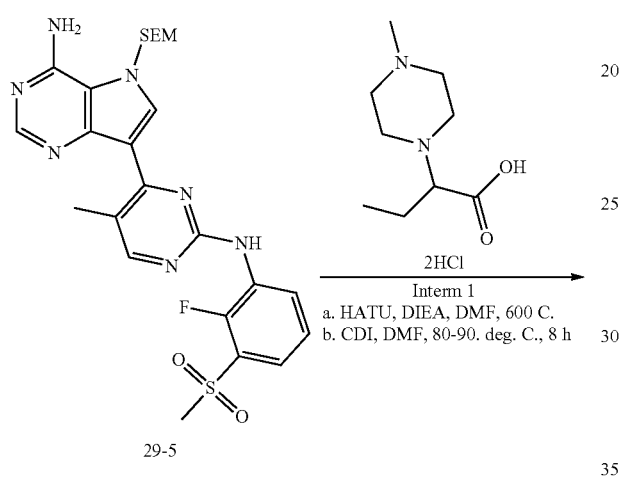

29-5

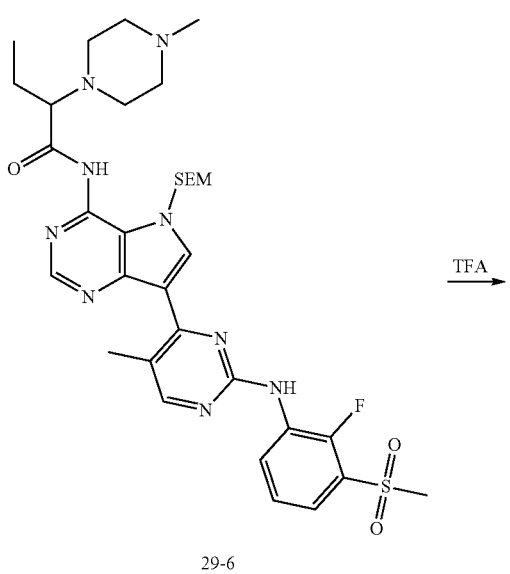

29-6

-continued

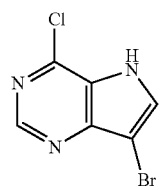

29

Example 29-1: 7-Bromo-4-chloro-5H-pyrrolo[3,2-d]pyrimidine

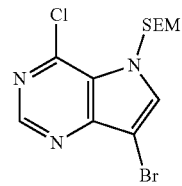 [SMILES: C[Si](C)(C)CCOCn1cc(Br)c2ncnc(Cl)c21]

At room temperature, to a mixture of 4-chloro-5H-pyrrolo[3,2-d]pyrimidine (2.00 g, 13.02 mmol) in acetonitrile (30 ml) was added N-bromosuccinimide (2.55 g, 14.33 mmol) in portions. Then trifluoroacetic acid (2.35 g, 20.6 mmol) was added to the reaction solution. The reaction solution was stirred at room temperature for 2 hours, and monitored by LCMS. The solid was collected by filtration, washed with dichloromethane, and dried to provide 7-bromo-4-chloro-5H-pyrrolo[3,2-d]pyrimidine 29-1 (2.60 g, yield: 85.9%). MS (ESI): m/z=231.7, 233.7 [M+H]$^+$.

Example 29-2: 7-Bromo-4-chloro-5-((2-(trimethylsilyl)ethoxy)methyl)-5H-pyrrolo[3,2-d]pyrimidine To a solution of 7-bromo-4-chloro-5H-pyrrolo[3,2-d]pyrimidine (2.00 g, 8.60 mmol) in anhydrous tetrahydrofuran (25 ml) was added sodium hydride (60%, 413 mg, 10.32 mmol) in batches under an ice bath. After the reaction solution was stirred at 0° C. for 20 minutes, a solution of 2-(chloromethoxy)ethyl) trimethylsilane (1.72 g, 10.32 mmol) in tetrahydrofuran (5 ml) was added dropwise to the reaction solution. After the reaction was stirred at 0° C. for 0.5 hour, the ice bath was removed and the reaction solution was stirred at room temperature for 1 hour. The reaction was monitored by TLC. The reaction solution was cooled to 0° C., quenched by adding saturated ammonium chloride (15 ml) solution. Then the reaction mixture was extracted with ethyl acetate (15 ml×3). The combined organic phase was washed successively with saturated brine (20 ml), and dried over anhydrous sodium sulfate. After filtration, the filtrate was concentrated under reduced pressure to provide an oily product. The oil was separated on a flash silica gel column (petroleum ether:ethyl acetate=10:1) to give 7-bromo-4-chloro-5-((2-(trimethylsilyl)ethoxy)methyl)-5H-pyrrolo[3, 2-d] pyrimidine 29-2 (2.40 g, yield: 76.9%) as a white solid. MS (ESI): m/z=361.7, 363.7. 7 [M+H]$^+$.

$^1$H NMR (400 MHz, CDCl$_3$) δ: 8.83 (s, 1H), 7.67 (s, 1H), 5.78 (s, 2H), 3.67 (t, J=12.0 Hz, 2H), 0.92 (t, J=12.0 Hz, 2H), −0.03 (s, 8H).

Example 29-3: 7-Bromo-5-((2-(trimethylsilyl) ethoxy)methyl)-5H-pyrrolo [3,2-d]pyrimidin-4-amine

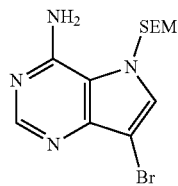 [SMILES: C[Si](C)(C)CCOCn1cc(Br)c2ncnc(N)c21]

7-Bromo-4-chloro-5-((2-(trimethylsilyl)ethoxy)methyl)-5H-pyrrolo[3,2-d] pyrimidine (1.00 g, 2.76 mmol) was added to a solution of ammonia in methanol (20 ml, 7.0 mol/L) in a sealed tube equipped with a magnetic stirrer. The reaction solution was placed in an oil bath at 80° C. and stirred for 16 hours. The reaction was tested by (TLC). After the reaction solution was cooled to room temperature, the mixture was concentrated under reduced pressure to provide a crude product. The crude product was separated on a quick silica gel column (petroleum ether:ethyl acetate=10:1) to provide 7-bromo-5-((2-(trimethylsilyl)ethoxy) methyl)-5H-pyrrolo[3,2-d]pyrimidin-4-amine 29-3 (816 mg, yield: 86.2%) as a white solid.

MS (ESI): m/z=342.8, 344.8 [M+H]$^+$.

$^1$H NMR (400 MHz, CDCl$_3$) δ: 8.45 (s, 1H), 5.97 (s, 2H), 5.46 (s, 2H), 3.62 (t, J=8.4 Hz, 2H), 0.97 (t, J=8.4 Hz, 2H), 0.00 (s, 9H).

Example 29-4: (4-Amino-5-((2-(trimethylsilyl) ethoxy)methyl)-5H-pyrrolo[3,2-d]pyrimidin-7-yl) boric Acid

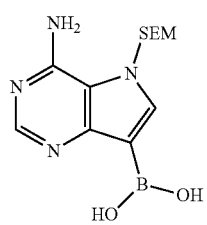 [SMILES: C[Si](C)(C)CCOCn1cc(B(O)O)c2ncnc(N)c21]

A solution of 7-bromo-5-((2-(trimethylsilyl)ethoxy) methyl)-5H-pyrrolo[3,2-d]pyrimidine-4-amine (645 mg, 1.88 mmol) in dry tetrahydrofuran (10 ml) was added into a three-necked flask (50 ml) equipped with a magnetic stirrer at room temperature. After exchanged with argon for three times, the reaction system was cooled to −78° C. Then, a solution of n-butyllithium (3.0 ml, 7.5 mmol, 2.5 mol/L) in n-hexane was added dropwise to the reaction solution. After dripping, the reaction solution was stirred at −78° C. for 30 minutes. Then a solution of triisopropyl borate (1.41 g, 7.52 mmol) in tetrahydrofuran (2.0 ml) was added dropwise into the mixture. The reaction solution was stirred at −78° C. for 1 hour. The reaction was monitored by LCMS. The reaction was quenched by adding saturated ammonium chloride (15 ml) solution, and then the resulting mixture was extracted with ethyl acetate (15 ml×3). The combined organic phase was washed successively with saturated brine (20 ml), and dried over anhydrous sodium sulfate. After filtration, the filtrate was concentrated under reduced pressure to obtain a crude product. The oily matter was separated on a reverse C-18 silica gel column (HCOOH) to provide 4-amino-5-((2-(trimethylsilyl) ethoxy)methyl)-5H-pyrrolo[3,2-d]pyrimidin-7-yl)boronic acid 29-4 (140 mg, yield 24%) as a white solid. MS (ESI): m/z=308.9 [M+H]$^+$.

Example 29-5: 7-(2-((2-Fluoro-3-(methylsulfonyl) phenyl)amino)-5-methylpyrimidin-4-yl)-5-((2-(trimethylsilyl)ethoxy)methyl)-5H-pyrrolo[3,2-d]pyrimidin-4-amine

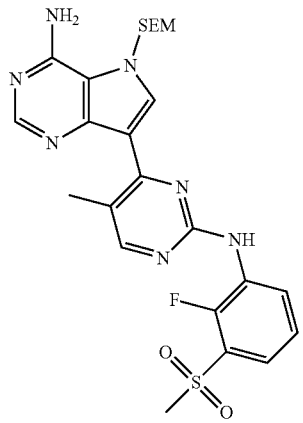 [SMILES: Cc1cnc(Nc2cccc(S(C)(=O)=O)c2F)nc1-c1cn(COCC[Si](C)(C)C)c2c(N)ncnc12]

To the mixture of 4-chloro-N-(2-fluoro-3-(methylsulfonyl)phenyl)-5-methylpyrimidin-2-amine (125 mg, 0.405 mmol), 4-amino-5-((2-(trimethylsilyl) ethoxy)methyl)-5H-pyrrolo[3,2-d]pyrimidin-7-yl)boronic acid (125 mg, 0.405 mmol), potassium phosphate (172 mg, 0.81 mmol) and 1,4-dioxane (3.0 ml)/water (1.0 ml) was added Pd(dppf) Cl$_2$.DCM (33 mg, 0.04 mmol) under argon atmosphere. The reaction solution was heated to 90° C. and stirred for 6 hours. The reaction was monitored by LCMS. After cooled to room temperature, the reaction solution was extracted with ethyl acetate (10 ml×2). The combined organic phase was dried over anhydrous sodium sulfate, filtered. The filtrate was concentrated under reduced pressure to obtain a crude product. The crude product was separated on a C-18 silica gel column (NH₄HCO₃) to provide 7-(2-((2-fluoro-3-(methanesulfonyl)phenyl)amino)-5-methylpyrimidin-4-yl)-5-((2-(trimethylsilyl)ethoxy)methyl)-5H-pyrrolo[3,2-d]pyrimidin-4-amine (96 mg, yield: 43.5%) as a pale yellow solid. MS (ESI): m/z=544.0[M+H]⁺.

Example 29: N-(7-(2-((2-Fluoro-3-(methylsulfonyl)phenyl)amino)-5-methylpyrimidin-4-yl)-5-((2-(trimethylsilyl)ethoxy)methyl)-5H-pyrrolo[3,2-d] pyrimidin-4-yl)-2-(4-methylpiperazin-1-yl)butanamide

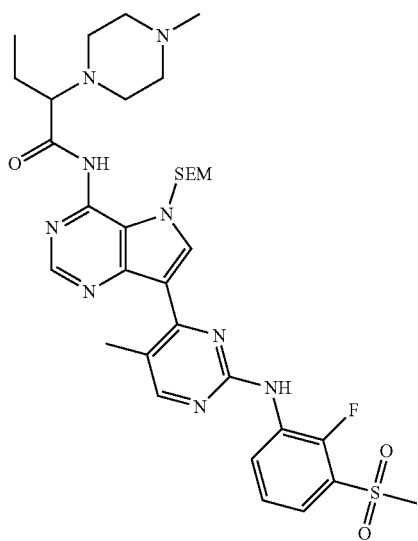 [SMILES: CCC(C(=O)Nc1ncnc2c(-c3nc(Nc4cccc(S(C)(=O)=O)c4F)ncc3C)cn(COCC[Si](C)(C)C)c12)N1CCN(C)CC1]

2-(4-Methylpiperazin-1-yl)butyric acid (143 mg, 0.551 mmol), N-ethyl-N-isopropylpropane-2-amine (119 mg, 0.92 mmol) and DMF (1.5 mL) was added into a round bottom flask (10 ml) equipped with magnetic stirrers at room temperature. After the stirrer started and exchanged with nitrogen for three times, dicarbonylimidazole (60 mg, 0.368 mmol) was added to the reaction solution. The reaction was placed in an oil bath at 80° C. and heated for 0.5 hours (until no gas evolution). The reaction solution was cooled to room temperature, and 7-(2-((2-fluoro-3-(methylsulfonyl)phenyl)amino)-5-methylpyrimidin-4-yl)-5-((2-(trimethylsilyl)ethoxy)methyl)-5H-pyrrolo[3,2-d]pyrimidin-4-amine (50 mg, 0.214 mmol) was added. Then, the reaction solution was heated and stirred in an oil bath at 90° C. for 8 hours. The reaction was detected by LCMS. The solution was separated by preparative high performance liquid chromatography (NH₄HCO₃) to provide a white solid N-(7-(2-((2-fluoro-3-(methylsulfonyl)phenyl)amino)-5-methylpyrimidine-4-yl)-5-((2-(trimethylsilyl)ethoxy)methyl)-5H-pyrrolo[3,2-d]pyrimidin-4-yl)-2-(4-methylpiperazin-1-yl) butanamide (22 mg, yield: 33.6%). MS (ESI): m/z=712.2 [M+H]⁺.

Example 29: N-(7-(2-((2-Fluoro-3-(methylsulfonyl)phenyl)amino)-5-methylpyrimidin-4-yl)-5H-pyrrolo[3,2-d)pyrimidin-4-yl)-2-(4-methylpiperazin-1-yl)butanamide

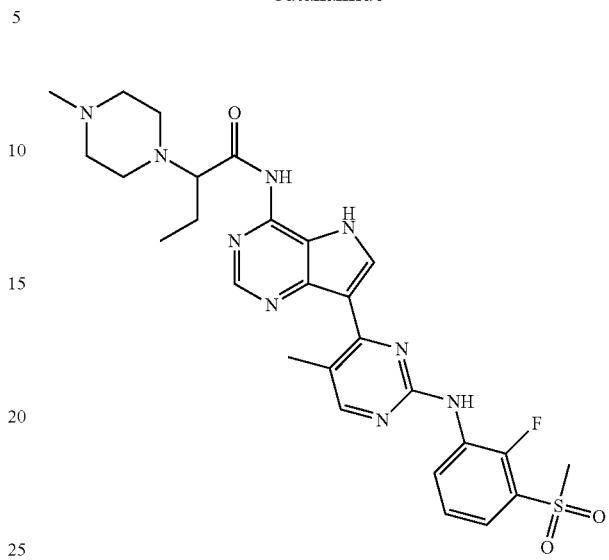

A solution of N-(7-(2-((2-fluoro-3-(methylsulfonyl)phenyl)amino)-5-methylpyrimidin-4-yl)-5-((2-(trimethylsilyl)ethoxy)methyl)-5H-pyrrolo[3,2-d]pyrimidin-4-yl)-2-(4-methylpiperazine-1-yl)butanamide (17 mg, 0.024 mmol) in trifluoroacetic acid (1.0 mL) was added into a 10 ml sealed tube equipped with a magnetic stirrer. The reaction solution was heated to 50° C. and stirred for 2 hours. The reaction was monitored by LCMS. After the reaction solution was cooled to room temperature, it was concentrated under reduced pressure to obtain a crude product. The solution was separated by preparative high performance liquid chromatography (NH4HCO3) to provide a white solid N-(7-(2-((2-fluoro-3-(methylsulfonyl)phenyl)amino)-5-methylpyrimidine-4-yl)-5H-pyrrolo[3,2-d]pyrimidin-4-yl)-2-(4-methylpiperazin-1-yl)butanamide (17 mg, yield: 72.2%). MS (ESI): m/z=582.0. [M+H]⁺.

¹H NMR (400 MHz, DMSO-d₆) δ 11.55 (s, 1H), 10.96 (s, 1H), 9.28 (s, 1H), 8.66 (s, 2H), 8.39 (s, 1H), 8.11 (s, 1H), 7.49-7.44 (m, 1H), 7.39 (t, J=8.0 Hz, 1H), 3.51 (s, 1H), 2.65 (d, J=18.4 Hz, 4H), 2.34 (s, 5H), 2.14 (s, 3H), 1.80 (dd, J=14.4, 7.0 Hz, 1H), 1.69 (dd, J=13.6, 6.9 Hz, 1H), 0.94 (t, J=7.2 Hz, 3H)

Example 30: 1-(3-(2-((2-Fluoro-3-(methylsulfonyl)phenyl)amino)-5-methylpyrimidin-4-v1)-1H-pyrrolo[2,3-c]pyridin-7-v1)-3-isopropylurea

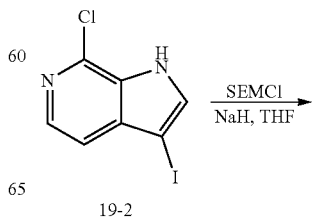

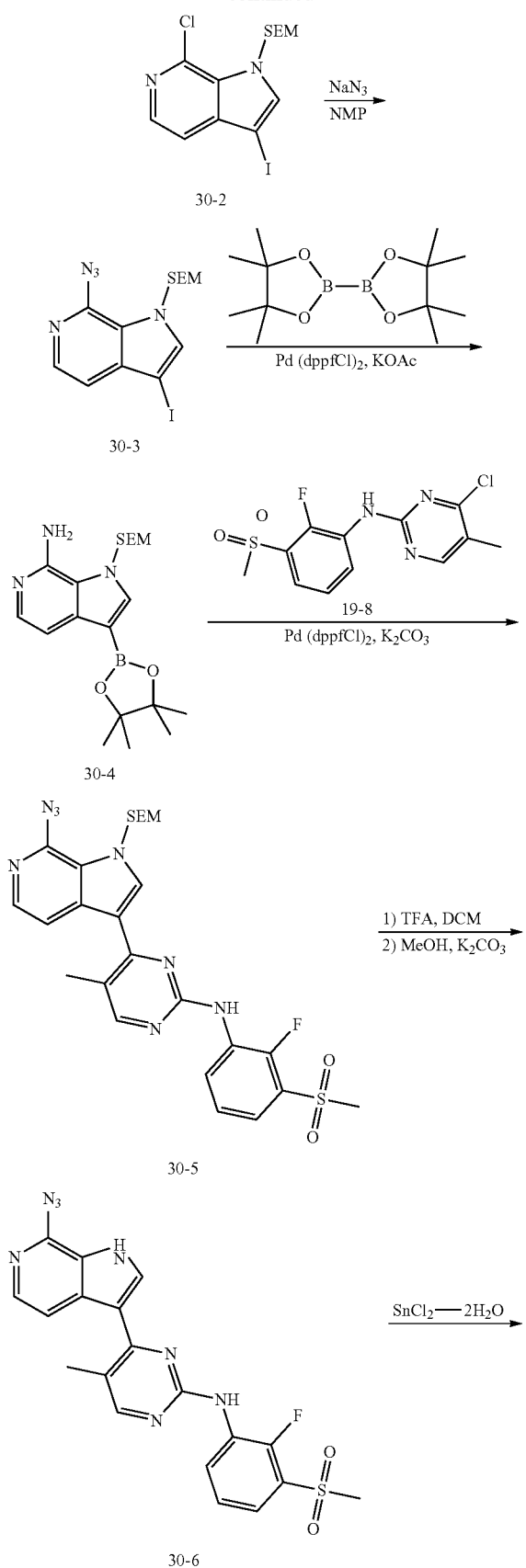

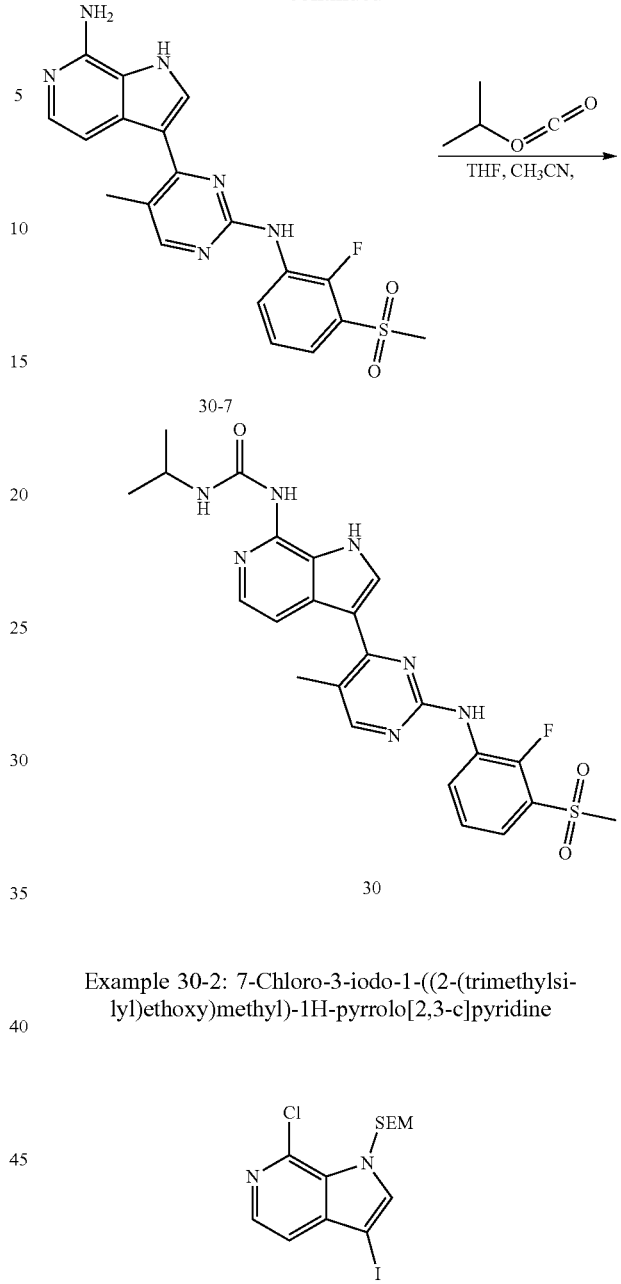

Example 30-2: 7-Chloro-3-iodo-1-((2-(trimethylsilyl)ethoxy)methyl)-1H-pyrrolo[2,3-c]pyridine To a solution of 7-chloro-3-iodo-1H-pyrrolo[2,3-c]pyridine (5.33 g, 19.14 mmol) in anhydrous tetrahydrofuran (55 ml) was added sodium hydride (60%, 919 mg, 22.97 mmol) in batches under ice-cooling. After the reaction solution was stirred at 0° C. for 20 minutes, a solution of (2-(chloromethoxy)ethyl) trimethylsilane (3.83 g, 22.97 mmol) in tetrahydrofuran (10 ml) was added dropwise to the reaction solution. After the reaction was stirred at 0° C. for 0.5 hour, the ice bath was removed and the reaction solution was stirred at room temperature for 16 hours. The reaction was monitored by TLC. The reaction mixture was cooled to 0° C., quenched by adding saturated ammonium chloride (30 ml) solution, and extracted with ethyl acetate (30 ml×3). The combined organic phase was washed with saturated brine (30 ml), and dried over anhydrous sodium sulfate successively. After filtration, the filtrate was concentrated under reduced pressure to obtain an oil. The oil was separated on a flash silica gel column (petroleum ether:ethyl acetate=10:1) to give a white solid 7-chloro-3-iodo-1-((2-(trimethylsilyl)ethoxy)methyl)-1H-pyrrolo[2,3-c]pyridine (6.02 g, yield: 77%). MS (ESI): m/z=408.7, 410.7 [M+H]+.

Example 30-3: 7-Azido-3-iodo-1-((2-(trimethylsilyl)ethoxy)methyl)-1H-pyrrolo[2,3-c]pyridine

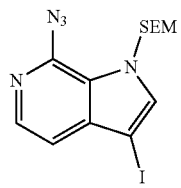 [SMILES: C[Si](C)(C)CCOCn1cc(I)c2ccnc(N=[N+]=[N-])c21]

7-Chloro-3-iodo-1-((2-(trimethylsilyl)ethoxy)methyl)-1H-pyrrolo[2,3-c]pyridine (3.40 g, 8.32 mmol), sodium azide (1.62 g, 24.95 mmol) and N-methylpyrrolidone (30 ml) was added into a sealed tube equipped with a magnetic stirrer. The reaction solution was placed in an oil bath at 180° C. and stirred for 1 hour. The reaction was detected by (TLC). After the reaction solution was cooled to room temperature, it was poured into 100 ml of water, and then extracted with ethyl acetate (30 ml×3). The combined organic phase was washed with water (30 ml*3), saturated brine (30 ml), and dried over anhydrous sodium sulfate. After filtration, the filtrate was concentrated under reduced pressure to provide an oily product, and separated to provide 7-azido-3-iodo-1-((2-(trimethylsilyl)ethoxy)methyl)-1H-pyrrolo[2,3-c]pyridine (1.97 g, yield: 57%) as a white solid. MS (ESI): m/z=415.8 [M+H]+.

Example 30-4: 7-Azido-3-(4,4,5,5-tetramethyl-1,3,2-dioxaborolan-2-yl)-1-((2-(trimethylsilyl)ethoxy)methyl)-1H-pyrrolo[2,3-c]pyridine

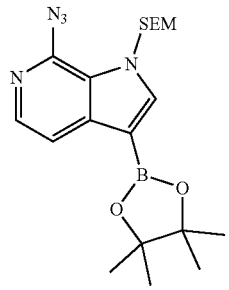 [SMILES: CC1(C)OB(c2cn(COCC[Si](C)(C)C)c3c(N=[N+]=[N-])nccc23)OC1(C)C]

To a mixture of 7-azido-3-iodo-1-((2-(trimethylsilyl)ethoxy)methyl)-1H-pyrrolo[2,3-c]pyridine (500 mg, 1.2 mmol), 4,4,4',4',5,5,5',5'-octamethyl-2,2'-bi(1,3,2-dioxaboropentane) (1.53 g, 6.00 mmol), anhydrous potassium acetate (590 mg, 6.00 mmol) and 1,4-dioxane (7.0 ml) was added Pd(dppf)Cl₂.DCM (95 mg, 1.20 mmol) under the argon atmosphere. The reaction solution was heated to 90° C. and stirred for 18 hours. The reaction was monitored by LCMS. After the reaction solution was cooled to room temperature, it was diluted with ethyl acetate (20 ml), filtered. The filtrate was concentrated under reduced pressure to provide a crude product. The crude product was purified on a flash silica gel column to provide 7-azide-3-(4,4,5,5-tetramethyl-1,3,2-dioxaborolan-2-yl)-1-((2-(trimethylsilyl) ethoxy)methyl)-1H-pyrrolo[2,3-c]pyridine (97 mg, yield: 17.4%) as a light brown solid. MS (ESI): m/z=416.0 [M+H]+.

Example 30-5: 4-(7-Azido-1-((2-(trimethylsilyl)ethoxy)methyl)-1H-pyrrolo[2,3-c]pyridin-3-yl)-N-(2-fluoro-3-(methylsulfonyl)phenyl)-5-methylpyrimidin-2-amine

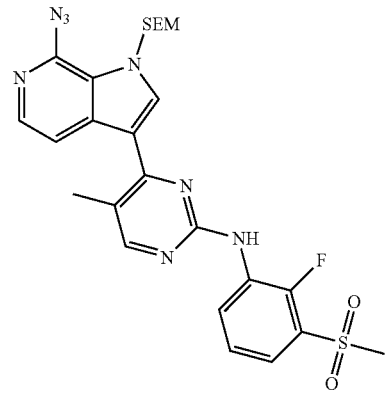 [SMILES: Cc1cnc(Nc2cccc(S(C)(=O)=O)c2F)nc1-c1cn(COCC[Si](C)(C)C)c2c(N=[N+]=[N-])nccc12]

To the mixture of 7-azido-3-(4,4,5,5-tetramethyl-1,3,2-dioxaborolan-2-yl)-1-((2-(trimethylsilyl)ethoxy)methyl)-1H-pyrrolo[2,3-c]pyridine (200 mg, 0.48 mmol), 4-chloro-N-(2-fluoro-3-(methanesulfonyl)phenyl)-5-methylpyrimidin-2-amine (198 mg, 0.63 mmol), potassium phosphate (133 mg, 0.96 mmol) and 1,4-dioxane (3.0 ml)/water (1.0 ml) was added Pd(dppf)Cl₂.DCM (33 mg, 0.04 mmol) under argon atmosphere. The reaction solution was heated to 90° C. and stirred for 6 hours. The reaction was monitored by LCMS. After cooled to room temperature, the reaction solution was extracted with ethyl acetate (5 ml×3). The combined organic phase was dried over anhydrous sodium sulfate and filtered. The filtrate was concentrated under reduced pressure to provide a crude product. The crude product was purified on a flash silica gel column (petroleum ether:ethyl acetate=1:1) to provide a pale yellow solid 4-(7-azido-1-((2-(trimethylsilyl)ethoxy)methyl)-1H-pyrrolo[2,3-c]pyridin-3-yl)-N-(2-fluoro-3-(methanesulfonyl)phenyl)-5-methylpyrimidin-2-amine (148 mg, yield: 54%). MS (ESI): m/z=569.0 [M+H]+.

Example 30-6: 4-(7-Azido-1H-pyrrolo[2,3-c]pyridin-3-yl)-N-(2-fluoro-3-(methylsulfonyl)phenyl)-5-methylpyrimidin-2-amine

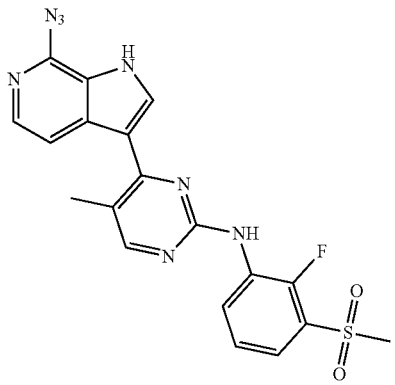 [SMILES: Cc1cnc(Nc2cccc(S(C)(=O)=O)c2F)nc1-c1c[nH]c2c(N=[N+]=[N-])nccc12]

A solution of 4-(7-azido-1-((2-(trimethylsilyl)ethoxy)methyl)-1H-pyrrolo[2,3-c]pyridin-3-yl)-N-(2-fluoro-3-(methylsulfonyl)phenyl)-5-methylpyrimidin-2-amine (148 mg, 0.26 mmol) in trifluoroacetic acid (3.0 ml) was added into a 10 ml sealed tube equipped with a magnetic stirrer. The reaction solution was heated to 50° C. and stirred for 2 hours. The reaction was monitored by LCMS. After the reaction solution was cooled to room temperature, it was concentrated under reduced pressure to provide a crude product. The solution was separated by preparative high performance liquid chromatography (NH4HCO3) to provide crude 4-(7-azido-1H-pyrrolo[2,3-c]pyridin-3-yl)-N-(2-fluoro-3-(methanesulfonyl)phenyl)-5-methylpyrimidin-2-amine (160 mg), the crude product was used directly for the next step without purification. MS (ESI): m/z=438.9 [M+H]$^+$.

Example 30-7: 3-(2-((2-Fluoro-3-(methylsulfonyl)phenyl)amino)-5-methylpyrimidin-4-yl)-1H-pyrrolo[2,3-c]pyridin-7-amine

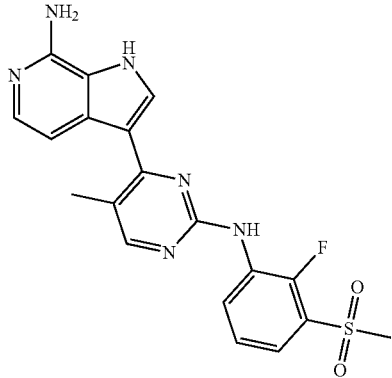 [SMILES: Cc1cnc(Nc2cccc(S(C)(=O)=O)c2F)nc1-c1c[nH]c2c(N)nccc12]

Into a 50 ml round bottom flask equipped with a magnetic stirrer, 4-(7-azido-1H-pyrrolo[2,3-c]pyridin-3-yl)-N-(2-fluoro-3-(methanesulfonyl)phenyl)-5-methylpyrimidin-2-amine (160 mg) (160 mg), tin chloride dihydrate (304 mg, 1.36 mmol) and ethanol (90%, 12 ml) solution were added. The reaction solution was heated to reflux and stirred for 16 hours. After the reaction was completed, the reaction solution was cooled to room temperature, followed by concentrating under reduced pressure to provide a crude product. The crude product was purified on a reverse silica gel column to provide 3-(2-((2-fluoro-3-(methylsulfonyl)phenyl)amino)-5-methylpyrimidin-4-yl)-1H-pyrrolo[2,3-c]pyridin-7-amine (80 mg, total yield: 71.4%). MS (ESI): m/z=412.8 [M+H]$^+$.

Example 30-8: 1-(3-(2-((2-Fluoro-3-(methylsulfonyl)phenyl)amino)-5-methylpyrimidin-4-yl)-1H-pyrrolo[2,3-c]pyridin-7-yl)-3-isopropylurea

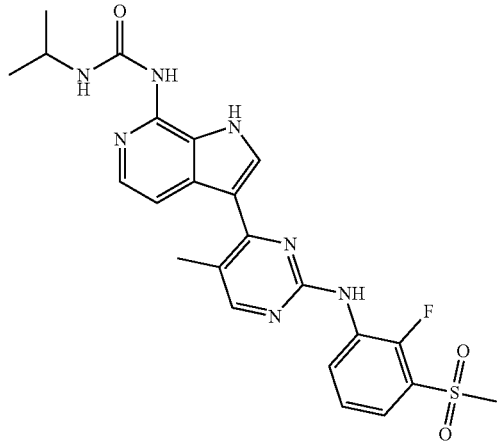

To the mixture of 3-(2-((2-fluoro-3-(methylsulfonyl)phenyl)amino)-5-methylpyrimidin-4-yl)-1H-pyrrolo[2,3-c]pyridin-7-amine (45 mg, 0.11 mmol) in tetrahydrofuran (2.0 mL) were added 2-isocyanatopropane (29 mg, 0.33 mmol) at room temperature. The reaction solution was stirred at 60° C. for 3 hours. The reaction was monitored by LCMS. The solvent was concentrated under reduced pressure to provide a crude product. Then the crude product was purified by preparative high performance liquid chromatography (HCOOH) to provide a white solid 1-(3-(2-((2-fluoro-3-(methylsulfonyl)phenyl)amino)-5-methylpyrimidin-4-yl)-1H-pyrrolo[2,3-c]pyridin-7-yl)-3-isopropylurea (18 mg, yield: 33.2%). MS (ESI): m/z=498.2. [M+H]$^+$.
$^1$H NMR (400 MHz, DMSO-d$_6$) δ 12.06-11.97 (m, 2H), 9.55 (d, J=6.8 Hz, 1H), 9.24 (s, 2H), 8.31 (s, 1H), 8.24 (d, J=5.2 Hz, 4H), 7.85 (d, J=5.6 Hz, 1H), 7.72 (d, J=5.6 Hz, 1H), 7.57 (d, J=6.3 Hz, 1H), 7.42 (t, J=8.0 Hz, 1H), 3.92 (d, J=6.8 Hz, 1H), 3.28 (s, 3H), 2.39 (s, 3H), 1.21 (d, J=6.4 Hz, 6H).

The following compounds were prepared according to the method in Example 30:

| Number | Compound structure | LCMS, HNMR |
|---|---|---|
| 32 | 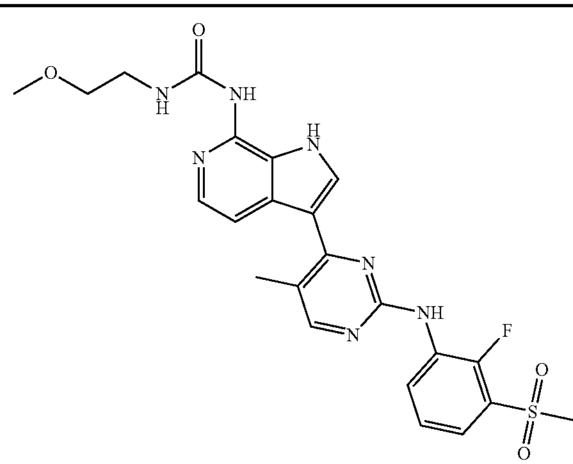 | MS (ESI): m/z = 514.0 [M + H]$^+$. <br> $^1$H NMR (400 MHz, DMSO-d$_6$) δ 12.04 (s, 1H), 9.73 (s, 1H), 9.37 (s, 1H), 9.24 (s, 1H), 8.32 (s, 2H), 8.27-8.21 (m, 2H), 7.87 (d, J = 5.7 Hz, 1H), 7.72 (d, J = 5.8 Hz, 1H), 7.56 (t, J = 7.6 Hz, 1H), 7.42 (t, J = 8.0 Hz, 1H), 3.46 (d, J = 4.2 Hz, 4H), 3.31 (s, 3H), 3.28 (s, 3H), 2.39 (s, 3H). |

| Number | Compound structure | LCMS, HNMR |
|---|---|---|
| 33 | 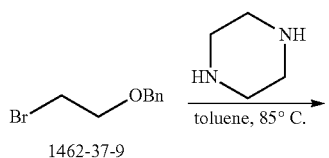 | MS (ESI): m/z = 499.6 [M + H]$^+$.<br>$^1$H NMR (400 MHz, DMSO-d$_6$)<br>δ 11.93-11.85 (m, 1H), 9.71 (s, 1H), 9.27 (s, 1H), 8.86 (d, J = 7.1 Hz, 1H), 8.73-8.67 (m, 1H), 8.55 (s, 1H), 8.39 (s, 1H), 8.25 (s, 1H), 8.14 (s, 1H), 7.49-7.43 (m, 1H), 7.40 (t, J = 8.0 Hz, 1H), 3.93 (dd, J = 13.6, 6.4 Hz, 1H), 2.34 (d, J = 8.4 Hz, 3H), 1.21 (t, J = 9.6 Hz, 6H). |
| 34 | 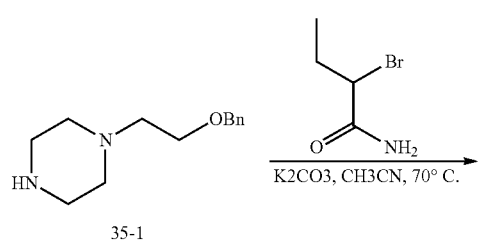 | MS (ESI): m/z = 436.1 [M + H]$^+$.<br>$^1$H NMR (400 MHz, DMSO-d$_6$)<br>δ 11.54-11.49 (m, 1H), 10.56 (s, 1H), 9.27 (s, 1H), 8.33 (s, 1H), 8.27 (s, 1H), 8.18 (d, J = 3.2 Hz, 1H), 8.14 (d, J = 5.6 Hz, 1H), 7.88 (d, J = 5.6 Hz, 1H), 7.56 (s, 1H), 7.43 (d, J = 8.0 Hz, 1H), 4.54-4.48 (m, 2H), 4.40 (t, J = 6.0 Hz, 2H), 3.48-3.42 (m, 1H), 3.40-3.35 (m, 1H), 3.29 (s, 3H), 2.69 (d, J = 17.2 Hz, 4H), 2.28 (s, 4H), 1.86-1.77 (m, 1H), 1.72-1.65 (m, 1H), 0.95 (t, J = 7.2 Hz, 3H). |

Example 35: 2-(4-(2-hydroxyethyl)piperazin-1-yl)-N-(3-(2-((3-methoxy-1-methyl-1H-pyrazole-4-yl)amino)-5-methylpyrimidin-4-yl)-1H-pyrrolo[2,3-c]pyridin-7-yl)butanamide

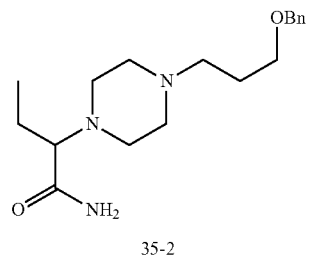

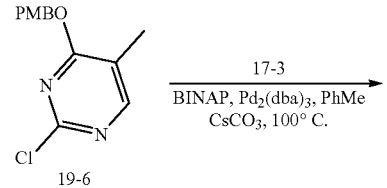

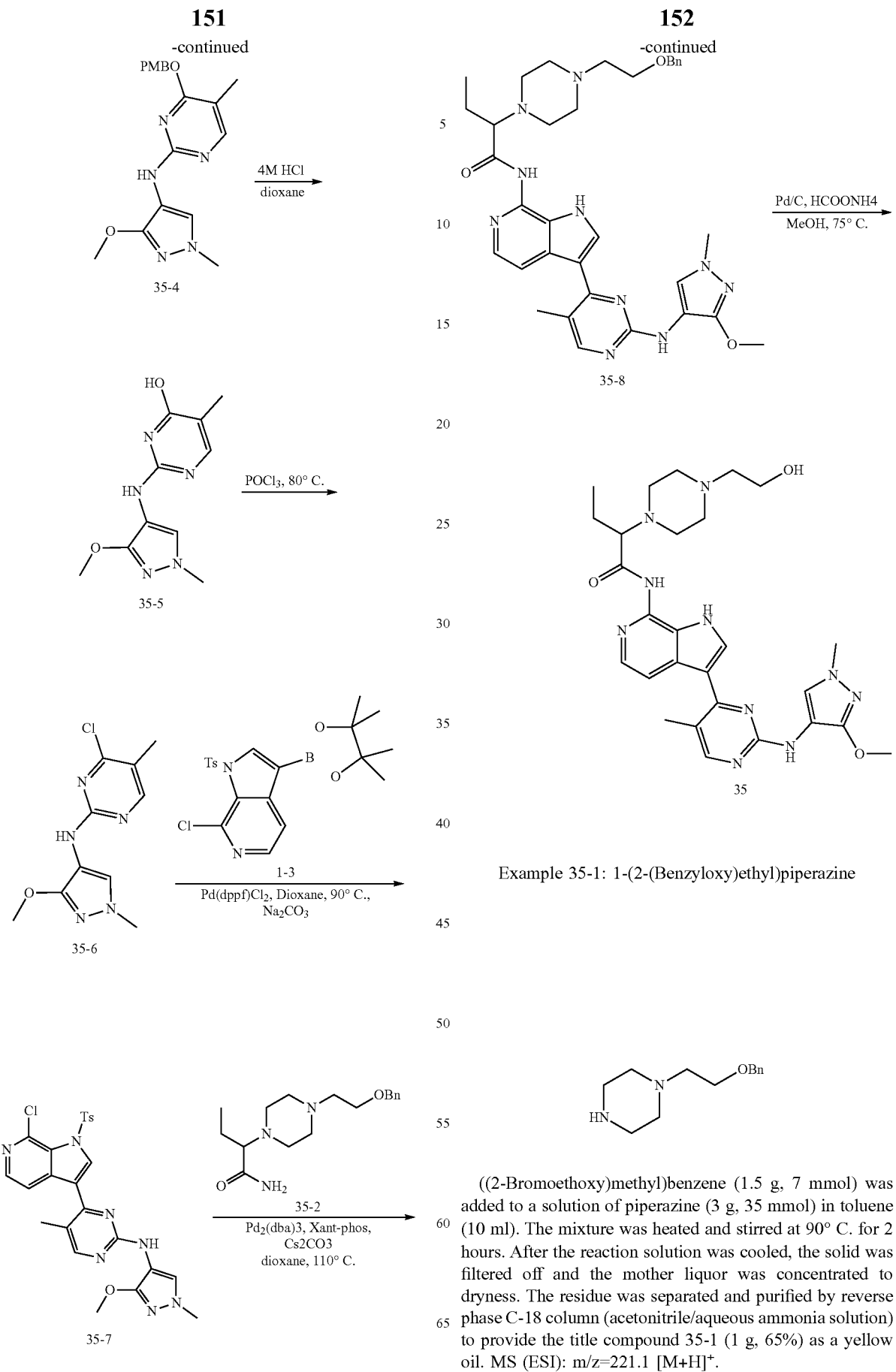

Example 35-1: 1-(2-(Benzyloxy)ethyl)piperazine ((2-Bromoethoxy)methyl)benzene (1.5 g, 7 mmol) was added to a solution of piperazine (3 g, 35 mmol) in toluene (10 ml). The mixture was heated and stirred at 90° C. for 2 hours. After the reaction solution was cooled, the solid was filtered off and the mother liquor was concentrated to dryness. The residue was separated and purified by reverse phase C-18 column (acetonitrile/aqueous ammonia solution) to provide the title compound 35-1 (1 g, 65%) as a yellow oil. MS (ESI): m/z=221.1 [M+H]⁺.

Example 35-2: 2-(4-(2-(Benzyloxy)ethyl)piperazin-1-yl)butanamide

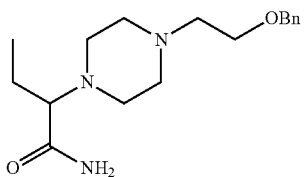 [SMILES: CCC(C(N)=O)N1CCN(CCOCc2ccccc2)CC1]

To a solution of compound 35-2 (500 mg, 2.3 mmol) and 2-bromobutyramide (377 mg, 2.3 mmol) in acetonitrile (5 mL) was added potassium carbonate (627 mg, 4.5 mmol). The mixture was heated and stirred for 70° C. for 16 hours. After the reaction solution was cooled, the inorganic salt was filtered off and the mother liquor was concentrated to residue. The residue was purified by reverse phase C-18 column (acetonitrile/aqueous ammonia solution) to give the title compound (400 mg, 58%) as a white solid. MS (ESI): m/z=306.2 [M+H]$^+$.

Example 35-4: N-(3-Methoxy-1-methyl-1H-pyrazol-4-yl)-4-((4-methoxybenzyl)oxo)-5-methylpyrimidine-2-amine

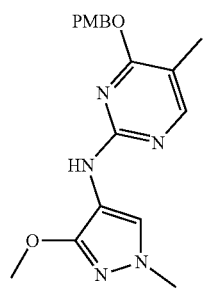

A solution of 4 (2.0 g, 7.5 mmol), YN-HDB-232 (0.95 g, 7.5 mmol), Pd$_2$(dba)$_3$ (0.13 g, 0.15 mmol), BINAP (0.18 g, 0.30 mmol), cesium carbonate (4.8 g, 15.0 mmol) in toluene (10 ml) was heated to 100° C. under the protection of nitrogen, and maintained at this temperature for 3 hours. The reaction solution was monitored by LC-MS. After the reaction was completed, water (200 ml) was added to the reaction solution, then the solution was extracted with ethyl acetate (200 ml×2). The organic layers were combined, washed with brine, dried over anhydrous sodium sulfate. The filtrate was evaporated under reduced pressure to remove the solvent. The crude product was purified by column (petroleum ether/ethyl acetate=1/1) to give a yellow solid 35-4 (2.2 g, 81.9% yield).

LC-MS: LC-MS (ESI): m/z (M+H)$^+$ 356.1.

Example 35-5: 2-((3-Methoxy-1-methyl-1H-pyrazol-4-yl)amino)-5-methylpyrimidine-4-phenol

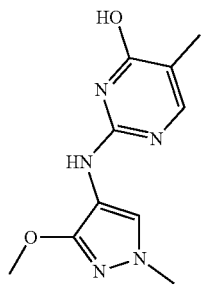

35-4 (2.0 g, 5.6 mmol) was added to 1,4 dioxane (20 ml) containing 4N hydrochloric acid and stirred at room temperature for thirty minutes, and the reaction was monitored by LC-MS. After the reaction was completed, the solvent was evaporated under reduced pressure. The crude product was added to ethyl acetate (20 ml) for recrystallization to provide a yellow solid 35-5 (1.2 g, 90.6% yield).

LC-MS: LC-MS (ESI): m/z (M+H)$^+$ 236.1

Example 35-6: 4-Chloro-N-(3-methoxy-1-methyl-1H-pyrazol-4-yl)-5-methylpyrimidin-2-amine

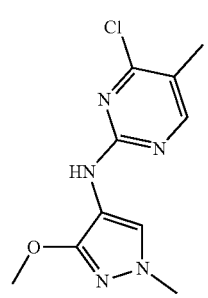

A solution of 35-5 (1.0 g, 4.2 mmol) in phosphorus oxychloride (10 ml) was heated to 80° C. and maintained for 3 hours. The reaction was monitored by LC-MS. After the reaction was completed, the phosphorus oxychloride was spin-dried. The crude product was extracted with saturated sodium bicarbonate solution (50 ml) and dichloromethane (50 ml×2). The organic layers were combined, washed with brine, dried with anhydrous sodium sulfate. The filtrate was evaporated under reduced pressure to remove the solvent. The crude product was purified by column (petroleum ether/ethyl acetate=1/1) to provide a yellow solid 35-6 (1.0 g, 92.7% yield)

LC-MS: LC-MS (ESI): m/z (M+H)$^+$ 254.

Example 35-7: 4-(7-Chloro-1-tosyl-1H-pyrrolo[2,3-c]pyridin-3-yl)-N-(3-methoxy-1-methyl-1H-pyrazol-4-yl)-5-methylpyrimidin-2-amine

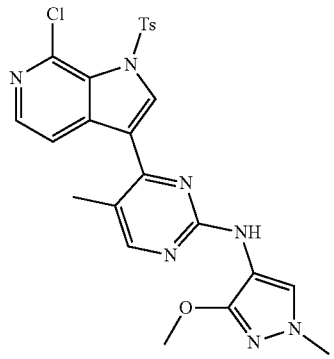 [SMILES: COc1nn(C)cc1Nc1ncc(C)c(-c2cn(S(=O)(=O)c3ccc(C)cc3)c3c(Cl)nccc23)n1]

A solution of 35-6 (0.4 g, 1.6 mmol), 1-3 (0.88 g, 2.1 mmol), Pd(dppf)Cl$_2$ (0.11 g, 0.16 mmol), sodium carbonate (0.5 g, 4.8 mmol) in dioxane (10 ml) and water (2 ml) was heated to 90° C. under nitrogen atmosphere, and maintained for 30 minutes. The reaction solution was monitored by LC-MS. After the reaction was completed, water (50 ml) was added to the reaction solution and the solution was extracted with dichloromethane (50 ml×2). The organic layers were combined, washed with brine, dried with anhydrous sodium sulfate. The filtrate was evaporated under reduced pressure to remove the solvent. The crude product was purified by column (dichloromethane/methanol=10/1) to provide 35-7 as a white solid (0.52 g, 62.9% yield).
LC-MS: LC-MS (ESI): m/z (M+H)$^+$ 524.1.

Example 35-8: 2-(4-(2-(Benzyloxy)ethyl)piperazin-1-yl)-N-(3-(2-((3-methoxy-1-methyl-1H-pyrazol-4-yl)amino)-5-methylpyrimidin-4-yl)-1H-pyrrolo[2,3-c]pyridin-7-yl)butanamide

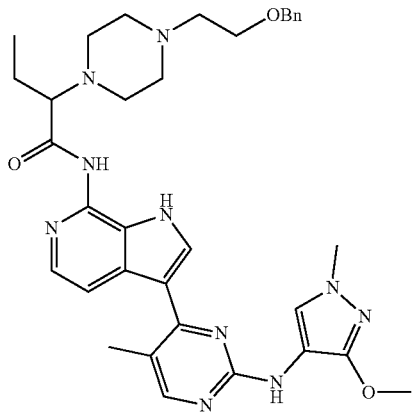 [SMILES: CCC(C(=O)Nc1nccc2c(-c3nc(Nc4cn(C)nc4OC)ncc3C)c[nH]c12)N1CCN(CCOCc2ccccc2)CC1]

To a solution of compound 35-7 (114 mg, 0.22 mmol), 35-2 (113 mg, 0.37 mmol), and cesium carbonate (200 mg, 0.62 mmol) in anhydrous dioxane (2 mL) was added tris(dibenzylideneacetone)dipalladium(0) (27 mg, 0.03 mmol) and 4,5-bisdiphenylphosphine-9,9-dimethylxanthene (35 mg, 0.06 mmol). The reaction mixture was heated at 110° C. and sealed under argon atmosphere for 16 hours. The reaction mixture was cooled and filtered and washed with methanol. The filtrate was concentrated, and the residue was separated and purified by reverse phase C-18 column (acetonitrile/formic acid aqueous solution) to provide the title compound (80 mg, 41%) as a yellow solid. MS (ESI): m/z=639.3[M+H]$^+$.

Example 35: 2-(4-(2-Hydroxyethyl)piperazin-1-yl)-N-(3-(2-((3-methoxy-1-methyl-1H-pyrazole-4-yl)amino)-5-methylpyrimidin-4-yl)-1H-pyrrolo[2,3-c]pyridin-7-yl)butanamide

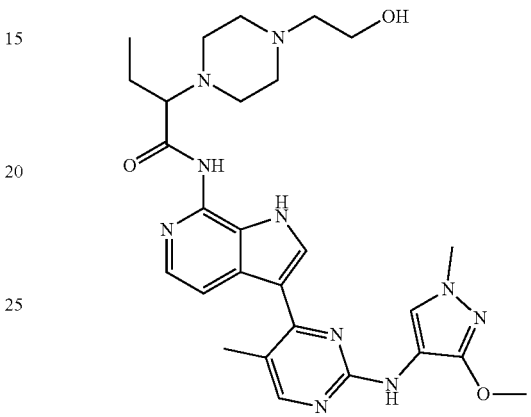

To a solution of compound 35-8 (48 mg, 0.075 mmol), ammonium formate (94 mg, 1.5 mmol) in methanol (5 mL) was added 10% palladium carbon (40 mg, water content 50%). The reaction mixture was heated and stirred under argon atmosphere at 75° C. for 3 hours. After the reaction solution was cooled, the catalyst was filtered off and the mother liquor was concentrated to dryness. The residue was prepared by high performance liquid chromatography to provide the title compound (9 mg, 22%) as a white solid. MS (ESI): m/z=549.2[M+H]$^+$.
$^1$H NMR (400 MHz, CD3OD): δ 8.16-8.13 (m, 2H), 8.09 (s, 1H), 7.91 (d, J=6.4 Hz, 1H), 7.66 (s, 1H), 3.90 (s, 3H), 3.73 (s, 3H), 3.70 (t, J=6.0 Hz, 2H), 3.25-3.22 (m, 1H), 2.86-2.66 (m, 8H), 2.60 (t, J=6.0 Hz, 2H), 2.39 (s, 3H), 1.97-1.86 (m, 2H), 1.08 (t, J=7.2 Hz, 3H).

Example 36: N-(3-(5-Fluoro-2-((3-methoxy-1-methyl-1H-pyrazol-4-yl) amino)pyrimidin-4-yl)-1H-pyrrolo[2,3-c]pyridin-7-yl)-2-(4-(oxbutan-3-yl)piperazin-1-yl)butanamide

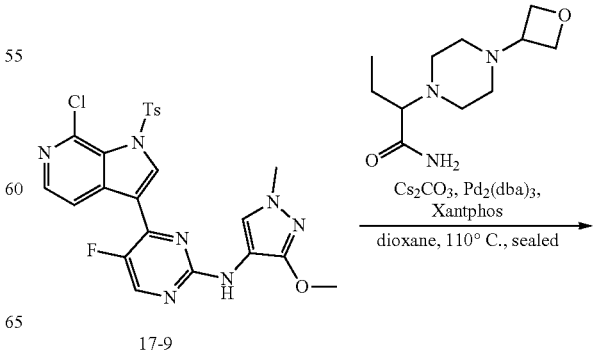

17-9

-continued

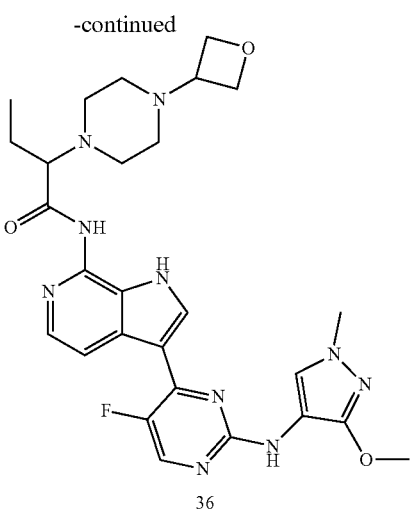

36

The target compound was obtained according to the method in Example 17, replacing the corresponding starting materials.

MS(ESI): m/z=565.53 [M+H]$^+$ $^1$HNMR (400 MHz, DMSO-d6) δ 11.59 (s, 1H), 10.56 (s, 1H), 8.43 (s, 2H), 8.30 (d, J=3.7 Hz, 1H), 8.21 (s, 1H), 7.92 (s, 1H), 7.65 (s, 1H), 4.49-4.46 (m, 2H), 4.36 (t, J=6.0 Hz, 2H), 3.76 (s, 3H), 3.68 (s, 3H), 3.43 (s, 1H), 3.38-3.32 (m, 1H), 2.66 (d, J=18.6 Hz, 4H), 2.25 (s, 4H), 1.85-1.72 (m, 1H), 1.69-1.62 (m, 1H), 0.91 (t, J=7.3 Hz, 3H).

Biological Test Example 1: In Vitro JAK1/2/3 Kinase Activity Assays

Recombinant human JAK1 protein was purchased from Thermo Fisher. JAK2 and JAK3 proteins were purchased from Carna Biosciences. HTRF kinEASE TK kit was purchased from Cisbio Bioassays. BioTek microplate reader Synergy Neo 2 was used to read the plate.

The test compounds were of 4-fold serial dilution, and the final concentration ranged from 10 μM to 0.04 nM in duplicates for each concentration. The concentration of DMSO in the reaction system was 1%.

JAK1 Enzyme Reaction:

The reaction included 0.5 ng/μl JAK 1 protein kinase, 1 μM TK Substrate-biotin peptide substrate, 1.1 μM ATP, 1× enzymatic buffer, 5 mM MgCl$_2$, 1 mM MnCl$_2$, 1 mM DTT, and 2.5 nM SEB. The detection plate was White Proxiplate 384-Plus plate (PerkinElmer), and the mixture (10 μl) was reacted at room temperature for 60 minutes.

JAK2 Enzyme Reaction:

The reaction included 0.001 ng/μl JAK 2 protein kinase, 1 μM TK Substrate-biotin peptide substrate, 2.7 μM ATP, 1× enzymatic buffer, 5 mM MgCl$_2$, and 1 mM DTT. The detection plate was White Proxiplate 384-Plus plate (PerkinElmer), and the mixture (10 μl) was reacted at room temperature for 25 minutes.

JAK3 Enzyme Reaction:

The reaction included 0.004 ng/gi JAK 3 protein kinase, 1 μM TK Substrate-biotin peptide substrate, 0.75 μM ATP, 1× enzymatic buffer, 5 mM MgCl$_2$, and 1 mM DTT. The detection plate was White Proxiplate 384-Plus plate (PerkinElmer), and the mixture (10 μl) was reacted at room temperature for 25 minutes.

Reaction detection: 10 μl of detection reagent was added to the reaction plate containing final concentration of 0.125 μM of SA-XL665 and 5 μl 1×TK-Antibody. The mixture was incubated overnight at room temperature. The plate was read using Synergy Neo 2.

Data analysis: 665/620 Ratio was converted into inhibition rate (%) through the following formula: inhibition rate (%)=(Ratio$_{max}$−Ratio$_{test}$)/(Ratio$_{max}$−Ratio$_{min}$)×100%.

Ratio$_{max}$ is a positive control without detection compound, Ratio$_{min}$ is a negative control without detection compound and kinase, Ratio$_{test}$ is the detection value of each concentration of different compounds. 4 parameter curve fitting was performed to measure the IC50 (nM) values. The details are shown in, Table 1.

TABLE 1

IC$_{50}$ value of some compounds in enzyme activity assays

| Example | JAK1 | JAK2 | JAK3 |
|---|---|---|---|
| 1 | C | E | H |
| 2 | B | D | G |
| 3 | B | D | G |
| 4 | A | D | G |
| 5 | B | D | G |
| 6 | B | D | G |
| 7 | B | D | G |
| 8 | B | D | G |
| 9 | B | D | G |
| 10 | B | E | H |
| 11 | B | E | H |
| 12 | A | D | G |
| 17 | A | E | G |
| 18 | A | E | G |
| 19 | A | E | H |
| 20 | B | E | H |
| 21 | A | E | H |
| 22 | B | D | H |
| 23 | B | E | H |
| 24 | B | E | H |
| 25 | A | D | H |
| 26 | C | E | H |
| 27 | A | E | H |
| 28 | A | D | H |
| 29 | C | E | H |
| 30 | B | E | G |
| 32 | A | D | G |
| 33 | B | E | G |

The definition of each letter is shown in the following table:

| | Letter | IC50, nM |
|---|---|---|
| JAK1 | A | <5 |
| | B | 5~50 |
| | C | >50 |
| JAK2 | D | <100 |
| | E | 100~10000 |
| | F | >10000 |
| JAK3 | G | <500 |
| | H | 500~10000 |
| | I | >10000 |

Biological Test Example 2: Cellular JAK1/2 Activity Assays

In TF-1 cells, IL-6 stimulation leads to phosphorylation of STAT3 through JAK1, while EPO stimulants phosphorylation of STAT5 via JAK2.

TF-1 cells were obtained from American Type Culture Collection (ATCC). TF-1 cells were starved overnight (cell density was 100,000 cells/well at plating) in OptiMEM medium without phenol red containing 0.5% fetal bovine serum (FBS), 0.1 mM non-essential amino acids (NEAA), 1 mM sodium pyruvate at 37° C. The compound was serially diluted in DMSO, added to TF-1 cells and incubated at 37° C. for 20 minutes. The final concentration of DMSO was 0.2%. Then, human recombinant cytokine IL-6 (30 ng/mL) or EPO (10 U/mL) was added to the wells containing TF-1 cells. After the cell plate was incubated for 30 minutes, cells were lysed, and the phosphorylation of STAT3 (IL-6) or STAT5 (EPO) in the cell lysate (pSTAT3/total STAT3 Elisa Kit: CST #7300C/CST #7305C; pSTAT5 and total STAT5 Elisa Kit: Abcam #ab205715) was measured. The IC50 value was determined as the concentration of the compound required to inhibit STAT phosphorylation by 50% relative to the measured DMSO control.

TABLE 2

$IC_{50}$ values of some compounds in cell assays

| Example | Cell JAK1 | Cell JAK2 |
| --- | --- | --- |
| 2 | J | M |
| 3 | J | M |
| 4 | J | M |
| 5 | K | O |
| 6 | K | M |
| 7 | K | N |
| 8 | K | O |
| 9 | K | M |
| 10 | L | O |
| 12 | J | M |
| 19 | K | O |
| 21 | J | O |
| 22 | K | M |
| 23 | K | N |
| 24 | K | O |
| 25 | K | O |
| 27 | K | O |
| 28 | K | N |
| 30 | J | N |
| 32 | L | O |
| 33 | L | O |

The definition of each letter is shown in the following table:

| | Letter | IC50, nM |
| --- | --- | --- |
| JAK1 | J | <100 |
| | K | 100~1000 |
| | L | >1000 |
| JAK2 | M | <10000 |
| | N | 10000~20000 |
| | O | >20000 |

Biological Test Example 3: Human Whole Blood JAK Activity Assay

Compound inhibition of JAK1 and JAK2 activities was measured in human whole blood: inhibition of IL-6-induced STAT1 phosphorylation (CD4+ T cells) and GM-CSF-induced STAT5 phosphorylation (CD33+ cells) in human whole blood were respectively analysized. The experimental procedures are shown as follows:

1) Human whole blood was collected into heparinized tubes, and seeded in a 96-well plate at 100 L/well, and incubated in a cell incubator for 15 minutes.

2) Different concentrations of compounds (25 μL/well) were added into desired wells and incubated at 37° C. under 5% $CO_2$ for 30 minutes. The final concentration of DMSO was 0.2%.

3) Blood cells were stimulated with recombinant human IL-6 (100 ng/mL) or recombinant human GM-CSF (20 ng/mL) or PBS at 37° C. and 5% $CO_2$ for 20 minutes.

4) The blood was treated with pre-warmed 1× Lysis/Fixing Buffer (BD Phosflow) at 37° C. for 10 minutes to lyse erythrocytes and fix leukocytes.

5) After the cells were permeabilized with pre-cooled buffer (Perm buffer III) on ice for 60 minutes, anti-pSTAT1 and anti-CD4 antibodies (IL-6 stimulated samples) or anti-pSTAT5 and anti-CD33 antibodies (GM-CSF stimulated samples) were used to stain the samples at 4° C. for 60 minutes.

7) The cells were washed twice and resuspended in buffer for FACS analysis (Thermo Attune NxT).

The results of one representative compound of the present invention are shown in the following table:

| example | IC50_JAK1 (IL6/pSTAT1) | IC50_JAK2 (GM-CSF/pSTAT5) |
| --- | --- | --- |
| 4 | <500 nM | >20000 nM |

Biological Test Example 4: Mouse Pharmacokinetics

Test compound was intravenously (IV) or orally (PO) administrated to CD-1 mice. Blood samples were collected at different time points as indicated below. The concentration of the compounds in the mouse plasma was determined by LC-MS/MS and related parameters were calculated. The details are as follows: the required amount of the test product was taken to prepare a solution of the required concentration for intravenous injection or oral administration. The age of the animals was about 6-8 weeks at the beginning of the dosing experiment. Blood sampling time points are 0.083 h, 0.25 h, 0.5 h, 1 h, 2 h, 4 h, 8 h and 24 h after compound administration. The Phoenix WinNonlin 7.0 software was used to calculate the pharmacokinetic parameters through the blood drug concentration data at different time points.

The results of representative compounds of the present invention were shown in the following table:

| Pharmacokinetics in mice (5 mg/kg, P.O.) | | | | |
| --- | --- | --- | --- | --- |
| Parameters | Unit | Example 21 | Example 25 | Example 4 |
| $C_{max}$ | ng/mL | 264 | 155 | 1065 |
| $AUC_{0-24\,hr}$ | hr*ng/mL | 1682 | 946 | 10249 |
| $T_{1/2}$ | hr | 2.61 | 3.57 | 3.79 |
| F | % | 97.1 | 66.1 | 106 |

The invention claimed is:
1. A compound according to Formula I:

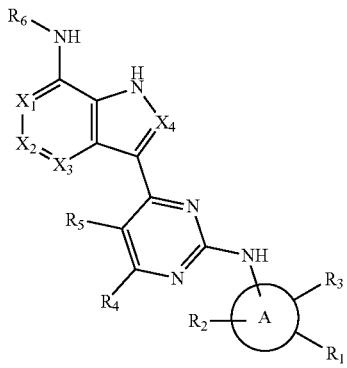

wherein, $X^1$ is N, $X^2$, $X^3$, and $X^4$ are each independently CH; and

ring is phenyl or pyrazol $R^1$ is independently selected from the group consisting of H, substituted or unsubstituted C1-C6 alkyl, substituted or unsubstituted 3-6 membered heterocyclyl, and —S(=O)$_2$R$_7$, wherein the heterocyclyl including 1-3 heteroatoms selected from N, S and O;

$R^2$, and $R^3$ are independently selected from the group consisting of H, halogen, CN, substituted or unsubstituted C1-C6 alkyl, substituted or unsubstituted C1-C6 alkoxyl, substituted or unsubstituted 3-6 membered heterocyclyl, —S(=O)$_2$R$_7$, and —NHS(=O)$_2$R$_7$, wherein the heterocyclyl including 1-3 heteroatoms selected from N, S and O;

$R^4$ is H, $R^5$ is selected from the group consisting of H, halogen, CN, and substituted or unsubstituted C1-C6 alkyl;

$R^6$ is selected from the group consisting of $R^7$—C(=O)—, $R^9R^{10}$N—C(=O)—, substituted or unsubstituted 5-12 membered heterocyclyl with 1-3 heteroatoms selected from N, S and O, substituted or unsubstituted C6-C10 aryl, and substituted or unsubstituted 5-10 membered heteroaryl with 1-3 heteroatoms selected from the group consisting of N, S and O;

$R^7$, $R^9$, and $R^{10}$ are each independently selected from the group consisting of H, substituted or unsubstituted C1-C6 alkyl, substituted or unsubstituted C1-C6 alkoxyl, substituted or unsubstituted C3-C8 cycloalkyl, and substituted or unsubstituted 5-12 membered heterocyclyl with 1-3 heteroatoms selected from the group consisting of N, S and O;

unless otherwise specified, "substituted" refers to being substituted by one or more substituents selected from the group consisting of halogen, C1-C6 alkoxyl, halogenated C1-C6 alkoxyl, C3-C8 cycloalkyl, halogenated C3-C8 cycloalkyl, methyl sulfone, oxo(=O), —CN, hydroxy, —NH$_2$, C1-C6 amine, carboxy, C1-C6 amide, and substituted or unsubstituted groups selected from the group consisting of C1-C6 alkyl, C6-C10 aryl, 5-10 membered heteroaryl with 1-3 heteroatoms selected from N, S, and O, —(CH$_2$)-C6-C10 aryl,—(CH$_2$)-(5-10 membered heteroaryl with 1-3 heteroatoms selected from N, S and O), -(5-10 membered heteroarylene with 1-3 heteroatoms selected from N, S and O)-(C1-C6 alkyl), 5-12 membered heterocyclyl with 1-3 heteroatoms selected from N, S and O, and the substituents thereof are selected from the group consisting of halogen, C1-C6 alkyl, C1-C6 alkylene-OH, C1-C6 alkoxyl, oxo, —S(O)$_2$CH$_3$, —CN, —OH, C6-C10 aryl, 3-10 membered heteroaryl with 1-3 heteroatoms selected from N, S and O, —C(O) CH$_2$NH$_2$, and —C(O) CH$_2$OH;

and in the compound of Formula I, each chiral center is in R configuration or S configuration.

2. The compound of claim 1, wherein the compound of Formula I has a structure according to Formula Ia or Ib:

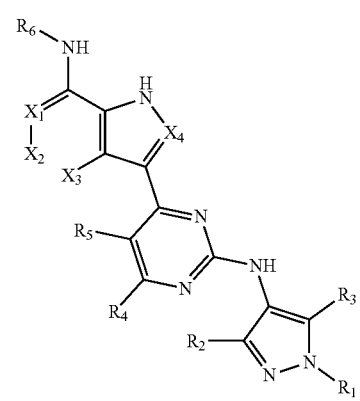

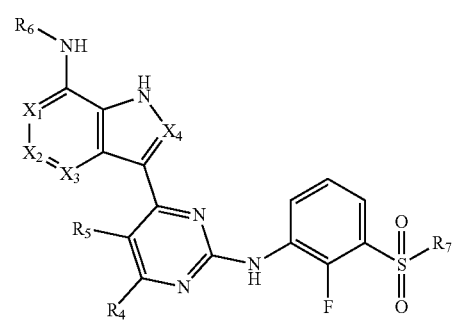

wherein, $R_7$ is selected from the group consisting of H, substituted or unsubstituted C1-C6 alkyl, and substituted or unsubstituted C3-C8 cycloalkyl.

3. The compound of claim 1, wherein the compound of Formula I has a structure selected from the following group:

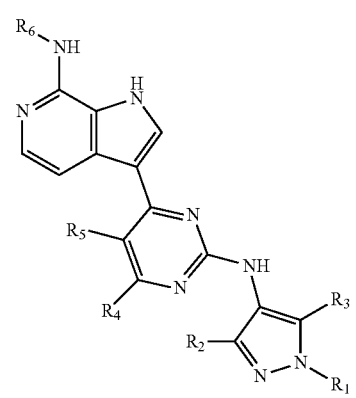

-continued

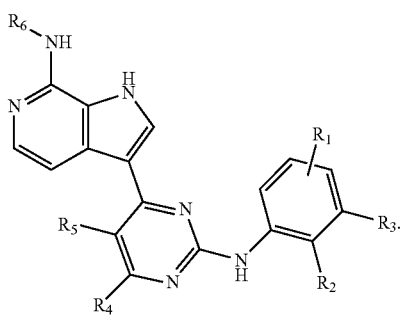

4. The compound of claim 1, wherein the compound has a structure according to Formula II:

II

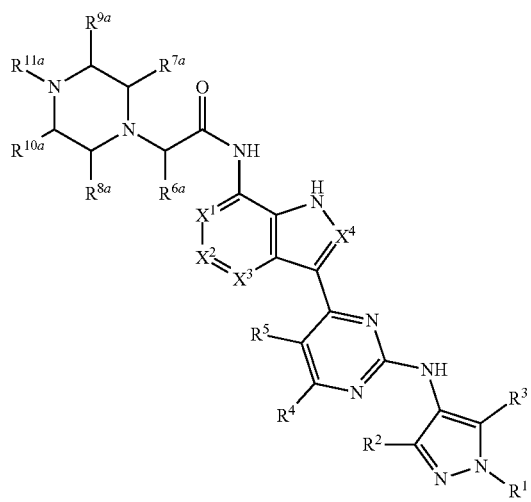

wherein,

- $R^{6a}$ is selected from the group consisting of H, substituted or unsubstituted C1-C6 alkyl, and substituted or unsubstituted C1-C6 alkoxyl;
- $R^{7a}$, $R^{8a}$, $R^{9a}$, and $R^{10a}$ are selected from the group consisting of hydrogen, halogen, and substituted or unsubstituted C1-C6 alkyl;
- $R^{11a}$ is selected from the group consisting of hydrogen, substituted or unsubstituted C1-C6 alkyl, substituted or unsubstituted C1-C6 alkoxyl, and substituted or unsubstituted C1-C6 amine;
- or any two groups of $R^{7a}$, $R^{8a}$, $R^{9a}$, $R^{10a}$ or $R^{11a}$ are connected to form —(CH$_2$)$_n$—, wherein n is 1; and
- wherein, the substitution refers to one or more hydrogen atoms on the group being replaced by the substituents selected from the group consisting of halogen, hydroxyl, and C1-C6 alkoxyl.

5. The compound of claim 4, wherein $R^{7a}$, $R^{8a}$, $R^{9a}$, and $R^{10a}$ are each independently selected from the group consisting of hydrogen and methyl; and wherein $R^{11a}$ is selected from the group consisting of methyl, ethyl, hydroxyethyl, methoxyethyl, and halogenated C1-C6 alkyl.

6. The compound of claim 1, wherein the compound of Formula I is selected from the following group:

1

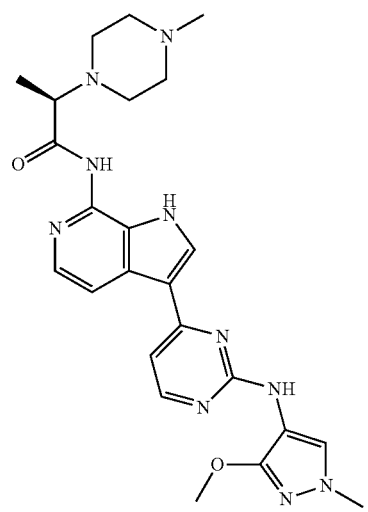

19

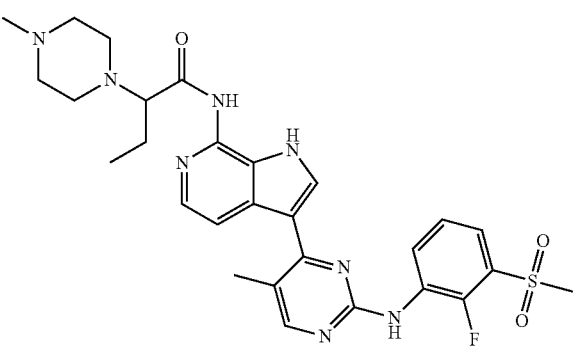

2

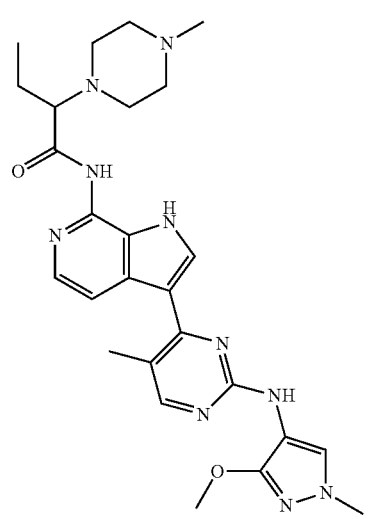

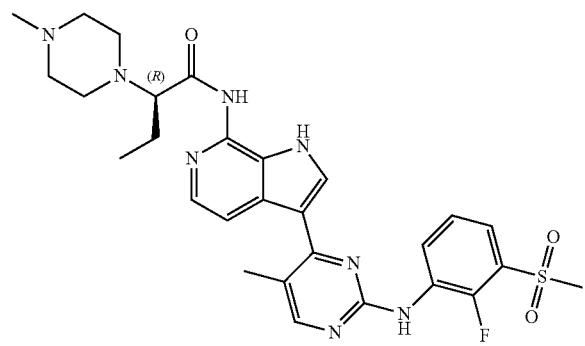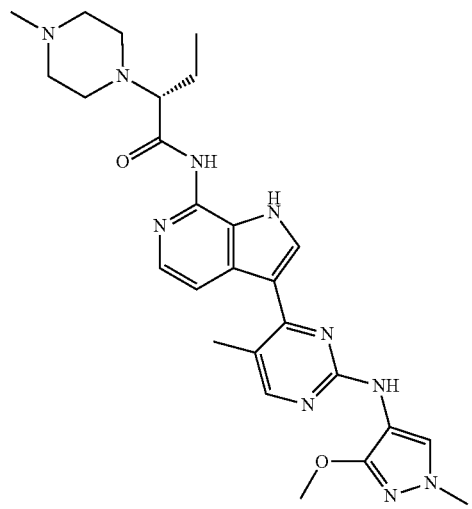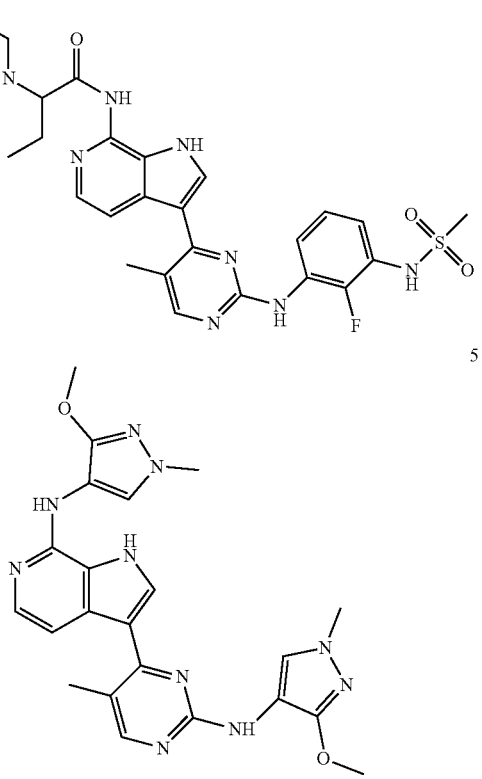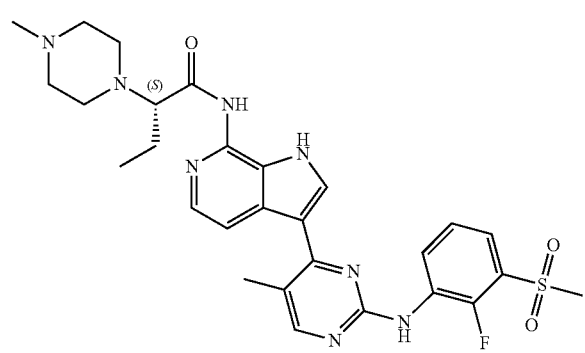

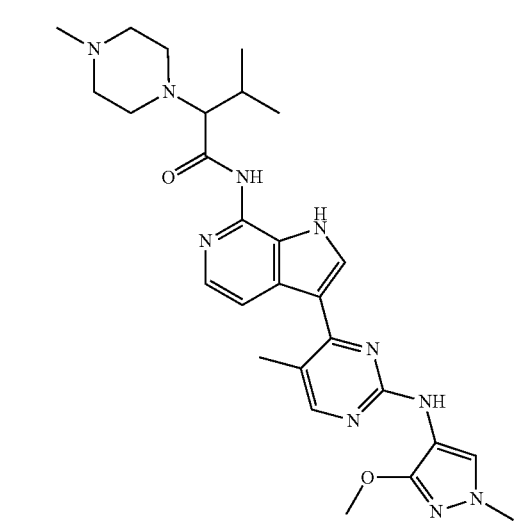
6
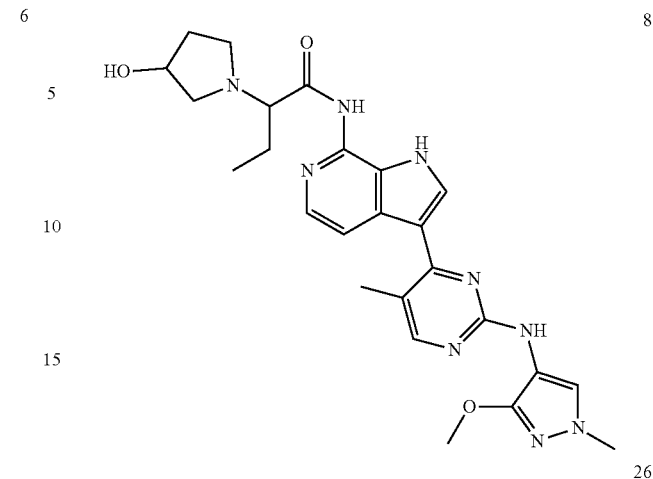
8
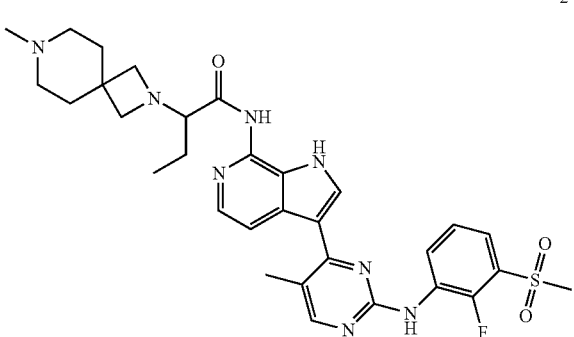
24
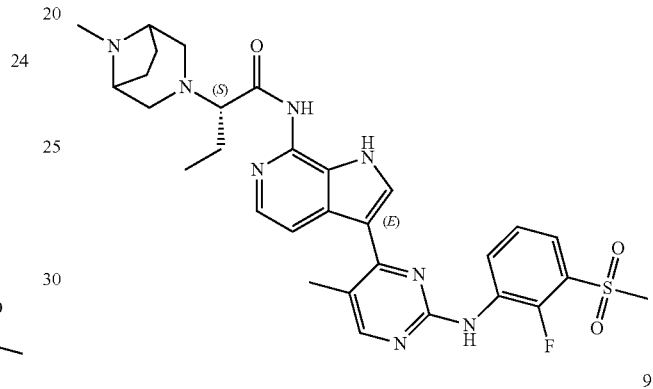
26
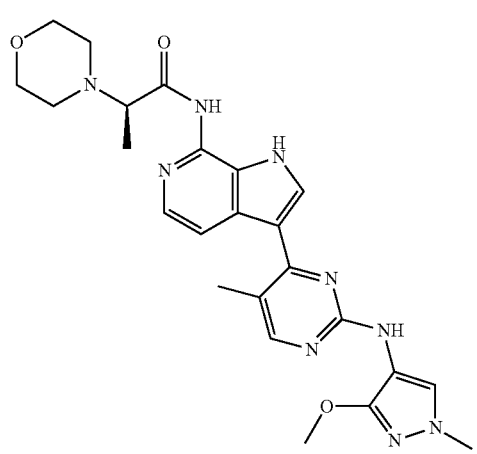
7
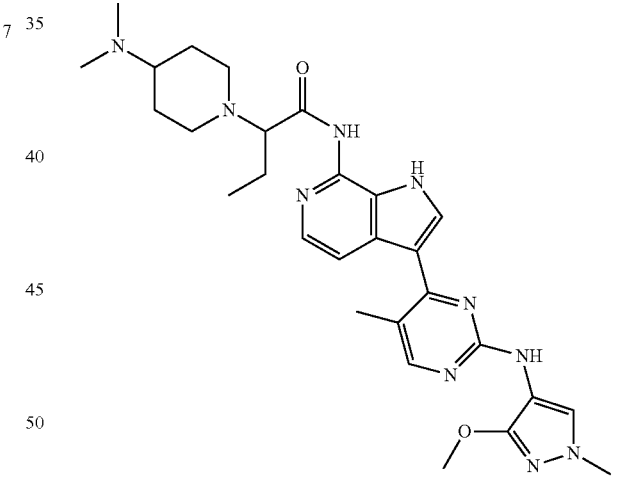
9
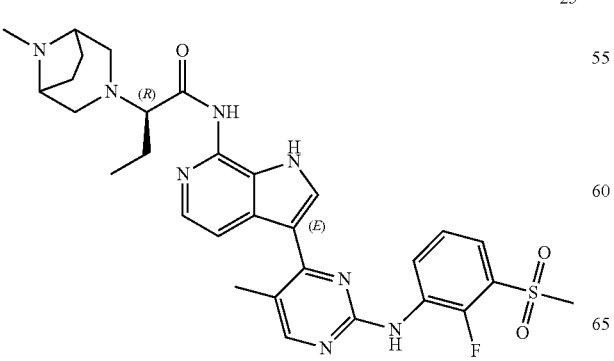
25
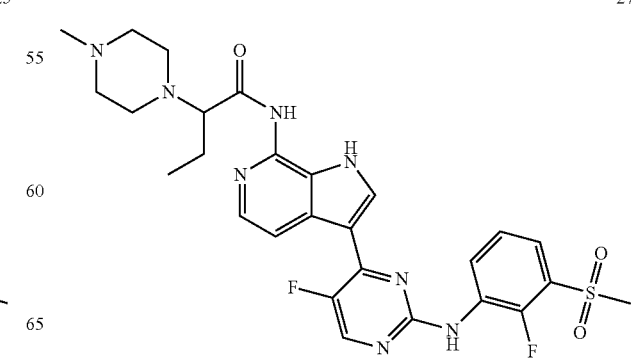
27

169
-continued
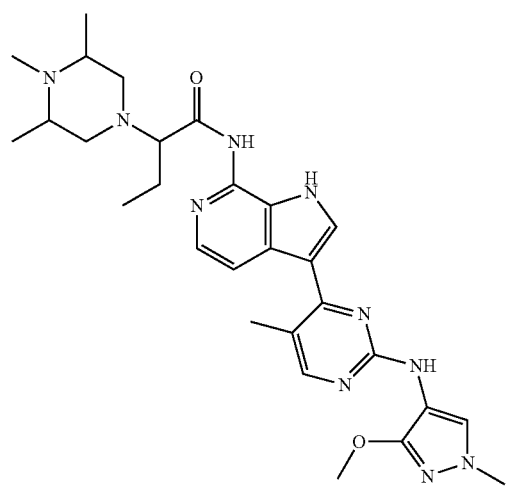
10
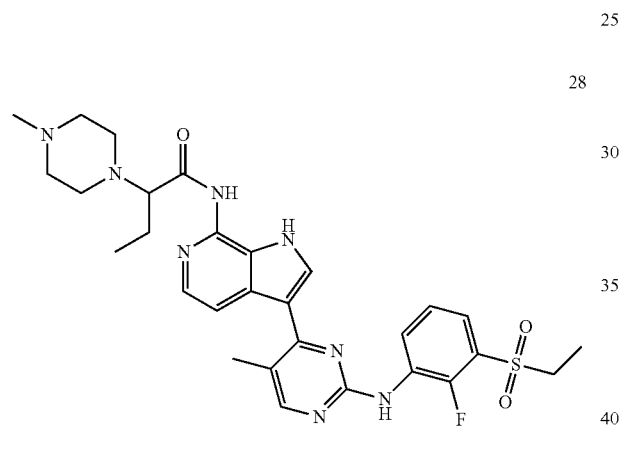
28
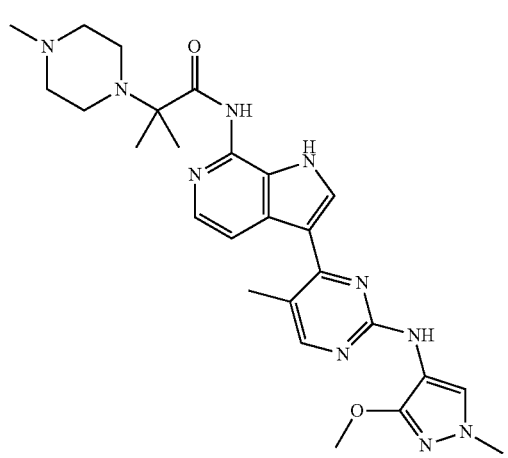
11
170
-continued
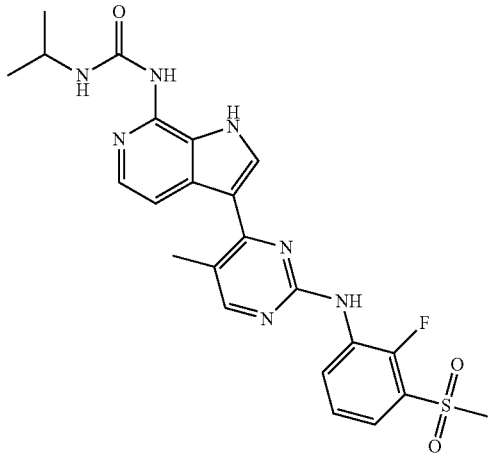
30
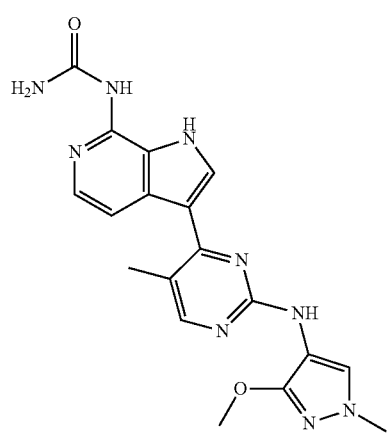
12
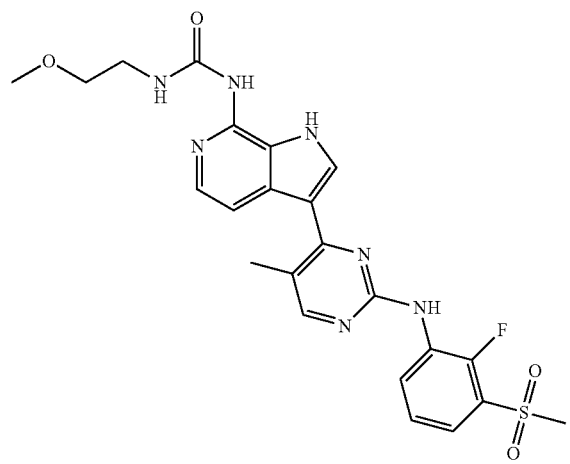
32

| 171 | 172 |
|---|---|
| -continued | -continued |
| 17 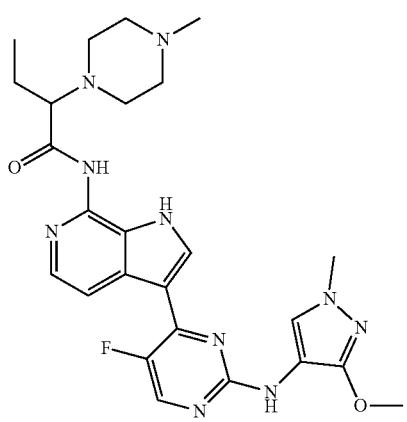 | 35 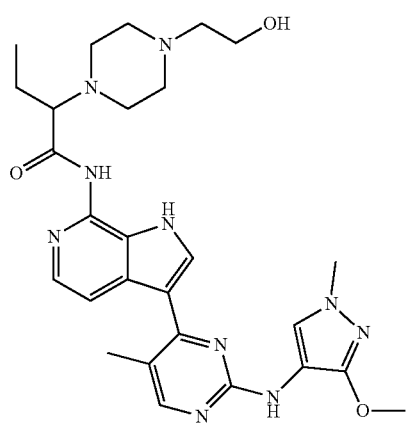 |
| 34 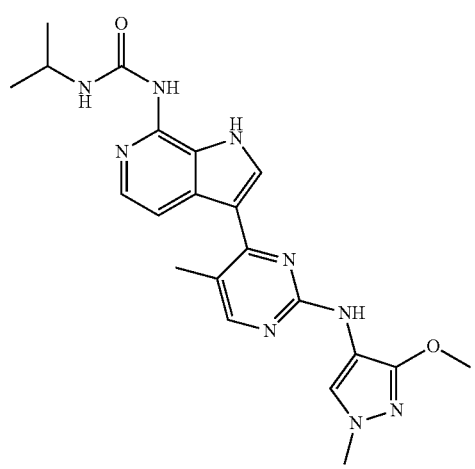 | 37 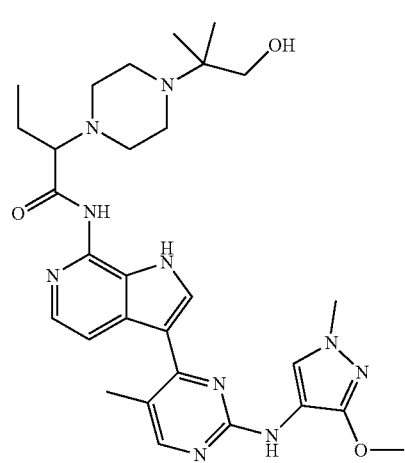 |
| 18 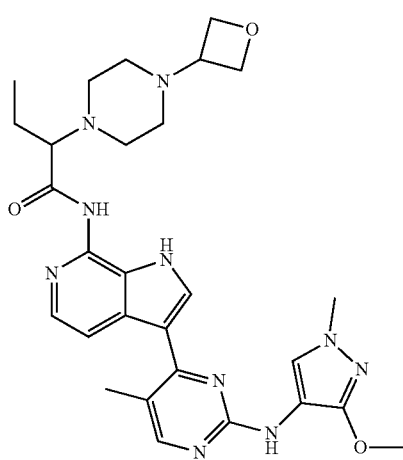 | 36 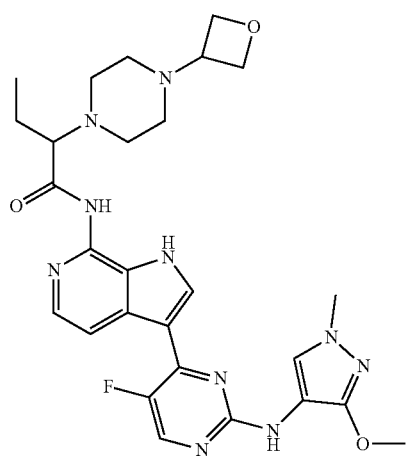 |

38
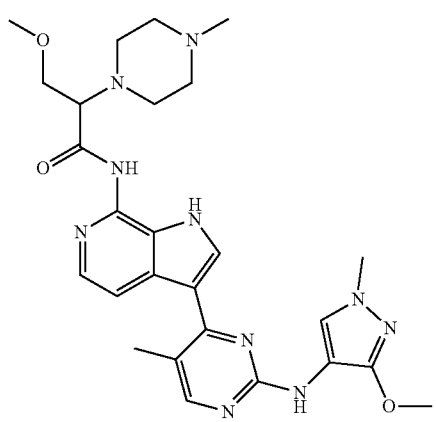
49
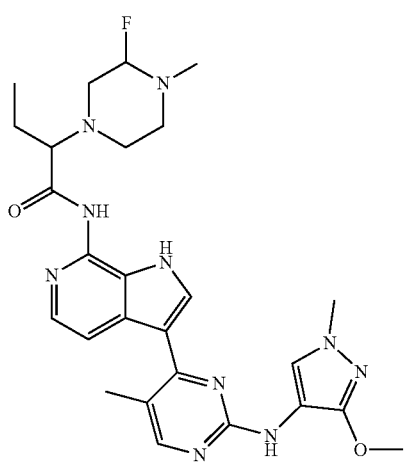
39
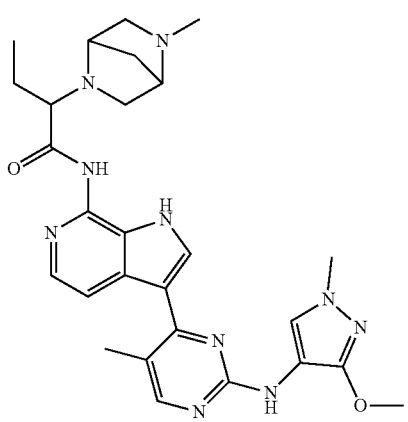
50
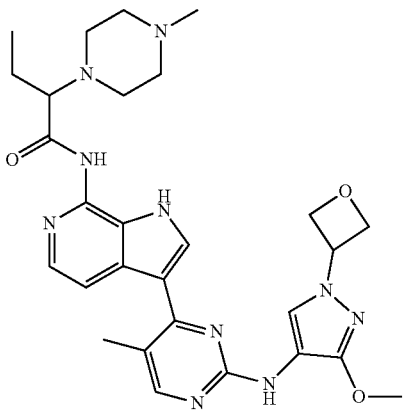
40
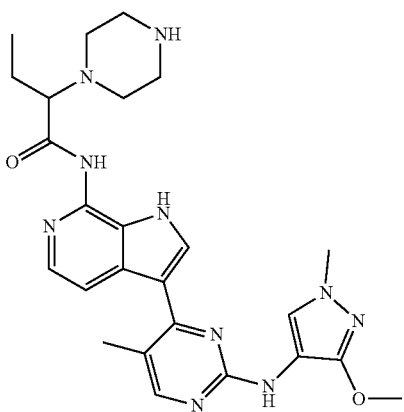
51
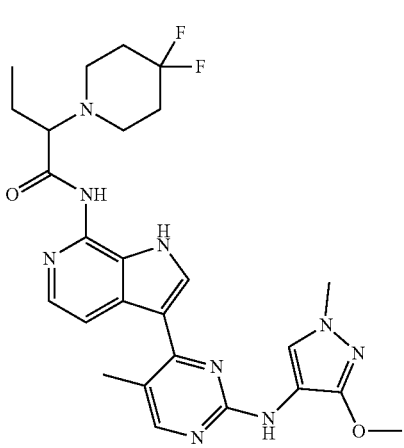

41
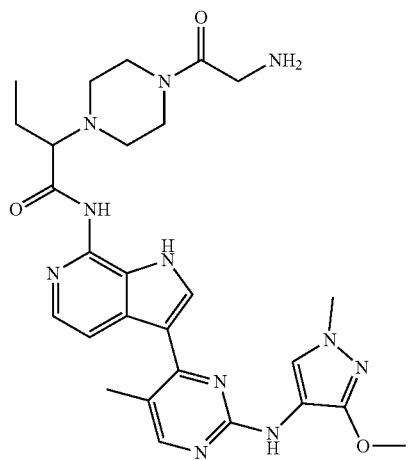
52
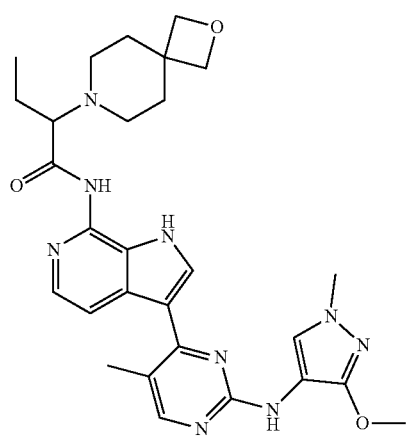
42
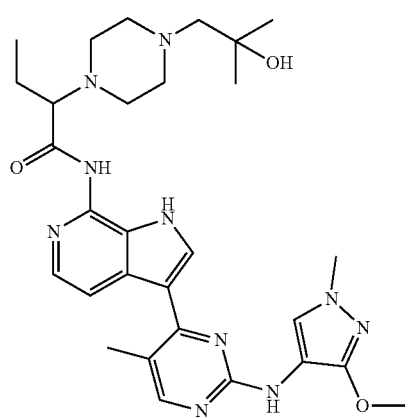
53
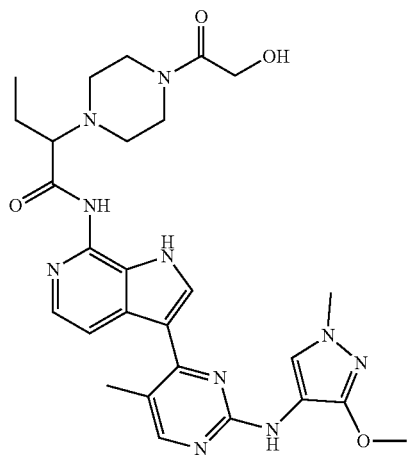
43
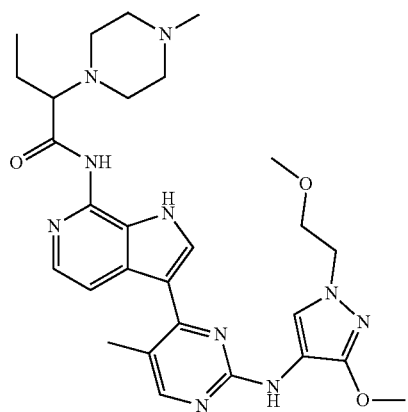
55
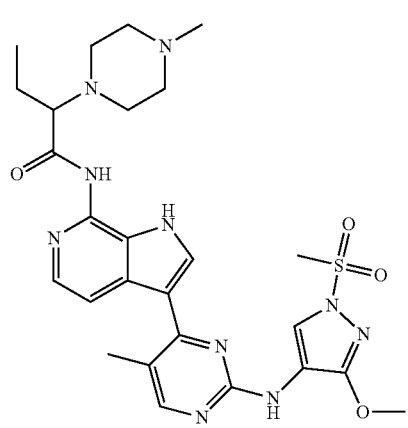

-continued

44

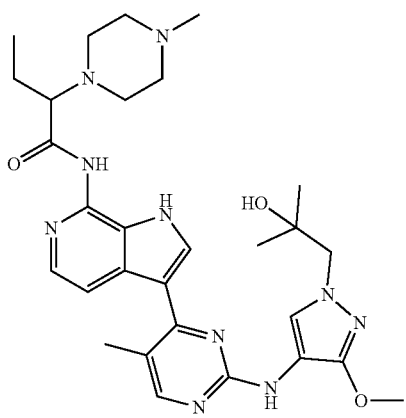

56

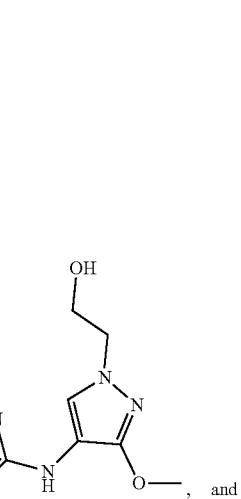
, and

-continued

31

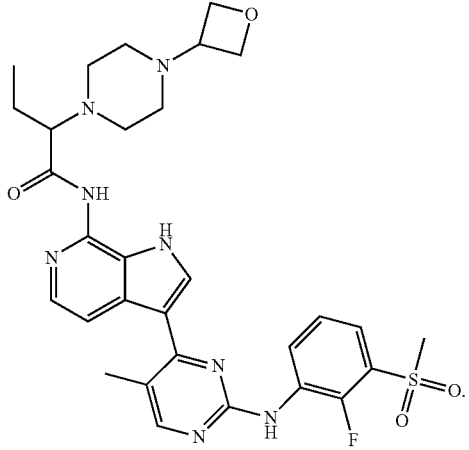

7. A pharmaceutical composition comprising: (1) the compound of claim 1 or stereoisomers or tautomers thereof, or pharmaceutically acceptable salts, hydrates or solvates thereof; (2) a pharmaceutically acceptable carrier.

8. A method of treating a disease related to the activity or expression of JAK kinase, the method comprising administering to a subject in need thereof an effective amount of a compound of claim 1 or stereoisomers or tautomers thereof, or pharmaceutically acceptable salts, hydrates or solvates thereof; wherein the disease is selected from the group consisting of non-small cell lung cancer, colon cancer, bladder cancer, breast cancer, blood cancer, stomach cancer, cardiovascular diseases, inflammation, immune or inflammatory diseases, myeloproliferative diseases, diabetic nephropathy, diabetic retinopathy, non-alcoholic steatohepatitis, and hepatic fibrosis.

9. A JAK inhibitor, wherein the inhibitor comprises the compound of claim 1, or stereoisomers or tautomers thereof, or pharmaceutically acceptable salts, hydrates or solvates thereof.

* * * * *